(12) United States Patent
Kmiec et al.

(10) Patent No.: US 7,468,244 B2
(45) Date of Patent: *Dec. 23, 2008

(54) POLYMORPHISM DETECTION AND SEPARATION

(75) Inventors: Eric B. Kmiec, Landenberg, PA (US); Michael C. Rice, Newton, PA (US)

(73) Assignee: University of Delaware, Newark, DE (US)

( * ) Notice: Subject to any disclaimer, the term of this patent is extended or adjusted under 35 U.S.C. 154(b) by 174 days.

This patent is subject to a terminal disclaimer.

(21) Appl. No.: 10/260,150

(22) Filed: Sep. 27, 2002

(65) Prior Publication Data
US 2003/0180746 A1 Sep. 25, 2003

Related U.S. Application Data

(63) Continuation-in-part of application No. PCT/US02/09691, filed on Mar. 27, 2002.

(60) Provisional application No. 60/325,828, filed on Sep. 28, 2001.

(51) Int. Cl.
*C07H 21/04* (2006.01)
*C12P 19/34* (2006.01)
*C12Q 1/68* (2006.01)

(52) U.S. Cl. .................. 435/6; 435/91.1; 536/23.1; 536/24.3

(58) Field of Classification Search ............ 435/6, 435/91.2, 91.1; 536/23.1, 24.3
See application file for complete search history.

(56) References Cited

U.S. PATENT DOCUMENTS

| | | | |
|---|---|---|---|
| 4,888,274 A | 12/1989 | Radding et al. | |
| 5,223,414 A | 6/1993 | Zarling et al. | |
| 5,273,881 A | 12/1993 | Sena et al. | |
| 5,432,272 A | 7/1995 | Benner | |
| 5,468,629 A | 11/1995 | Calhoun | |
| 5,506,098 A | 4/1996 | Zarling et al. | |
| 5,565,350 A | 10/1996 | Kmiec | |
| 5,670,316 A * | 9/1997 | Sena et al. ............ | 435/6 |
| 5,670,325 A | 9/1997 | Lapidus et al. | |
| 5,674,698 A | 10/1997 | Zarling et al. | |
| 5,698,397 A | 12/1997 | Zarling et al. | |
| 5,719,023 A | 2/1998 | Zarling et al. | |

(Continued)

FOREIGN PATENT DOCUMENTS

EP 0 322 311 12/1988

(Continued)

OTHER PUBLICATIONS

Bryant et al. "On the mechanism of renaturation of complementary DNA strands by the recA protein of *Escherichia coli*", PNAS, vol. 82, Jan. 1985, pp. 297-301.*

(Continued)

*Primary Examiner*—Sarae Bausch
(74) *Attorney, Agent, or Firm*—McCarter & English

(57) ABSTRACT

Methods and compositions for polymorphism detection and separation. The methods are readily multiplexed, can be adapted to a variety of existing detection systems, and permit target amplification without PCR. The methods permit allelic variants selectively to be isolated, with or without contemporaneous detection, and finds particular utility in facilitating the construction of coisogenic cell collections in which the cells differ genotypically by single nucleotide changes targeted to defined loci.

69 Claims, 31 Drawing Sheets

U.S. PATENT DOCUMENTS

| | | | |
|---|---|---|---|
| 5,736,410 | A | 4/1998 | Zarling et al. |
| 5,756,325 | A | 5/1998 | Kmiec |
| 5,760,012 | A | 6/1998 | Kmiec et al. |
| 5,763,240 | A | 6/1998 | Zarling et al. |
| 5,776,744 | A | 7/1998 | Glazer et al. |
| 5,871,984 | A | 2/1999 | Kmiec |
| 5,888,983 | A | 3/1999 | Kmiec et al. |
| 5,891,656 | A | 4/1999 | Zarling et al. |
| 5,912,340 | A | 6/1999 | Kutyavin et al. |
| 5,928,870 | A | 7/1999 | Lapidus et al. |
| 5,929,043 | A | 7/1999 | Dayn |
| 5,948,653 | A | 9/1999 | Pati et al. |
| 5,958,681 | A | 9/1999 | Wetmur et al. |
| 5,965,361 | A | 10/1999 | Kigawa et al. |
| 5,965,427 | A | 10/1999 | Dolgano et al. |
| 5,985,557 | A | 11/1999 | Prudent et al. |
| 6,010,907 | A | 1/2000 | Kmiec et al. |
| 6,043,060 | A | 3/2000 | Imanishi |
| 6,074,853 | A | 6/2000 | Pati et al. |
| 6,107,545 | A | 8/2000 | Mahajan |
| 6,136,601 | A | 10/2000 | Meyer, Jr. et al. |
| 6,150,516 | A | 11/2000 | Brenner et al. |
| 6,159,686 | A | 12/2000 | Kardos et al. |
| 6,174,683 | B1 | 1/2001 | Hahn et al. |
| 6,200,812 | B1 | 3/2001 | Pati et al. |
| 6,245,565 | B1 | 6/2001 | Dayn |
| 6,255,113 | B1 | 7/2001 | Zarling et al. |
| 6,268,490 | B1 | 7/2001 | Imanishi et al. |
| 6,303,304 | B1 | 10/2001 | Shuber et al. |
| 6,303,376 | B1 | 10/2001 | Glazer |
| 6,312,914 | B1 | 11/2001 | Kardos et al. |
| 6,335,164 | B1 | 1/2002 | Kigawa et al. |
| 6,428,964 | B1 | 8/2002 | Shuber |
| 6,664,045 | B1 * | 12/2003 | Hyldig-Nielsen et al. ...... 435/6 |
| 2001/0044107 | A1 | 11/2001 | Zarling et al. |
| 2002/0032530 | A1 | 3/2002 | Pati et al. |
| 2002/0061530 | A1 | 5/2002 | Belotserkovskii et al. |
| 2002/0090361 | A1 | 7/2002 | Zarling et al. |

FOREIGN PATENT DOCUMENTS

| | | |
|---|---|---|
| EP | 0450370 | 9/1991 |
| EP | 0 687 738 | 2/1995 |
| EP | 0799897 | 10/1997 |
| WO | WO87/01730 | 3/1987 |
| WO | WO91/17267 | 11/1991 |
| WO | WO92/08791 | 5/1992 |
| WO | WO93/05177 | 3/1993 |
| WO | WO 93/05178 | 3/1993 |
| WO | WO93/05178 | 3/1993 |
| WO | WO93/22443 | 11/1993 |
| WO | WO94/03639 | 2/1994 |
| WO | WO95/18236 | 6/1995 |
| WO | WO 98/08975 | 3/1998 |
| WO | WO98/08975 | 3/1998 |
| WO | WO 99/14226 | 3/1999 |
| WO | WO 00/50748 | 8/2000 |
| WO | WO 00/56748 | 9/2000 |
| WO | WO 00/66604 | 11/2000 |
| WO | WO 01/73002 | 10/2001 |
| WO | WO 01/92512 | 12/2001 |
| WO | WO 02/10364 | 2/2002 |
| WO | WO 02/10457 | 2/2002 |
| WO | WO 02/077286 | 10/2002 |
| WO | WO 02/079495 | 10/2002 |

OTHER PUBLICATIONS

Lauer et al. "Construction and validation of yeast artifical chromosome contig maps by RecA-assisted restriction endonuclease cleavage", PNAS, vol. 95, Sep. 1998, pp. 11318-11323.*

Pusch et al., "MALDI-TOF Mass Spectrometry-Based SNP Genotyping," *Pharmacogenomics* vol. 3 No. 4: pp. 537-548 (2002).

Faruqi et al., "Peptide nucleic acid-targeted mutagenesis of a chromosomal gene in mouse cells", *Proc. Natl. Acad. Sci. USA*, 96: 1398-1403 (1998).

Norden et al., "Base Orientation of Second DNA in Rec-A-DNA Filaments", *The Journal of Biological Chemistry*, 273(25): 15682-15686 (1998).

European Search Report for EP 02 77 6053, (Dec. 29, 2004).

Anonymous, "Gene Characterization Kits," *Stratagene Catalog*: p. 39 (1988).

Ascenzioni et al., "Mammalian Artificial Chromosomes—Vectors for Somatic Gene Therapy," *Cancer Letters* vol. 118 No. 2: pp. 135-142 (1997).

Baer et al., "Coping with Kinetic and Thermodynamic Barriers: RMCE, and Efficient Strategy for the Targeted Integration of Transgenes," *Current Opinion in Biotechnology* vol. 12: pp. 473-480 (2001).

Belotserkovskii et al., "DNA Hybrids Stabilized by Heterologies," *Biochemistry* vol. 38: pp. 10785-10792 (1999).

Belovsterkovskii et al., "Peptide Nucleic Acid (PNA) Facilitates Multistranded Hybrid Formation between Linear Double-Stranded DNA Targets and RecA Protein-Coated Complementary Single-Stranded DNA Probes," *Biochemistry* vol. 41: pp. 3686-3692 (2002).

Bianco et al., "RecA Protein," *Encyclopedia of Life Sciences*, MacMillan Reference Ltd: pp. 1-11 (Nov. 20, 1998).

Blake et al., "DNA Sequence of Recombinase-Binding Sites Can Determine Xer Site-Specific Recombination Outcome," *Molecular Microbiology* vol. 23 No. 2: pp. 387-398 (1997).

Brenner et al., "In vitro Cloning of Complex Mixtures of DNA on Microbeads: Physical Separation of Differentially Expressed cDNAs," *Proc. Natl. Acad. Sci. USA* vol. 97 No. 4: pp. 16650-16670 (2000).

Brune et al., "Reviews: Forward with BACs; New Tools for Herpesvirus Genomics," *Trends in Genetics* vol. 16 No. 6: pp. 254-259 (2001).

Choi et al., "Construction of a Bacterial Artificial Chromosome Library," *Methods in Molecular Biology* vol. 175: pp. 57-68 (2001).

Cox et al., "recA Protein of *Escherichia coli* Promotes Branch Migration, a Kinetically Distinct Phase of DNA Strand Exchange," *Proc. Natl. Acad. Sci. USA* vol. 78: p. 3433 (1981).

D'Amours et al., "The MRE11 Complex: At the Crossroads of DNA Repair and Checkpoint Signalling," *Nature Reviews* vol. 3: pp. 317-327 (May 2002).

Demidov et al., "Kinetics and Mechanism of the DNA Double Helix Invasion by Pseudocomplementary Peptide Nucleic Acids," *Proc. Natl. Acad. Sci. USA* vol. 99 No. 9: pp. 5953-5958 (Apr. 30, 2002).

Dubertret et al., "Single-Mismatch Detection Using Gold-Quenched Fluorescent Oligonucleotides," *Nature Biotchnology* vol. 19: pp. 365-370 (2001).

Eriksson et al., "PNA-Nucleic Acid Complexes. Structure, Stability and Dynamics," *Quarterly Reviews of Biophysics* vol. 29 No. 4: pp. 369-394 (1996).

Fabb et al., "Yeast Artificial Chromosome Vectors," *Molecular and Cell Biology of Human Gene Disorders Therapeutics* vol. 5: pp. 104-124 (1995).

Fan et al., "Parallel Genotyping of Human SNPs Using Generic High-Density Oligonucleotide Tag Arrays," *Genome Research* vol. 10: pp. 853-860 (2000).

Feng et al., "Site-Specific Chromosomal Integration in Mammalian Cells: Highly Efficient CRE Recombinase-Mediated Cassette Exchange," Journal of Molecular Biology vol. 292: pp. 779-785 (1999).

Ferrin et al., "Selective Cleavage of Human DNA: RecA-Assisted Restriction Endonuclease (RARE) Cleavage," *Science* vol. 254: pp. 1494-1497 (1991).

Ferrin et al., "Sequence-Specific Ligation of DNA Using RecA Protein," *Proc. Natl. Acad. Sci. USA* vol. 95: pp. 2152-2157 (Mar. 1998).

Gamper et al., "Evidence for a Four-Strand Exchange Catalyzed by the RecA Protein," *Biochemistry* vol. 39: pp. 15272-15281 (2000).

Good et al., "Review: Progress in Developing PNA as a Gene-Targeted Drug," *Antisense Nucleic Acid Drug Development* vol. 7 No. 4: pp. 431-437 (1997).

Gorman et al., "Site-Specific Gene Targeting for Gene Expression in Eukaryotes," *Current Opinion in Biotechnology* vol. 11: pp. 455-460 (2000).

Henegariu et al., "Custom Fluorescent-Nucleotide Synthesis as an Alternative Method for Nucleic Acid Labeling," *Nature Biotechnology* vol. 18: pp. 345-348 (2000).

Honigberg et al., "The Pairing Activity of Stable Nucleoprotein Filaments Made from recA Protein, Single-Stranded DNA, and Adenosine 5'-(γ-Thio)triphosphate," *Journal of Biological Chemistry* vol. 260 No. 21: pp. 11845-11851 (Sep. 25, 1985).

Huxley, "Review: Mammalian Artificial Chromosomes: A New Tool for Gene Therapy," *Gene Therapy* vol. 1 No. 1: pp. 7-12 (1994).

Hyrup et al., "Review Article: Peptide Nucleic Acids (PNA): Synthesis, Properties and Potential Applications," *Bioorganic and Medicinal Chemistry* vol. 4 No. 1: pp. 5-23 (1996).

Izvolsky et al., "Sequence-Specific Protection of Duplex DNA Against Restriction and Methylation Enzymes by Pseudocomplementary PNAs," *Biochemistry* vol. 39: pp. 10908-10913 (2000).

Kirk et al., "Single Nucleotide Polymorphism Seeking Long Term Association with Complex Disease," *Nucleic Acids Research* vol. 30 No. 15: pp. 3295-3311 (2002).

Kokoris et al., "High-Throughput SNP Genotyping with the Masscode System," *Molecular Diagnosis* vol. 5 No. 4: pp. 329-340 (2000).

Kricka et al., "Comparison of 5-Hydroxy-2, 3-Dihydrophthalazine-1, 4-Dione and Luminol as Co-Substrates for Detection of Horseradish Peroxidase in Enhanced Chemiluminescent Reactions," *Journal of Immunoassay* vol. 17 No. 1: pp. 67-83 (1996).

Kwok, Pui-Yan, "Methods for Genotyping Single Nucleotide Polymorphisms," *Annu. Rev. Genomics Hum. Genet.* vol. 2: pp. 235-258 (2001).

Lander et al., "The Chipping Forecast," Supplement to *Nature Genetics* vol. 21 No. 1: pp. 1-60 (Jan. 1999).

Langer et al., "A Genetic Screen Identifies Novel Non-Compatible loxP Sites," *Nucleic Acids Research* vol. 30: pp. 3067-3077 (2002).

Larin et al., "Review: Advances in Human Artificial Chromosome Technology," *Trends in Genetics* vol. 18 No. 6: pp. 313-319 (2002).

Lohse et al., "Double Duplex Invasion by Peptide Nucleic Acid: A General Principle for Sequence-Specific Targeting of Double-Stranded DNA," *Proc. Natl. Acad. Sci. USA* vol. 96 No. 21: pp. 11804-11808 (Oct. 12, 1999).

Lundqvist et al., "Influence of Different Luminols on the Characteristics of the Chemiluminescense Reaction in Human Neutrophils," *J. Biolumin. Chemilumin.* vol. 10 No. 6: pp. 353-359 (1995).

Madiraju et al., "Properties of a Mutant *recA*-Encoded Protein Reveal a Possible Role for *Escherichia coli recF*-Encoded Protein in Genetic Recombination," *Proc. Natl. Acad. Sci. USA* vol. 85 No. 18: pp. 6592-6596 (1988).

Nielsen, "Peptide Nucleic Acid: A Versatile Tool in Genetic Diagnostics and Molecular Biology," *Current Opinion in Biotechnology* vol. 12 No. 1: pp. 16-20 (2001).

Nielsen, "Targeting Double Stranded DNA with Peptide Nucleic Acid (PNA)," *Current Medicinal Chemistry* vol. 8 No. 5: pp. 545-550 (2001).

Nielsen, "DNA Analogues with Nonphosphodiester Backbones," *Annu. Rev. Biophys. Biomol. Struct.* vol. 24: pp. 167-183 (1995).

Nielsen et al., "An Introduction to Peptide Nucleic Acid," *Current Issues in Molecular Biology* vol. 1 No. 2: pp. 89-104 (1999).

Nielsen et al., "Peptide Nucleic Acids: On the Road to New Gene Therapeutic Drugs," *Pharmacology and Toxicology* vol. 86: pp. 3-7 (2000).

Peterson et al., "Transgenic Mice Containing a 248-Kb Yeast Artificial Chromosome Carrying the Human Beta-Globin Locus Display Proper Developmental Control of Human Globin Genes," *Proc. Natl. Acad. Sci. USA* vol. 90 No. 16: pp. 7593-7597 (Aug. 15, 1993).

Peterson et al., "Use of Yeast Artificial Chromosomes (Yacs) for Studying Control of Gene Expression: Correct Regulation of the Genes of a Human Beta-Globin Locus YAC Following Transfer to Mouse Erythroleukemia Cell Lines," *Proc. Natl. Acad. Sci. USA* vol. 90 No. 23: pp. 11207-11211 (Dec. 1, 1993).

Roche Diagnostics GmbH, "Classical Structural Genomics," http://www.roche-applied-science.com/usa/3327175B.pdf.

Roche Diagnostics GmbH, "recA Protein," Cat. No. 1 449 567 , Cat. No. 1 449 575, Version 3 (Sep. 1999).

Shah et al., "Multiple *BCR-ABL* Kinase Domain Mutation Confer Polyclonal Resistance to the Tyrosine Kinase Inhibitor Imatinib (STI571) in Chronic Phase and Blast Crisis Chronic Myeloid Leukemia," *Cancer Cell* vol. 2: pp. 117-125 (Aug. 2002).

Shibata et al., "Homologous Genetic Recombination as an Intrinsic Dynamic Property of a DNA Structure Induced by RecA/Rad51-Family Proteins: A Possible Advantage of DNA over RNA as Genomic Material," *Proc. Natl. Acad. Sci. USA* vol. 98 No. 15: pp. 8425-8432 (Jul. 17, 2001).

Shinohara et al., "Rad51/RecA Protein Families and the Associated Proteins in Eukaryotes," *Mutation Research* vol. 435: pp. 13-21 (1999).

Shoemaker et al., "Quantitative Phenotypic Analysis of Yeast Deletion Mutants Using a Highly Parallel Molecular Bar-Coding Strategy," *Nature Genetics* vol. 14 No. 4: pp. 450-456 (1996).

Syvänen, Ann-Christine "Accessing Genetic Variation: Genotyping Single Nucleotide Polymorphisms," *Nature: Reviews* vol. 2: pp. 930-942 (Dec. 2001).

Szybalski, Waclaw, "RecA-Mediated Achilles' Heel Cleavage," *Current Opinion in Biotechnology* vol. 8: pp. 75-81 (1997).

Thorpe et al., "Enhanced Chemiluminescent Reactions Catalyzed by Horseradish Peroxidase," *Methods in Enzymology* vol. 133: pp. 331-353 (1986).

Usher et al., "Targeting of a Chimeric Oligonucleotide to dsDNA for Site-Specific Gene Repair," *FAESB Journal* vol. 15 No. 4: Abstract No. 435.2, p. A518 (Mar. 2001).

Yoshimura et al., "Cloning and Sequence of the Human RecA-like Gene cDNA," *Nucleic Acids Research* vol. 21 No. 7: p. 1665 (1993).

Angov, et al., "The RecA Gene From the Thermophile Thermus Aquaticus YT-1: Cloning, Expression and Characterization", *Journal of Bacteriology*, pp. 1405-1412, Mar. 1994.

Cassuto, et al., "Partial purification of an activity from human cells that promotes homologous pairing and the formation of heteroduplex DNA in the presence of ATP", *Mol. Ge. Genet.*, 208:10 (1987).

Cheng, et al., "Use of Psoralen-modified oligonucleotides to Trap Three-stranded RecA-DNA Complexes and Repair of These Cross-linked Complexes by ABC Excinuclease." *J. Biol. Chem.* 263:15110 (1988).

Cheng, et al., "RecA-Directed Hybridication of Psoralen-Monoadducted DNA oligonucleotides to Duplex Targets," in *Photochemical Probes in Biochemistry* (P.E. Nielsen, ed.), pp. 169-177 (1989).

Chow, et al., "Ionic Inhibition of Formation of RecA Nucleoprotein Networks Blocks Homologous Pairing," *PNAC*, vol. 82, pp. 5646-5650, Sep. 1985.

Cox, et al., "Enzymes of General Recombination" *Ann. Rev. Biochem.* 56:229-262 (1987).

Dervan, Peter B., "Design of Sequence-Specific DNA-Binding Molecules." *Science*, vol. 232 (Apr. 25, 1986), pp. 464-471.

Di Capua, et al., "Characterization of complexes between recA Protein and Duplex DNA by Electron Microscopy," *J. Mol. Biol.* 157:87-103 (1982).

Dreyer, et al., "Sequence=specific cleavage of single-stranded DNA: Oligodeoxynucleotide-EDTA-Fe(II)", *Proc. Natl. Acad. Sci. USA*, 82:968 (1985).

Eisen, et al., "A recombinase from *Drosophila melanogaster* embryos", *Proc. Natl. Acad. Sci. USA*, 85:7481 (1988).

Ferrin, et al., "Long-range mapping of gaps and telomeres with RecA-assisted restriction endonuclease (RARE) cleavage", *Nature Genetics*, vol. 6, pp. 379-383, Apr. 1994.

Francois, et al., "Inhibition of Restriction Endo-nuclease Cleavage via Triple helix Formation by Homopyrimidine Oligonucleotides." *Biochem*, 28:9617-9619 (1989).

Francois, et al., "Sequence-specific recognition and cleavage of duplex DNA via triple-helix formation by oligo-nucleotides covalently linked to a phenanthroline-copper chelate." *Proc. Natl. Acad. Sci. USA* 86:9702-9706 (1989).

Freitag, et al., "Affinity Chromatography of RecA Protein and RecA Nucleoprotein Complexes on RecA Protein-Agarose Columns," *J. Biol. Chem.* 263(36):19525-19534(1988).

Fujisawa, et al., "Sequence of the T4 recombination gene, *uvsX*, and its comparison with that of the *recA* gene of *Escherichia coli*", *Nucleic Acids Res.*, 13:7473 (1985).

Fujiyama, et al., "Cloning and structural analyses of hepatitis.B virus DNAs, subtype adr", *Nucleic Acids Research*, 11:4601 (1983).

Galibert, et al., "Nucleotide sequence of the hepatitis B virus genome (subtype ayw) cloned in *E. coli*", *Nature*, 281:646 (1979).

Ganea, et al., "Characterization of an ATP-Dependent DNA Strand Transferase from Human Cells", *Mol. Cell Biol.*, 7:3124 (1987).

Golub, et al., "Inhibition of RNA polymerase II transcription by oligonucleotide-RecA protein filaments targeted to promoter sequences", *Proc. Natl. Acad. Sci.*, USA, vol. 90, pp. 7186-7190, Aug. 1993.

Golub, et al., "Joints Formed by RecA Protein From Oligonucleotides and Duplex DNA Block Initiation and Elongation of Transcription", *Nucleic Acids Research*, vol. 20, No. 12, pp. 3121-3125, 1992.

Gonda, et al., "By Searching Processively RecA Protein Pairs DNA Molecules That Share a Limited Stretch of Homology", *Cell*, 34:647-654 (1983).

Gonda, et al., "The Mechanism of the Search for Homology Promoted by RecA Protein", *The Journal Of Biological Chemistry*, vol. 261, No. 28, pp. 13087-13096, Oct. 1986.

Griffith, et al., "RecA Protein Rapidly Crystallizes in the Presence of Spermidine: A Variable Step in its Purification and Physical Characterization", *Biochemistry*, 24:158 (1985).

Griffith, et al., "Intercalating Drugs Markedly Affect the Ability to the *E. coli* RecA Protein to Insert Small Primers into Homologous Duplex DNA," *J Call Biochem.* 13E:287(Suppl.)(1989).

Halbrook, et al., "Purification and Characterization of a DNA-pairing and Strand Transfer Activity from Mitotic *Saccharomyces cerevisiae*", *Journal of Biological Chemistry*, 264:21403 (1989).

Hanvey, et al., "Site-specific inhibition of EcoRI restriction/modification enzymes by a DNA triple helix." *Nucleic Acids Res.* 18(1):157 (1989).

Honigberg, et al., "Ability of RecA Protein to Promote a Search for Rare Sequences in Duplex DNA", *PNAC*, vol. 83, pp. 9586-9590, Dec. 1986.

Hsieh, et al., "Pairing of homologous DNA sequences by proteins: evidence for three-stranded DNA," *Genes & Development*, 4:1951 (1990).

Hsieh, et al., "Formation of Joint DNA Molecules by Two Eukaryotic Strand Exchange Proteins Does Not Require Melting of a DNA Duplex", *J. Biol. Chem.*, 264:5089 (1989).

Hsieh, et al., "Partial Purification and Characterization of a Recombinase from Human Cells", *Cell*, 44:885 (1986).

Hsieh, et al., "The synapsis event in the homologous pairing of DNAs: RecA recognizes and pairs less than one helical repeat of DNA", *Proc. Natl. Acad. Sci. USA*, 89:6492-6496 (1992).

Jayasena, et al., "Compliment Stabilized D-loop RecA-catalyzed Stable Pairing of Linear DNA Molecules at Internal Sites", *J. Mol. Biol.*, pp. 1015-1024 (1993).

Kato, et al., "RecA Protein From an Extremely Thermophilic Bacterium, Thermus Thermophilus HB8", *J. Biochem.* vol. 114, pp. 926-929, 1993.

Kawashima, et al., "Functional Domains of *Escherichia coli* RecA Protein Deduced From the Mutational Sites in the Gene", *Mol. Gen. Genet.*, vol. 193, pp. 288-292, 1984.

Kenne, et al., "A DNA-recombinogenic activity in human cells", *Nucleic Acids Research*, 12:3057 (1984).

Kido, et al., "*Escherichia coli* RecA Protein Modified with a Nuclear Location Signal Binds to Chromosones in Living Mammalian Cells," *Experimental Cell Res.* 198:107-114 (1992).

Kirkpatrick, et al., "RecA Protein Promotes Rapid RNA-DNA Hybridization in Heterogeneous RNA Mixtures", *Nucleic Acids Research* pp. 4347-4353.

Kirkpatrick, et al., "RNA-DNA Hybridization Promoted by *E.coli* RecA Protein", *Nucleic Acid Research*, vol. 20, No. 16, pp. 4339-4346, (1992).

Kmiec, et al., "Homologous Pairing of DNA Molecules Promoted by a Protein from Ustilago", *Cell*, vol. 29 pp. 367-374 (1982).

Kmiec, et al., "Synapsis Promoted by Ustilago Rec1 Protein", *Cell*, vol. 36, pp. 593-598, Mar. 1984.

Kmiec, et al., "Homologous Pairing of DNA Molecules by Ustilago Rec1 Is Promoted by Sequences of Z-DNA", *Cell*, 29:367-374 (1986).

Kmiec, et al., "Homologous Pairing Promoted by Ustilago Protein", *Cold Spring Harbor Symposia on Quantitative Biology*, vol. XLIX, 675-679, (1984).

Knight et al., "Tyrosine 264 in the recA Protein from *Escherichia coli* Is the Site of Modification by Photoaffinity Label 8-Azidoadensine", *J. Biol. Chem.* 260 (18):10185-91, Aug. 25, 1985.

Kolodner, et al., "Purification and characterization of an activity from *Saccharomyces cerevisiae* that catalyzes homologous pairing and strand exchange", *Proc. Natl. Acad. Sci. USA*, 84:5560 (1987).

Koob, et al., "RecA-AC: single-site cleavage of plasmids and chromosomes at any predetermined restriction site", *Nucleic Acids Research*, vol. 20, No. 21, pp. 5831-5836, 1992.

Kowalczykowski, Stephen C., "Biochemistry of Genetic Recombination: Energetics and Mechanism of DNA Strand Exchange," *Annu. Rev. Biophys. Chem.*, vol. 20, pp. 539-575 (1991).

Kowalczykowski, et al., "DNA-strand exchange promoted by RecA protein in the absence of ATP: Impliations for the mechanism of energy transduction in protein-promoted nucleic acid transactions", *Proc. Natl. Acad. Sci. USA*, vol. 92, pp. 3478-3482.

Kuramitsu, et al., "A Large-Scale Preparation and Some Physiochemical Properties of RecA Protein", *J. Biochem*, vol. 90, pp. 1033-1045, 1981.

Lawrence, et al., "A Fluorescence In Situ Hybridization Approach for Gene Mapping and the Study of Nuclear Organization", *Genome Analysis*, 1:1 (1990).

Leahy, et al., "Topography of the Interaction of recA Protein with Single-stranded Deoxyoligonucleotides," *J. Biol. Chem.*, 261:6954 (1986).

Lovett, et al.,, "Purification of a RecA Protein Analogue from *Bacillus subtilis*," *J. Biol. Chem.*, vol. 260, No. 6 pp. 3305-3313 (1985).

Lowenhaupt, et al., "*Drosophila melanogaster* Strand Transferase", *J. Biol. Chem.*, 264:20568 (1989).

Maher III, et al., "Inhibition of DNA Binding Proteins by Oligonucleotide-Directed Triple Helix Formation," *Science* 245:725-730 (1989).

Makino, et al., "Monoclonal Antibodies with Specific Effects on Partial Activities of recA Protein of *Escherichia coli*", *J. Biol. Chem.*, 260, 15402, 1985.

McCarthy, et al., "Sensitive homologous recombination strand-transfer assay: Partial purification of a *Drosophila melanogaster* enzyme and detection of sequence effects on the strand-transfer activity of RecA protein", *Proc. Natl. Acad. Sci. USA*, 85:5854 (1988).

McEntee, et al., "Binding of the recA Protein of *Escherichia coli* to Single- and Double-Stranded DNA", *J. Biol. Chem.*, 256:8835-8844 (1981).

Menetski, et al., "Enhancement of *Escherichia coli* RecA Protein Enzymatic Function by dATP," *Biochem.* 28:5871-5881 (1989).

Moore, et al., "Purification and Characterization of a Protein from Human Cells Which Promotes Homologous Pairing of DNA", *J. Biol. Chem.*, 19:11108-11117 (1990).

Moreau, et al., "Rec-A Protein-promoted Cleavage of Lex-A Repressor in the Presence of ADP and Structural Analogues of Inorganic Phosphate, the Fluoride Complexes of Aluminum and Beryllium", *J. Biol. Chem.*, 264:2302-2306 (1989).

Morrical, et al., "Stabilization of recA Protein-ssDNA Complexes by the Single-Stranded DNA Binding Protein of *Escherichia coli*", *Biochemistry*, 29:837 (1990).

Moser, et al., "Sequence-Specific Cleavage of Double helical DNA by Triple Helix Formation", *Science* 238:645-650 (1987).

Podyminogin, et al., "Sequence-Specific Covalent Modification of DNA by Cross-Linking Oligonucleotides. Catalysis by RecA and Implication for the Mechanism of Synaptic Joint Formation", *Biochemistry*, vol. 34, pp. 13098-13108, 1995.

Radding, et al., "Homologous Pairing and Strand Exchange in Genetic Recombination." *Ann. Rev. Genet.* 16:405 (1983) 25:1990.

Radding, Charles M., "Helical RecA Nucleoprotein Filaments Mediate Homologous Pairing and Strand Exchange", *Biochem. Biophys. Acta.*, 1008 (1989), pp. 131-145.

Radding, Charles M., "Helical Interactions in Homologous Pairing and Strand Exchange Driven by RecA Protein", *The Journal of Biological Chemistry*, vol. 266, No. 9, pp. 5355-5358, Mar. 1991.

Revet, et al., "Homologous DNA Targeting with RecA Protein-coated Short DNA Probes with Electron Microscope Mapping on Linear Duplex Molecules", *J. Mol. Biol.*, vol. 232, pp. 779-791, 1993.

Rigas, et al., "Rapid Plasmid Library Screening Using RecA Coated Biotinylated Probes", *PNAC*, vol. 83, pp. 9591-9595, Dec. 1986.

Roca, et al., "The RecA Protein: Structure and Function," *Crit. Rev. Biochem. Molec. Biol.* 25:415 (1990).

Shibata, et al., "Purified *Escherichia coli* recA Protein catalyzed homologous pairing of superhelical DNA and single-stranded fragments." *Proc. Natl. Acad. Sci. USA* 76:1638 (1979).

Shibata, et al., "Purification of RecA Protein From *Escherichia coli*", *Method in Enzymology*, vol. 100, pp. 197-209.

Shibata, T., et al., "Homologous Pairing in Genetic Recombination", *J. Bio. Chem.*, 256:7557 (1981).

Shinohara, et al., "Cloning of Human, Mouse and Fission Yeast Recombination Genes Homologous to RAD51 and RecA", *Nature Genetics*, vol. 4, pp. 239-243, Jul. 1993.

Sluka, et al., "Synthesis of a Sequence-Specific DNA-Cleaving Peptide", *Science*, 238:1129 (1987).

Sugino, et al., "ATP-independent DNA strand transfer catalyzed by protein(s) from meiotic cells of the yeast *Saccharomyces cerevisiae*", *Proc. Natl. Acad. Sci. USA*, 85:3683, (1988).

Teintze, et al., RecA Assisted Rapid Enrichment of Specific Clones From Model DNA Libraries, *Biochemical and Biophysical Research Communications*, vol. 211, No. 3, pp. 804-811, Jun. 26, 1995.

Tsang, et al., "Networks of DNA and RecA Protein Are Intermediates in Homologous Pairing", *Biochemistry*, vol. 24, pp. 3226-3232, 1985.

\* cited by examiner

Oligonucleotide Sequence of the Kan⁻Target

```
  1 CAGGGGATCA AGATCTGATC AAGAGACAGG ATGAGGATCG TTTCGCATGA
 51 TTGAACAAGA TGGATTGCAC GCAGGTTCTC CGGCCGCTTG GGTGGAGAGG
101 CTATTCGGCT ATGACTGGGC ACAACAGACA ATCGGCTGCT CTGATGCCGC
151 CGTGTTCCGG CTGTCAGCGC AGGGGCGCCC GGTTCTTTTT GTCAAGACCG
201 ACCTGTCCGG TGCCCTGAAT GAACTGCAGG ACGAGGCAGC GCGGCTATCG
251 TGGCTGGCCA CGACGGGCGT TCCTTGCGCA GCTGTGCTCG ACGTTGTCAC
301 TGAAGC
```

FIG. 13

Oligonucleotide Sequence of the Hyg⁻Target

```
  1 cgctgagata ggtgcctcac tgattaagca ttggtaactg tcagaccaag
 51 tttactcata tatactttag attgatttaa aacttcattt ttaatttaaa
101 aggatctagg tgaagatcct ttttgataat ctcatgacca aaatccctta
151 acgtgagttt tcgttccact gagcgtcaga ccccgtagaa aagatcaaag
201 gatcttcttg agatcctttt tttctgcgcg taatctgctg cttgcaaaca
251 aaaaaaccac cgctaccagc ggtggtttgt ttgccggatc aagagctacc
301 aactcttttt ccgaaggtaa ctggcttcag cagagcgcag ataccaaata
351 ctgtccttct agtgtagccg tagttaggcc accacttcaa gaactctgta
401 gcaccgccta catacctcgc tctgctaatc ctgttaccag tggctgctgc
451 cagtggcgat aagtcgtgtc ttaccggg
```

FIG. 15

DETECTION OF HUMAN β TUBULIN SEQUENCE

| βTUBwt dDLoop | | | | |
|---|---|---|---|---|
| βTUB PCR (44 ng) | + | + | + | + |
| RecA | + | - | + | + |
| INCOMING OLIGO | + | + | + | - |
| ANNEALING OLIGO | + | + | - | + |

DETECTION OF HUMAN β TUBULIN SEQUENCE

| EtBr post-stain | | | | |
|---|---|---|---|---|
| βTUB PCR (44 ng) | + | + | + | + |
| RecA | + | - | + | + |
| INCOMING OLIGO | + | + | + | - |
| ANNEALING OLIGO | + | + | - | + |

SEQUENCE SPECIFIC SEPARATION OF PLASMID CLONES

| Kan/Tet | Colonies (PreSep) | | Colonies (PostSep) | |
|---|---|---|---|---|
| | Kan | Tet | Kan | Tet |
| 1:0 | TNTC | 0 | >4000 | 0 |
| 1:10 | TNTC | TNTC | 2543 | 0 |
| 1:100 | 2060 | TNTC | 282 | 0 |
| 1:1000 | 1132 | TNTC | 30 | 0 |
| 1:10,000 | 280 | TNTC | 2 | 0 |
| 1:100,000 | 17 | TNTC | 1 | 0 |
| 0:1 | 0 | TNTC | 0 | 0 |
| 1:10 (No RecA) | TNTC | TNTC | 0 | 0 |

FIG. 28

MISMATCH SPECIFIC DNA SEPARATION

| Target DNA | | Supercoiled Plasmid | | | | | | Relaxed |
|---|---|---|---|---|---|---|---|---|
| Target | % KAN CNV | Colonies (presep) | | % Kan CNV (presep) | Colonies (postsep) | | % Kan CNV | % Kan CNV |
| Plasmids | (SNaP) | Kan | Amp | Kan/Amp | Kan | Amp | Kan/Amp | Kan/Amp |
| pKAN+ (tat) | - | 1124 | 1188 | 95% | 48 | 63 | 76% | 0% |
| pKAN- (tag) | - | 0 | 448 | 0% | 0 | 0 | 0% | 0% |
| CNV B1 (tag-tac) | 5% | 60 | 570 | 10% | 53 | 128 | 42% | >90% |
| CNV D3 (tag-tac) | 69% | 363 | 437 | 83% | 164 | 183 | 90% | >90% |
| CNV D5 (tag-tac) | 10% | 90 | 520 | 17% | 28 | 38 | 74% | >90% |

FIG. 29

POLYMORPHISM DETECTION AND SEPARATION

CROSS-REFERENCE TO RELATED APPLICATIONS

This application is a continuation-in-part of international application PCT/US02/09691, filed Mar. 27, 2002, and a continuation-in-part of U.S. provisional application Ser. No. 60/325,828, filed Sep. 28, 2001, the disclosures of which are incorporated herein by reference in their entireties.

BACKGROUND OF THE INVENTION

A wide variety of methods have recently been developed to detect and characterize single nucleotide polymorphisms (SNPs) within complex genomes.

Each of these methods strives to satisfy a number of oft-competing needs: the need to identify the target locus uniquely within a complex sample (target specificity) with the need to distinguish among the polymorphic variants of the specified target (allelic selectivity); the need to provide specificity and selectivity at a single target with the need to query a large number of targets concurrently in a single multiplexed reaction; the need to provide a detectable signal from a small genomic or transcriptional sample with the need to avoid target amplification approaches that introduce spurious mutations; the need to query a duplex sample with reactions—such as hybridization, primer extension, and template-driven ligation—that require single-stranded substrates.

Current approaches to SNP detection and characterization address these problems using a variety of reaction schemes, with varying degrees of success. Reviewed in Kirk et al., *Nucl. Acids Res.* 30:3295-3311 (2002); Syvanen, *Nature Reviews, Genetics* 2:930-942 (2001); Kwok, *Annu. Rev. Genomics Hum. Genet.* 2:235-258 (2001).

Recently, it has become possible to target single nucleotide changes directly into long pieces of genomic DNA, including YACs, BACs, and even intact cellular chromosomes using sequence-altering oligonucleotides. See WO 01/73002; WO 01/92512; and WO 02/10364. Although the frequency of targeted change is appreciable, it is still less than 100%, and there is thus a need for methods that permit the engineered variants to be separated from nucleic acids that differ by as few as one nucleotide therefrom. Yet none of the common techniques for SNP detection readily permits the direct purification or isolation of the variants so detected, particularly in their full length, unamplified, double-stranded form.

Methods for isolating DNA analytes in double-stranded form are known. The methods use RecA protein, a critical component in the cellular process of homologous recombination.

In the presence of ATP, RecA protein polymerizes on single-stranded DNA to form a right-handed helical nucleoprotein filament that is capable of invading duplex DNA in a sequence-independent fashion. Thereafter, in a process as yet incompletely understood, the RecA coated nucleoprotein filament searches along the duplex for homologous sequence. Once homologous sequence is located, RecA mediates further ATP-dependent reactions necessary to effect strand exchange and recombination. In the presence of a non-hydrolyzable ATP analogue, such as ATP-γS, the process halts after regions of homology have been found, with the nucleoprotein filament bound to the duplex in a joint structure commonly termed a displacement loop ("D-loop"). The strand of the duplex displaced by the RecA filament is available to bind a second single-stranded nucleic acid; the four-stranded joint structure so formed is termed a double D-loop ("double D-loop", "dDloop").

U.S. Pat. No. 5,670,316 describes methods of isolating DNA duplexes by using *E. coli* RecA protein to anchor complementary polynucleotide probes within a double displacement loop formed at a desired target sequence; at least one of the probes has a moiety that permits the subsequent specific capture and isolation of the double D-loop-containing duplex.

The RecA filament homology search is permissive of mismatches, however; the in vivo manifestation of this phenomenon is the well known tolerance of homologous recombination for the presence of heterologous sequence.

Accordingly, the methods of isolation described in U.S. Pat. No. 5,670,316 are said to tolerate up to 30% mismatch between probes and target duplex. Analogous dDloop isolation methods described in WO 02/10457 are said to tolerate 50% mismatch as between probe and target, although no more than 30% sequence mismatch is said to be preferred.

Although RecA-mediated purification procedures permit separation of double-stranded targets, tolerance of mismatches between probe and target precludes the separation and isolation of polymorphic variants that differ by a single nucleotide.

Accordingly, there remains a need in the art for genotyping methods that permit single nucleotide polymorphisms readily to be detected within a complex genome, and that permit specific polymorphic variants so detected to be isolated in double-stranded form from variants that may differ by as few as one nucleotide therefrom.

SUMMARY OF THE INVENTION

The present invention solves these and other needs in the art by providing methods, compositions, and kits for distinguishing the presence of one or more double-stranded nucleic acid targets present within a sample of nucleic acids from variants that can differ by as few as one nucleotide therefrom, and methods that optionally permit such targets selectively to be separated and purified from such samples.

The methods are readily multiplexed, permitting a large number of loci to be screened within a single sample, may be adapted to a variety of existing detection systems, and permit target amplification without PCR, increasing fidelity. The ability to separate desired double stranded targets with allelic selectivity, with or without contemporaneous detection, offers significant advantages over current genotyping methods.

The invention is based in part upon the development of reaction conditions under which the paradigmatic mismatch tolerance of RecA-mediated D-loop formation does not act to prohibit single nucleotide mismatch discrimination. Preferred reaction conditions can differ depending upon the topological state of the target.

In a first aspect, therefore, the invention provides a method for distinguishing the presence of a nonsupercoiled target nucleic acid from the presence of nonsupercoiled target variants within a sample of nucleic acids, the variants differing from the target by as few as one nucleotide within a common target query region.

The method comprises using a recombinase to mediate formation of at least one deproteinization-stable double D-loop in the query region of the target, under conditions that favor double D-loop formation at the target query region over formation at variants that differ from the target by as few as one nucleotide therefrom, and then distinguishing the degree of formation of double D loops that are stable to deproteinization. A greater degree of formation distinguishes the presence of target from that of variants.

In typical embodiments, the double D-loop formation conditions comprise contacting the nucleic acid sample with a first oligonucleotide and a second oligonucleotide (hereinafter also denominated "incoming" and "annealing" oligonucleotides, respectively). The first oligonucleotide may be contacted to sample before the second oligonucleotide or contemporaneously therewith.

The first oligonucleotide includes a complementarity region that is perfectly complementary in sequence to a first strand of the target across the entirety of the target query region. The second oligonucleotide includes a complementarity region that is perfectly complementary in sequence to a second strand of the target across at least a portion of the target query region. And at least one of the first or second oligonucleotide complementarity regions is imperfectly complementary to the respective first or second strands of the query region of each of the target variants desired selectively to be discriminated from target.

The first oligonucleotide is bound by a recombinase. The second oligonucleotide comprises base modifications and does not substantially bind the recombinase. And at least one of the first and second oligonucleotides is distinguishably detectable.

In typical embodiments, the first oligonucleotide is no more than about 100 nucleotides in total length, typically no more than 50 nucleotides in length; the first oligonucleotide complementarity region is thus usually no more than 100 nucleotides in length, typically no more than 50 nucleotides in length, and can be smaller.

The second oligonucleotide base modifications can be selected from the group consisting of LNA bases, PNA bases, RNA bases, and 2'-OMe bases. Typically, the second oligonucleotide includes at least 30% modified bases, often at least 50% modified bases, and be include at least 75% modified bases or more.

The second oligonucleotide, in certain embodiments, is no more than 50 nt in total length, typically no more than 25 nt in total length, and at times as short as 20 nt, and even 15-16 nt in total length. The second second oligonucleotide complementarity region is frequently no more than 50 nucleotides in length, 25 nt in length, and in certain embodiments is as short as 15-16 nt in length.

Typically, the first and second oligonucleotide complementarity regions overlap by no more than 25 nt, often by no more than 15 nt.

Usefully, at least one of the first and second oligonucleotides includes at least one detectabe label. In certain embodiments, the label is selected from the group consisting of a radionuclide, a fluorophore, a fluorescence resonance energy transfer tandem fluorophore, a fluorescence resonance energy transfer donor, a fluorescence resonance energy transfer acceptor, a mass tag, an enzyme, a genotypic label ("bar code tag"), or a hapten, with fluorophores and genotypic bar code tags having particular utility.

The contacting step may be performed, in certain embodiments, at a temperature of at least about 37° C., 45° C., 50° C., and even at least about 55° C.

The methods of the present invention may further comprise the step, after forming and before distinguishing the degree of formation of the double D loops, of deproteinizing the nucleic acids of said sample.

Deproteinization may be performed, for example, at a temperature of at least 37° C., and for no more than about 10 minutes.

The double D loops may usefully be stable for a time following deproteinization sufficient to permit detectable separation of target from target variants.

For example, in certain embodiments the double D loops are stable for at least 2 hours at 4° C. following deproteinization, at least 4 hours at 4° C. following deproteinization, and even for at least 30 minutes at 37° C. following deproteinization.

The nonsupercoiled double-stranded target in the methods of this aspect of the present invention may be linear duplex DNA, a covalently closed circle, or a nicked circle, among others.

The target may be within a nucleic acid preparation lacking vector sequences or, in the alternative or in addition, be within a nucleic acid preparation having vector sequences.

The target may, for example, be within an artificial chromosome, and the target query region may usefully be flanked in such artificial chromosome by recognition sites for a site-specific recombinase.

The nucleic acids of the sample to be queried may be pooled from a plurality of individuals or drawn from a single individual.

In a series of embodiments, the nucleic acid sample includes at least one variant that differs from the target by no more than one nucleotide in the query region. The variants that are concurrently present may be naturally-occurring allelic variants of the target, somatically mutated variants of the target, or recombinantly-engineered variants of the target.

The method may further comprise the step, after deproteinizing and before distinguishing the double D loops, of separating the nucleic acids that have double D loops from nucleic acids lacking double D loops. Usefully, at least one of the first and second oligonucleotides is tethered to a solid support or includes a capture moiety, such as biotin.

The method may further comprise the step, after double D loop formation, of extending by polymerase either or both of the first or second oligonucleotides, either by a single base, or by multiple bases, the latter permitting allele-specific amplification of the target query region. Amplification may be isothermal or thermal cycling.

The method may further comprise the step, after double D loop formation, of selectively cleaving either the target or variants thereof.

The method may further comprising the step of quantifying the absolute or relative abundance of target.

In a second aspect, the invention provides a method of distinguishing the presence of a supercoiled target nucleic acid from the presence of supercoiled target variants within a sample of nucleic acids, the variants differing from the target by as few as one nucleotide within a common target query region.

The method comprises using a recombinase to mediate formation of at least one deproteinization-stable single D-loop or double D-loop in the query region of the target, under conditions that favor formation at the target query region over formation at variants that differ from the target by as few as one nucleotide therefrom, and then distinguishing the degree of formation of single D-loops or double-D loops that are stable to deproteinization, a greater degree of formation distinguishing the presence of target from that of variants.

Formation conditions in this aspect of the invention typically comprise contacting the sample with at least a first oligonucleotide to form at least a single D-loop at the target query region.

The first oligonucleotide is bound by a recombinase, and includes a complementarity region that is (i) perfectly complementary in sequence to a first strand of the target across the entirety of the target query region and (ii) imperfectly complementary to a first strand of the query region of each of the target variants desired to be distinguished.

The method may further comprise contacting the sample with a second, "annealing", oligonucleotide to effect formation of a double D-loop at the target query region. The second oligonucleotide comprises base modifications, does not substantially bind recombinase, and includes a complementarity region that is perfectly complementary in sequence to a second strand of the target across at least a portion of the target query region.

In these latter, two oligonucleotide, double D-loop embodiments, at least one of the first and second oligonucleotide complementarity regions is imperfectly complementary to a respective strand of the query region of each of the target variants, and the second oligonucleotide is typically distinguishably detectable.

In certain embodiments, the method may further comprise contacting the sample with a third oligonucleotide. The third oligonucleotide comprises base modifications and does not substantially bind the recombinase. It includes a complementarity region that is perfectly complementary in sequence to at least a portion of the second strand of the query region of a target variant as to which the target is desired to be discriminated, and that is imperfectly complementary in sequence to the complementarity region of said first oligonucleotide.

In another aspect, the invention provides methods of distinguishably detecting the presence of a plurality of nonsupercoiled targets within a sample of nucleic acids with selectivity sufficient to distinguish each of the plurality of targets from variants that respectively differ by as few as one nucleotide therefrom at a query region that is common therebetween.

The method comprises using a recombinase to mediate formation, separately for each of the plurality of targets desired to be detected, of at least one deproteinization-stable double D loop in the target's query region, under conditions that favor double D loop formation at the target query region over formation at variants that differ from the target by as few as one nucleotide therefrom, each target's double D-loop being distinguishably detectable from all others of the double D-loops formed in said sample; and then distinguishably detecting each of the stable double-D loops so formed.

In certain embodiments, the formation conditions comprise contacting the sample, for each of the plurality of targets desired to be detected, with a first oligonucleotide and a second oligonucleotide: the first oligonucleotide includes a complementarity region that is perfectly complementary in sequence to a first strand of its respective target across the entirety of the target query region; the second oligonucleotide includes a complementarity region that is perfectly complementary in sequence to a second strand of the same target across at least a portion of the target query region; and either or both of the oligonucleotide regions is imperfectly complementary in sequence to respective first and second strands of the query region of each of the other targets desired discriminably to be detected.

In these embodiments, the first oligonucleotide is bound by a recombinase and the second oligonucleotide comprises base modifications and does not substantially bind said recombinase, and at least one of the oligonucleotides is distinguishable from the first and second oligonucleotides used to detect each of the others of the plurality of targets desired to be detected.

In another aspect, the invention provides a method of distinguishably detecting the presence of a plurality of supercoiled targets within a sample of nucleic acids, with selectivity sufficient to distinguish each of the plurality of targets from variants that respectively differ by as few as one nucleotide therefrom at a query region that is common therebetween.

The method comprises using a recombinase to mediate formation, separately for each of the plurality of targets desired to be detected, of at least one deproteinization-stable single- or double-D loop in the target's query region, under conditions that favor single- or double-D loop formation at the target query region over formation at variants that differ from the target by as few as one nucleotide therefrom, each target's single- or double D-loop being distinguishably detectable from all others of the D-loops formed in the sample; and then distinguishably detecting each of the stable double-D loops so formed.

The formation conditions may usefully comprise contacting the sample, for each of the plurality of targets desired to be detected, with a first oligonucleotide, wherein the first oligonucleotide includes a complementarity region that is perfectly complementary in sequence to a first strand of its respective target across the entirety of the target query region and imperfectly complementary in sequence to a first strand of the query region of each of the other targets desired discriminably to be detected, wherein the first oligonucleotide is bound by a recombinase and is distinguishable from the first oligonucleotide used to detect each of the others of the plurality of targets desired to be detected.

In other embodiments, the method further comprises contacting the sample, for each of the plurality of targets desired to be detected, with a second oligonucleotide, wherein the second oligonucleotide includes a complementarity region that is perfectly complementary in sequence to a second strand of the target across at least a portion of the target query region, wherein at least one of the first and second oligonucleotide complementarity regions is imperfectly complementary to the respective strand of the query region of each of the target variants, wherein the second oligonucleotide comprises base modifications and does not substantially bind said recombinase, and wherein the second oligonucleotide is distinguishably detectable.

Usefully, the methods of distinguishably detecting the presence of a plurality of supercoiled targets within a sample of nucleic acids, with selectivity sufficient to distinguish each of the plurality of targets from variants that respectively differ by as few as one nucleotide therefrom at a query region that is common therebetween, may further comprise quantifying the relative abundance of each of said targets.

In certain embodiments, at least 10, 50, and as many as 100-10,000 targets are discriminably detected, either seriatim or concurrently. Usefully, concurrent detection is by microarray hybridization.

In another aspect, the invention provides methods of separating a double-stranded nucleic acid target from other non-supercoiled nucleic acids present within a sample of nucleic acids, with selectivity sufficient to separate the target from variants that differ from the target by as few as one nucleotide within a common target query region.

The method comprises using a recombinase to mediate formation of at least one deproteinization-stable double D loop in the query region of the target, under conditions that favor double D loop formation at the target query region over formation at variants that differ from the target by as few as one nucleotide thereof; and then separating nucleic acids having deproteinization-stable double D loops from other nucleic acids present within the sample.

Typical formation conditions comprise contacting the sample with a first oligonucleotide and a second oligonucleotide, wherein the first oligonucleotide includes a complementarity region that is perfectly complementary in sequence to a first strand of the target across the entirety of the target query region, the second oligonucleotide includes a complementarity region that is perfectly complementary in sequence to a second strand of the target across at least a portion of the target query region, and at least one of the first or second oligonucleotide complementarity regions is imperfectly complementary to the respective first or second strands of the query region of each of said target variants. The first oligonucleotide is bound by a recombinase and the second oligonucleotide comprises base modifications and does not substantially bind said recombinase.

In some embodiments, at least one of the first and second oligonucleotides includes a capture moiety and the nucleic acids having deproteinization-stable double D loops are separated from other nucleic acids present within the sample by capture of the moiety. In certain of these embodiments, the moiety is captured to a solid substrate, such as a magnetic bead.

The method can effect purification of the target, with single nucleotide selectivity, of at least 10-fold, and even at least 100-fold, 1000-fold, to 10,000-fold to $10^6$-fold or more.

In another aspect, the invention provides nucleic acid compositions characterized by the presence of at least one deproteinized double D loop at a query region within a nucleic acid target. The deproteinized double D-loop includes a first and a second oligonucleotide, wherein the first oligonucleotide includes a complementarity region that is perfectly complementary in sequence to a first strand of the target across the entirety of the target query region, wherein the second oligonucleotide includes a complementarity region that is perfectly complementary in sequence to a second strand of the target across at least a portion of the target query region, wherein the first oligonucleotide is bound by a recombinase, wherein said second oligonucleotide comprises base modifications and does not substantially bind said recombinase, and wherein at least one of the first and second oligonucleotides is distinguishably detectable.

In some embodiments, the composition further comprises at least one variant that differs from the target by as few as one nucleotide within a query region that is common therebetween, wherein the query region of each of the at least one target variants lacks a double D loop.

In another aspect, the invention provides nucleic acid compositions characterized by the presence of a plurality of deproteinized double D-loops, each of the plurality formed at a query region within a respective nucleic acid target, wherein each double D-loop includes a first and a second oligonucleotide, wherein the first oligonucleotide includes a complementarity region that is perfectly complementary in sequence to a first strand of the target across the entirety of the target query region, wherein the second oligonucleotide includes a complementarity region that is perfectly complementary in sequence to a second strand of the target across at least a portion of the target query region, wherein the first oligonucleotide is bound by a recombinase, and wherein the second oligonucleotide comprises base modifications and does not substantially bind said recombinase.

At least two of the plurality of targets may differ in sequence by 1-10 nucleotides as between their respective query regions, and in some embodiments, at least two of said plurality of targets differ in sequence by exactly 1 nucleotide as between their respective query regions.

The composition may include at least 10, 100, 1000, even 10,000 targets, either supercoiled or nonsupercoiled.

In another aspect, the invention provides a kit for distinguishing the presence of a target nucleic acid from the presence of target variants within a sample of nucleic acids, the variants differing from the target by as few as one nucleotide within a common target query region.

The kit comprises a first oligonucleotide, a second oligonucleotide, and a RecA-like recombinase.

The first oligonucleotide includes a complementarity region that is perfectly complementary in sequence to a first strand of the target across the entirety of the target query region. The second oligonucleotide includes a complementarity region that is perfectly complementary in sequence to a second strand of the target across at least a portion of the target query region. And at least one of the first or second oligonucleotide complementarity regions is imperfectly complementary to the respective first or second strands of the query region of each of the target variants.

The first oligonucleotide is capable of being bound by a recombinase and the second oligonucleotide comprises base modifications and is incapable of substantially binding said recombinase. At least one of the first and second oligonucleotides is distinguishably detectable.

In some embodiments, the first oligonucleotide and RecA are combined in a single composition. In typical embodiments, at least one of the first and second oligonucleotides is detectably labeled.

In another aspect, the invention provides a kit for separately distinguishing the presence of a plurality of targets within a nucleic acid sample, with selectivity sufficient to distinguish each of the plurality of targets from variants that respectively differ by as few as one nucleotide therefrom at a query region that is common therebetween.

The kit comprises a RecA-like recombinase, and, for each target desired to be separately to be distinguished, a pair of first and second oligonucleotides.

The first oligonucleotide of the pair includes a complementarity region that is perfectly complementary in sequence to a first strand of its respective target across the entirety of the target query region. The second oligonucleotide of each pair includes a complementarity region that is perfectly complementary in sequence to a second strand of the same target across at least a portion of the target query region. Either or both of the oligonucleotide complementarity regions is imperfectly complementary in sequence to respective first and second strands of the query region of each of the other targets desired discriminably to be detected.

The first oligonucleotide is capable of binding a recA-like recombinase and the second oligonucleotide comprises base modifications and is incapable of substantially binding a RecA-like recombinase, and at least one of The oligonucleotides is distinguishable from the first and second oligonucleotides used to detect each of the others of the plurality of targets desired to be detected.

In some embodiments, each of said first oligonucleotides is combined with RecA, either in a separate composition, or in a single, common, composition.

Typically, at least one of the first and second oligonucleotides of each target pair is detectably labeled, the label of each target pair being distinguishable from that of each other target pair. Usefully, the label may be a fluorescent label or a genotypic label.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIG. 13 shows the oligonucleotide sequence [SEQ ID NO: 37] of the Kan⁻ PCR product used as a target for double D-loop formation in embodiments of the present invention;

FIG. 15. shows the oligonucleotide sequence of the Hyg⁻ PCR product [SEQ ID NO: 115] used as a target for double D-loop formation and as non-specific competitor DNA in Example 12;

FIG. 28 is a table summarizing data demonstrating gene-specific separation of plasmid clones;

FIG. 29 is a table summarizing data demonstrating variant-selective DNA separation.

DETAILED DESCRIPTION

Figure 1:
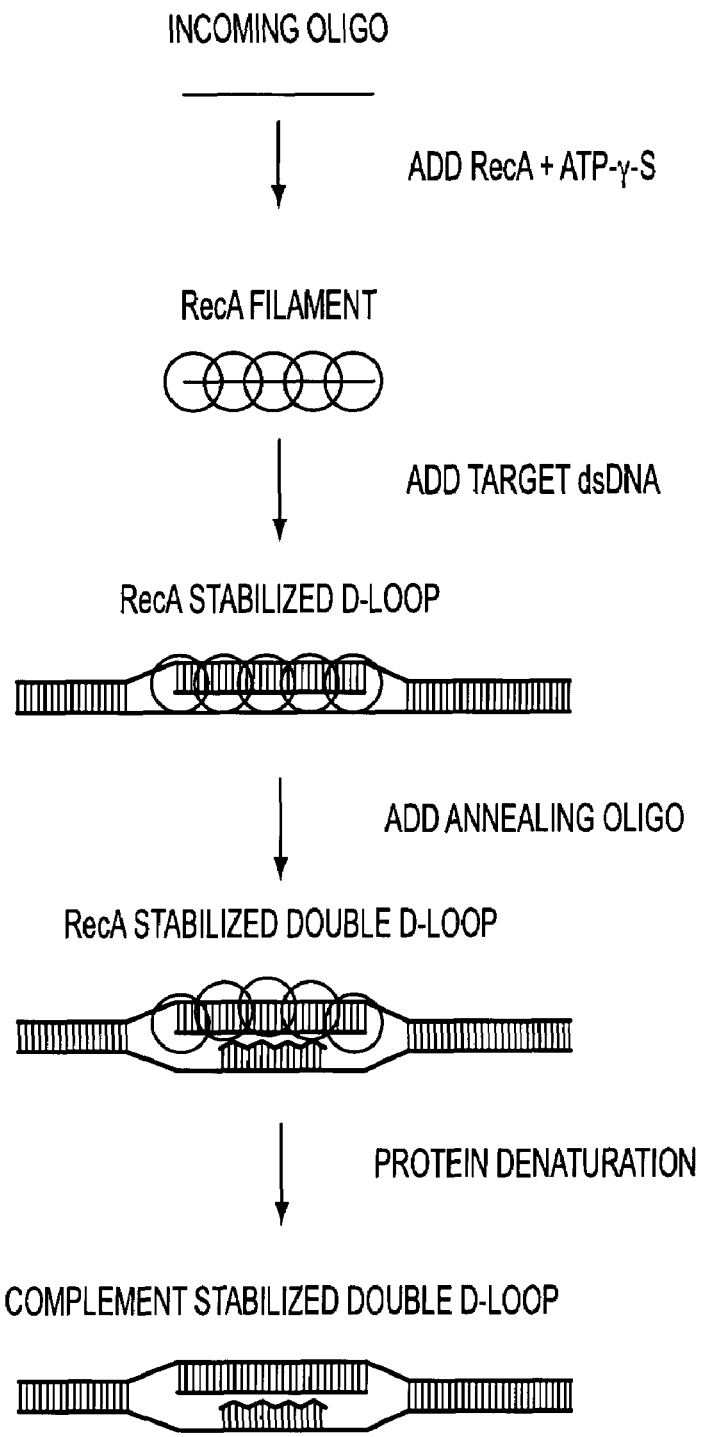
FIG. 1 is a flow diagram for the generation of double D-loops according to embodiments of the methods of the present invention.

We have developed reaction conditions under which the paradigmatic mismatch tolerance of RecA-mediated D-loop formation does not act to prohibit single nucleotide mismatch discrimination. Using these conditions, we have been able for the first time to develop D-loop and double D-loop based methods for detecting and separating double-stranded nucleic acid targets that differ from polymorphic variants by as few as a single nucleotide. The methods are readily multiplexed, permitting a large number of loci to be screened within a single sample, may be adapted to a variety of existing detection systems, and permit target amplification without PCR, increasing fidelity. The ability to separate selected double stranded variants, with or without contemporaneous detection, offers significant advantages over current genotyping methods, and finds particular utility in facilitating the construction of coisogenic cell collections in which the cells differ genotypically by single nucleotide changes targeted to defined loci.

Preferred reaction conditions can differ depending upon the topological state of the target.

In a first aspect, therefore, the invention provides a method for distinguishing the presence of a nonsupercoiled target nucleic acid from the presence of nonsupercoiled target variants within a sample of nucleic acids, the variants differing from the target by as few as one nucleotide within a common target query region.

The method comprises using a recombinase to mediate formation of at least one deproteinization-stable double D-loop in the query region of the target, under conditions that favor double D-loop formation at the target query region over formation at variants that differ from the target by as few as one nucleotide therefrom, and then distinguishing the degree of formation of double D loops that are stable to deproteinization. A greater degree of formation distinguishes the presence of target from that of variants.

In typical embodiments, the double D-loop formation conditions comprise contacting the nucleic acid sample with a first oligonucleotide and a second oligonucleotide (hereinafter also denominated "incoming" and "annealing" oligonucleotides, respectively). The first oligonucleotide may be contacted to sample before the second oligonucleotide or contemporaneously therewith.

The first oligonucleotide includes a complementarity region that is perfectly complementary in sequence to a first strand of the target across the entirety of the target query region. The second oligonucleotide includes a complementarity region that is perfectly complementary in sequence to a second strand of the target across at least a portion of the target query region. And at least one of the first or second oligonucleotide complementarity regions is imperfectly complementary to the respective first or second strands of the query region of each of the target variants desired selectively to be discriminated from target.

The first oligonucleotide is bound by a recombinase. The second oligonucleotide comprises base modifications and does not substantially bind the recombinase. And at least one of the first and second oligonucleotides is distinguishably detectable.

In a second aspect, the invention provides a method of distinguishing the presence of a supercoiled target nucleic acid from the presence of supercoiled target variants within a sample of nucleic acids, the variants differing from the target by as few as one nucleotide within a common target query region.

The method comprises using a recombinase to mediate formation of at least one deproteinization-stable single D-loop or double D-loop in the query region of the target, under conditions that favor formation at the target query region over formation at variants that differ from the target by as few as one nucleotide therefrom, and then distinguishing the degree of formation of single D-loops or double-D loops that are stable to deproteinization, a greater degree of formation distinguishing the presence of target from that of variants.

Formation conditions in this aspect of the invention typically comprise contacting the sample with at least a first oligonucleotide to form at least a single D-loop at the target query region.

The first oligonucleotide is bound by a recombinase, and includes a complementarity region that is (i) perfectly complementary in sequence to a first strand of the target across the entirety of the target query region and (ii) imperfectly complementary to a first strand of the query region of each of the target variants desired to be distinguished.

The method may further comprise contacting the sample with a second, "annealing", oligonucleotide to effect formation of a double D-loop at the target query region. The second oligonucleotide comprises base modifications, does not substantially bind recombinase, and includes a complementarity region that is perfectly complementary in sequence to a second strand of the target across at least a portion of the target query region.

In these latter, two oligonucleotide, double D-loop embodiments, at least one of the first and second oligonucleotide complementarity regions is imperfectly complementary to a respective strand of the query region of each of the target variants, and the second oligonucleotide is typically distinguishably detectable.

In the methods of the present invention, whether for distinguishing nonsupercoiled or supercoiled targets from variants thereof, the recombinase is a RecA-like recombinase.

The best known RecA-like recombinase is the RecA protein from *E. coli*, which is available commercially (Roche Applied Science, Indianapolis, Ind. USA).

RecA orthologues have also been identified in a wide variety of prokaryotic genera, including *Bacillus* (*B. halodurans*, GenBank accession no. NP_243249), *Streptomyces* (*S. agalactiae*, GenBank accession no. NP_689079; *S. pyogenes* MGAS315, GenBank accession no. NP_665604); *Staphylococcus* (*S. aureus* subsp. *Aureus* MW2, GenBank accession no. NP_645985); *Brucella* (*B. melitensis*, GenBank accession no. NP_539704); *Helicobacter* (*H. pylori*, GenBank accession no. NP_206952); *Corynebacterium* (*C. glutamicum*, GenBank accession no. NP_601162); *Bordetella* (*B. hinzii*, GenBank accession no. AAM92267); *Bacteroides* (*B. fragilis*, GenBank accession no. AAK58827); *Haemophilus* (*H. influenzae*, GenBank accession no. AAM91954); archaebacteria (Reich et al., *Extremophiles* 5(4):265-75 (2001); and others.

In eukaryotes, RecA orthologues are typically members of the Rad51 family, Shibata et al., *Proc. Natl. Acad. Sci. USA* 98:8425-8432 (2001), members of which have been identified in a wide variety of eukaryotic organisms including yeasts, such as *Saccharomyces cerevisiae* (GenBank accession no. NP_011021), *Drosophila melanogaster* (GenBank accession no. Q27297), *Caenorhabditis elegans* (GenBank accession no. BAA24982), and *homo sapiens*(Yoshimura et al., "Cloning and sequence of the human RecA-like gene cDNA," *Nucl. Acids Res.* 21(7):1665 (1993); GenBank accession no. NP_002866).

Allelic variants and engineered mutants (collectively, muteins) of RecA and of its orthologues have also been described, including recA-803, Madiraju et al., *Proc. Natl. Acad. Sci. USA* 85(18):6592-6 (1988).

For purposes of the present invention, the phrases "recombinase" and "RecA-like recombinase" include all such RecA orthologues and variants that are capable of forming nucleoprotein filaments with single-stranded DNA and thereafter mediating sequence-specific D-loop formation. Functional tests for the sufficiency of any such candidate recombinase for use in the methods of the present invention may conveniently include substitution of the candidate protein for *E. coli* RecA in the assays further described in the Examples below.

The first, or "incoming" oligonucleotide, is bound by the recombinase (so bound, the oligonucleotide is typically referred to as a nucleoprotein filament or RecA filament). Accordingly, the incoming oligonucleotide is composed of nucleobases that do not preclude RecA binding, typically natural deoxyribonucleosides in typical phosphodiester linkage.

In some embodiments, the methods of the present invention include the antecedent step of binding RecA to the incoming oligonucleotide to form a nucleoprotein filament.

Nucleoprotein filament formation is typically performed in the presence of at least one co-factor, such as ATPγS, GTPγS, a mixture of ATPγS and rATP, or rATP alone in the presence of a rATP regenerating system. In a particularly useful embodiment, the RecA protein coating reactions of the methods of the present invention are carried out using ATPγS.

Conditions for creating RecA filaments are well established for E. coli RecA; representative conditions are set forth in the Examples herein below. Conditions for RecA mutants and RecA orthologues may be determined by routine experimentation. In one approach, the mutant or orthologue may be substituted for RecA in the strand exchange activity assay described in Cox et al., Proc. Natl. Acad. Sci. USA 78:3433 (1981), the disclosure of which is incorporated herein by reference in its entirety, and reaction conditions routinely altered to determine optimal conditions. In another approach, the mutant or orthologue may be substituted for RecA in any of the assays set forth in the Examples below, and reaction conditions routinely altered to determine optimal conditions.

The first oligonucleotide is typically single-stranded, and is typically at least about 25, 26, 27, 28, 29, or 30 nucleotides in length, may be about 35, 40, 45, or 50 nucleotides in length, and may even be longer, including 75, 100, even 200, 300, 400, or 500 nt in length. The first oligonucleotide is typically less than about 100 nt in length, often less than about 75 nt in length, and often less than about 50, 49, 48, 47, 46, 45, 44, 43, 42, 41 or 40 nt in length, with lengths of about 30, 31, 32, 33, 34, 35, 36, 37, 38, 39, 40, 41, 42, 43, 44, 45, 46, 47, 48, 49, or 50 nt being typical.

The first oligonucleotide includes a complementarity region that is perfectly complementary in sequence to a first strand of the target across the entirety of the target query region.

The target query region is that region of the target as to which selectivity among polymorphic variants of the target is desired. It is defined by the first oligonucleotide, and is that region of the target first strand that is perfectly complementary in sequence, in the Watson-Crick (as contrasted to Hoogstein) sense, to at least a portion of the sequence of the first oligonucleotide.

The complementarity region of the first oligonucleotide (and by definition the target query region) is at least about 25, 26, 27, 28, 29, or 30 nucleotides in length, may be at least about 35, 40, 45, or 50 nucleotides in length, and may even be longer, including 75, 100, even 200, 300, 400, or 500 nt in length. Typically, the complementarity region is less than about 100 nt in length, often less than about 75 nt in length, and often less than about 50, 49, 48, 47, 46, 45, 44, 43, 42, 41 or 40 nt in length, with lengths of about 30, 31, 32, 33, 34, 35, 36, 37, 38, 39, 40, 41, 42, 43, 44, 45, 46, 47, 48, 49, or 50 nt being typical.

The first oligonucleotide may include regions additional to the complementarity region.

As further discussed below, such regions may usefully be used, for example, to provide genotypic labels ("bar codes", or "tags") that uniquely identify the oligonucleotide; to provide priming sites for oligonucleotide-mediated amplification reactions; to provide phage promoter sites for generating RNA transcripts; and to provide restriction sites to facilitate subsequent cloning of the target query region.

The second, or "annealing", oligonucleotide comprises base modifications and does not substantially bind the recombinase. The inability substantially to bind recombinase is typically, but need not invariably, be due to the presence of the modified bases.

Among base modifications usefully included in the second oligonucleotide are locked nucleic acid ("LNA") residues, ribonucleic acid residues, such as 2'OMe residues, or peptide nucleic acid (PNA) residues. Other modified bases that may be used include, for example, 2-aminoadenine and cytosine/ uracil substituted at the 5 position with a methyl, propynyl or bromo group.

LNAs are bicyclic and tricyclic nucleoside and nucleotide analogs and the oligonucleotides that contain such analogs. The basic structural and functional characteristics of LNAs and related analogues that usefully may be incorporated into the second ("annealing") oligonucleotide in the methods of the present invention are disclosed in various publications and patents, including WO 99/14226, WO 00/56748, WO 00/66604, WO 98/39352, U.S. Pat. Nos. 6,043,060, and 6,268,490, the disclosures of which are incorporated herein by reference in their entireties.

Among such LNAs that may usefully be incorporated into the second oligonucleotide are those described by the following formula:

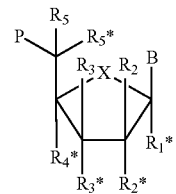

wherein X is selected from —O—, —S—, —N($R^{N*}$)—, —C($R^6R^{6*}$)—, —O—C($R^7R^{7*}$)—, —C($R^6R^{6*}$)—O—, —S—C($R^7R^{7*}$)—, —C($R^6R^{6*}$)—S—, —N($R^{N*}$)—C($R^7R^{7*}$)—, —C($R^6R^{6*}$)—N($R^{N*}$)—, and —C($R^6R^{6*}$)—C($R^7R^{7*}$)—;

B is selected from hydrogen, hydroxy, optionally substituted $C_{1-4}$-alkoxy, optionally substituted $C_{1-4}$-alkyl, optionally substituted C1-4-acyloxy, and the nucleobases; P designates an internucleoside linkage to an adjacent monomer, or a 5'-terminal group, such internucleoside linkage or 5'-terminal group optionally including the substituent $R^5$; one of the substituents $R^2$, $R^{2*}$, $R^3$, and $R^{3*}$ is a group P* which designates an internucleoside linkage to an adjacent monomer, or a 3'-terminal group; one or two pairs of non-geminal substituents selected from the present substituents of $R^{1*}$, $R^{4*}$, $R^5$, $R^{5*}$, $R^6$, $R^{6*}$, $R^7$, $R^{7*}$, $R^{N*}$, and the ones of $R^2$, $R^{2*}$, $R^3$, and $R^{3*}$ not designating P* each designates a covalent bridging moiety consisting of one or more of the following substituents: —C($R^aR^b$)—, —C($R^a$)=C($R^b$)—, —C($R^a$)=N—, —O—, —Si($R^aR^b$)—, —S—, —$SO_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxycarbonyl, aryloxy, arylcarbonyl, heteroaryl, heteroaryloxycarbonyl, heteroaryloxy, heteroarylcarbonyl, amino, mono- and di-($C_{1-6}$-alkyl)amino, carbamoyl, mono- and di-($C_{1-6}$-alkyl)aminocarbonyl, amino-$C_{1-6}$-alkylaminocarbonyl, mono- and di-($C_{1-6}$-alkyl)amino-$C_{1-6}$-alkylaminocarbonyl, $C_{1-6}$-alkylcarbonylamino, carbamido, $C_{1-6}$-alkanoyloxy, sulphono, $C_{1-6}$-alkylsulphonyloxy, nitro, azido, sulphanyl, $C_{1-6}$-alkylthio, and the halogens, where aryl and heteroaryl may be optionally substituted, and where two geminal substituents $R^a$ and $R^b$ together may designate optionally substituted methylene (=$CH_2$), and wherein two non-geminal or geminal substituents selected from $R^a$, $R^b$, and any of the substituents $R^{1*}$, $R^2$, $R^{2*}$, $R^3$, $R^{3*}$, $R^{4*}$, $R^5$, $R^{5*}$, $R^6$ and $R^{6*}$, $R^7$, and $R^{7*}$ which are present and not involved in P, P*, or the covalent bridging moiety or moieties together may form an associated bridging moiety selected from substituents of the same kind as defined before;

the pair(s) of non-geminal substituents thereby forming a mono- or bicyclic entity together with (i) the atoms to which the non-geminal substituents are bound and (ii) any intervening atoms; and each of the substituents $R^{1*}$, $R^2$, $R^{2*}$, $R^3$, $R^{4*}$, $R^5$, $R^{5*}$, $R^6$ and $R^{6*}$, $R^7$, and $R^{7*}$ which are present and not involved in P, P*, or the covalent bridging moiety or moieties is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxycarbonyl, aryloxy, arylcarbonyl, heteroaryl, heteroaryloxycarbonyl, heteroaryloxy, heteroarylcarbonyl, amino, mono- and di($C_{1-6}$-alkyl)amino, carbamoyl, mono- and di($C_{1-6}$-alkyl)aminocarbonyl, amino-$C_{1-6}$-alkylaminocarbonyl, mono- and di($C_{1-6}$-alkyl)amino-$C_{1-6}$-alkylaminocarbonyl, $C_{1-6}$-alkylcarbonylamino, carbamido, $C_{1-6}$-alkanoyloxy, sulphono, $C_{1-6}$-alkylsulphonyloxy, nitro, azido, sulphanyl, $C_{1-6}$-alkylthio, and halogens, where aryl and heteroaryl may be optionally substituted, and where two geminal substituents together may designate oxo, thioxo, imino, or optionally substituted methylene, or together may form a spiro bridging moiety consisting of a 1-5 carbon atom(s) alkylene chain which is optionally interrupted and/or terminated by one or more substituents selected from —O—, —S—, and —(NR$^N$)— where R$^N$ is selected from hydrogen and $C_{1-4}$-alkyl, and where two adjacent (non-geminal) substituents may designate an additional bond resulting in a double bond;

and R$^{N*}$, when present and not involved in a covalent bridging moiety, is selected from hydrogen and $C_{1-4}$-alkyl; and basic salts and acid addition salts thereof.

In the above-described structures, the terms "nucleobase" and "base" cover naturally-occurring nucleobases as well as non-naturally occurring and modified nucleobases. As would be understood, various nucleobases which previously have been considered "non-naturally occurring" have subsequently been found in nature. Thus, "nucleobase" or "base" include not only the known purine and pyrimidine heterocycles, but also heterocyclic analogs and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4$,$N^4$-ethanocytosine, $N^6$,$N^6$-ethano-2,6-diaminopurine, 5-methylcytosine, 5-($C^3$-$C^6$)-alkynylcytosine, 5-fluorouracil, 5-bromouracil, pseudoisocytosine, 2-hydroxy-5-methyl-4-triazolopyridine, isocytosine, isoguanine, inosine and the "non-naturally occurring" nucleobases described in U.S. Pat. No. 5,432,272, the disclosure of which is incorporated herein by reference in its entirety. The terms "nucleobase" and "base" are intended to cover each of these examples as well as analogs and tautomers thereof. Especially useful nucleobases are adenine, guanine, thymine, cytosine, and uracil.

As evident from the general formula above, and the definitions associated therewith, there may be one or several asymmetric carbon atoms present in the LNA-containing annealing oligonucleotides in the methods of the present invention, depending on the nature of the substituents and possible covalent bridging moieties. LNA-containing annealing oligonucleotides used in the present invention are intended to include all stereoisomers arising from the presence of any and all isomers of the individual monomer fragments as well as mixtures thereof, including racemic mixtures. Also included within the scope of the invention are variants of the general formula where B is in the α-configuration.

In one series of useful embodiments, the second oligonucleotide may include LNAs such as those disclosed in WO 99/14226 and U.S. Pat. No. 6,268,490, the disclosures of which are incorporated herein by reference in their entireties, which contain a methylene bridge connecting the 2'-oxygen of the ribose with the 4'-carbon according to the following formula:

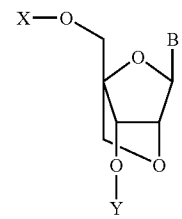

where B is a nucleobase, and X and Y are internucleoside linkages.

In other interesting embodiments of this LNA structure, the 2'-oxygen position is substituted with nitrogen or sulfur as shown in the following structures:

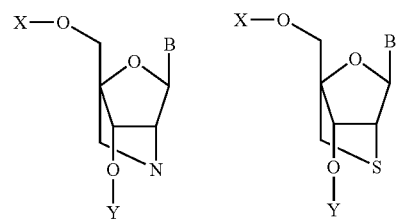

where B is a nucleobase, and X and Y are internucleoside linkages.

Other embodiments of the basic LNA structure usefully included in the annealing oligonucleotides of the present invention are disclosed in WO 99/14226. In these embodiments, the covalent bridging moiety may include more than one carbon atom and may span other positions within the ribose ring according to the following structures:

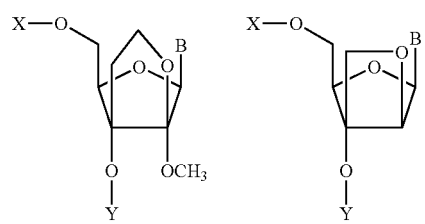

where B is a nucleobase, and X and Y are internucleoside linkages.

In yet other LNA alternatives, the annealing oligonucleotides may include at least one nucleoside having a xylo-LNA structure as disclosed in WO 00/56748, the disclosure of which is incorporated herein by reference in its entirety, and having the general formula:

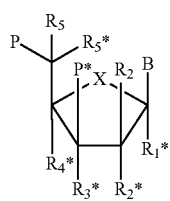

where the internucleoside linkages are designated by P and P*, and the other groups may be the substituents disclosed in WO 00/56748. Specific examples of this analog are disclosed in WO 00/50748 with the following structural framework:

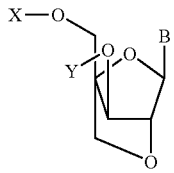

where B is a nucleobase, and X and Y are internucleoside linkages. Also disclosed in WO 00/56748 and considered within the scope of the current invention are nucleoside analogs that contain linkages between the 2' and 5' carbons, of the ribose ring:

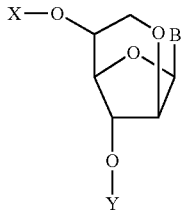

where B is a nucleobase, and X and Y are internucleoside linkages.

Other embodiments of the annealing oligonucleotide may comprise at least one nucleoside having an L-Ribo-LNA structure as disclosed in WO 00/66604, the disclosure of which is incorporated herein by reference in its entirety, and having the general formula:

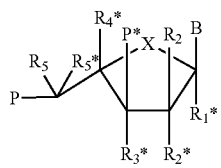

where the internucleoside linkages are designated by P and P*, and the other groups may be the substituents disclosed in WO 00/66604. Specific examples of this analog are disclosed in WO 00/66604 with the following structural framework:

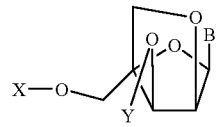

where B is a nucleobase, and X and Y are internucleoside linkages.

Yet other embodiments contain the nucleoside analogs disclosed in U.S. Pat. No. 6,043,060, the disclosure of which is incorporated herein by reference in its entirety. These analogs are represented by monomer units of the general formula:

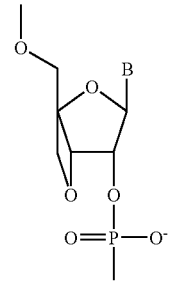

where B is a pyrimidine or purine nucleic acid base, or a derivative thereof, and where, within an annealing oligonucleotide, the plurality of B substituents may be identical to or different from one another.

Synthesis of LNA nucleosides and nucleoside analogs and oligonucleotides that contain them may be performed as disclosed in WO 99/14226, WO 00/56748, WO 00/66604, WO 98/39352, U.S. Pat. Nos. 6,043,060, and 6,268,490. Many may now be ordered commercially (Exiqon, Inc., Vedbaek, Denmark; Proligo LLC, Boulder, Colo., USA).

The annealing oligonucleotide in the methods of the present invention may alternatively, or in addition, include ribonucleic acid residues. Among such residues, 2'OMe residues are conveniently used.

The annealing oligonucleotide may also usefully include peptide nucleic acid (PNA) residues, oligonucleotide analogs in which the deoxyribose backbone of the oligonucleotide is replaced by a peptide backbone, such as repeating units of N-(2-aminoethyl)glycine linked through amide bonds.

Peptide nucleic acids and methods for their synthesis have by now been amply well described, and need not here be described in detail. For recent review, see Nielsen et al., Curr. Issues. Mol. Biol. 1(1-2):89-104 (1999); Nielsen, Curr. Med. Chem. 8(5):545-50 (2001); Nielsen, Curr. Opin. Biotechnol. 12(1):16-20 (2001); Good et al., Antisense Nucleic Acid Drug Dev. 7(4):431-7 (1997); Eriksson et al., Q. Rev. Biophys. 29(4):369-94 (1996); Hyrup et al., Bioorg. Med. Chem. 4(1): 5-23 (1996); Nielsen, Annu. Rev. Biophys. Biomol. Struct. 24:167-83 (1995); Nielsen et al., Bioconjug. Chem. 5(1):3-7 (1994), the disclosures of which are incorporated herein by reference in their entireties. tBoc PNA monomers and reagents for use in PNA synthesis are available commercially from Applied Biosystems, Inc. (Foster City, Calif., USA), which also provides custom PNA oligonucleotide synthesis services.

The annealing oligonucleotides may also usefully include 2-aminoadenine and/or cytosine/uracil substituted at the 5 position with a methyl, propynyl or bromo group.

The annealing oligonucleotide may be composed entirely of modified bases, or may instead comprise both modified and natural bases. The annealing oligo thus includes at least about 30%, 40%, 50%, or at least about 60%, 70%, 75%, 80%, 90%, 95%, and even 100% modified bases. The lower limit for percentage inclusion of modified bases is determined, for any given annealing oligonucleotide sequence and composition, by the requirement that the oligonucleotide not bind substantial amounts of recombinase. The annealing oligonucleotide does not bind substantial amounts of recombinase if the annealing oligonucleotide, after incubation with RecA under conditions that favor filament formation, is alone incapable of mediating the formation of a single D-loop in the target query region. Typically, recombinase binding by the annealing oligonucleotide is undetectable.

The second oligonucleotide is typically single-stranded, and is typically less than about 50 nt in length, often less than about 49, 48, 47, 46, 45, 44, 43, 42, 41, even no more than about 40 nt in length, and may be as short as 39, 38, 37, 36, 35, 34, 33, 32, 31 even as short as 30, 29, 28, 27, 26, 25, 24, 23, 22, 21 or 20 nt in length. The second oligonucleotide may even be as short as 19, 18, 17, 16, or even as short as 15 nt in length. Annealing oligonucleotides of 15 nt are exemplified in the Examples herein below.

The second oligonucleotide includes a complementarity region.

The second oligonucleotide complementarity region is perfectly complementary in sequence to a second strand of the target across at least a portion of the target query region.

Typically, the second oligonucleotide complementarity region will be shorter than that of the first oligonucleotide, will not encompass regions of the target outside the target query area, and will typically be less than about 50 nt, 45 nt, 40 nt, 35 nt, 30 nt, 29 nt, 28 nt, 27 nt, 26 nt, or even less than about 25 nt in length. The second oligonucleotide complementarity region will typically be at least about 15 nt in length, may be 16, 17, 18, 19, 20, 21, 22, 23, 24, even at least about 25 nt in length, although longer regions of complementarity are permissible.

Because the first oligonucleotide is perfectly complementary in sequence to a first strand of the target across the entirety of the target query region, and the second oligonucleotide is perfectly complementary to a second strand of the target across at least a portion of the target query region, the first and second oligonucleotides have at least a region of perfect complementarity therebetween, also termed an "overlap region". The overlap region may extend the entirety of the second oligonucleotide complementarity region, or may instead include only a portion thereof. The overlap region is at least about 5 nt, typically at least about 10 nt, and is often at least about 11 nt, 12 nt, 13 nt, 14 nt, 15 nt, and as long as about 20 nt, 25 nt, 30 nt, 35 nt, 40 nt, 45 nt, even 50 nt.

The second oligonucleotide may include regions additional to the complementarity region. As further discussed below, such regions may usefully be used, for example, to provide genotypic labels ("bar codes", or "tags") that uniquely identify the oligonucleotide; to provide priming sites for oligonucleotide-mediated amplification reactions; to provide phage promoter sites for generating RNA transcripts; and to provide restriction sites to facilitate cloning of the target region.

At least one of the oligonucleotide complementarity regions is imperfectly complementary to its respective strand of the query region of each of the target variants desired selectively to be discriminated from the target. By "imperfectly complementary" is intended at least one mismatch with respect to the respective strand of the target variant. As demonstrated in the Examples set forth herein below, a single base mismatch as between at least one of the first and second oligonucleotides, on the one hand, and the target variant query region, on the other, causes discriminably decreased formation of deproteinization-stable double-D loops at nonsupercoiled variant query regions as compared to formation at the exactly matched nonsupercoiled target. Further mismatches can provide a greater difference in degree of formation.

By "deproteinization-stable" is intended a degree of stability sufficient to permit Dloop or dDloop detection following deproteinization.

In certain embodiments, therefore, the methods of this aspect of the present invention further include the additional step, after formation of single or double D-loops, and typically (but not invariably) before detection, of deproteinizing the nucleic acids in the sample.

Deproteinization may be accomplished, for example, by treatment with SDS or proteinase K, as well as by standard chemical deproteinization methods, such as phenol-based methods, at temperatures up to 25° C., up to 30° C., 35° C., 37° C., at times up to 40° C., 41° C., 42° C., 43° C., 44° C., or 45° C., and even at temperatures as high as 46° C., 47° C., 48° C., 49° C., 50° C., 51° C., 52° C., 53° C., 54° C., or 55° C., and on occasion at temperatures as high as 56° C., 57° C., 58° C., 59° C., even 60° C., for times up to 1, 2, 2.5, 3, 4, or 5 minutes, even as long as 6, 7, 8, 9 or 10 minutes, although the shorter incubation times are more typical.

Depending upon the length and sequence of the complementarity regions, the base composition of the annealing oligonucleotide, the nature of the recombinase, and other factors, the single or double D-loops at the target query region are stable after deproteinization for periods of up to 1, 2, 2.5, 3, 4, or 5 minutes, even as long as 6, 7, 8, 9 or even 10 minutes, at temperatures as high as 20° C., 25° C., up to 30° C., 35° C., 37° C., at times up to 40° C., 41° C., 42° C., 43° C., 44° C., or 45° C., and even at temperatures as high as 46° C., 47° C., 48° C., 49° C., 50° C., 51° C., 52° C., 53° C., 54° C., or 55° C., and on occasion at temperatures as high as 56° C., 57° C., 58° C., 59° C., even 60° C. The deproteinized Dloops or dDloops are stable for longer periods, up to 1 hour, 2 hours, 3 hours, 4 hours, 5 hours, 6 hours, even up to 10-18 hours or more at temperatures no higher than 4° C., and may be stable for periods longer than 1 day at temperatures of −20° C. or below.

In the single D-loop methods of the present invention, the first oligonucleotide is detectable. In the double D-loop methods of the present invention, whether for distinguishing supercoiled or nonsupercoiled targets, at least one of the first and second oligonucleotides is detectable, optionally both.

In embodiments in which both first and second oligonucleotides are detectable, the first and second oligonucleotides may be distinguishably detectable with respect to one another. In embodiments in which a plurality of first and second oligonucleotide pairs are used, further described below, each first oligonucleotide may be distinguishably detectable from the others of the first oligonucleotides, and each second oligonucleotide may be distinguishably detectable from the others of the second oligonucleotides. In these latter embodiments, the first and second oligonucleotides of each separate pair may or may not be distinguishable therebetween.

In a variety of embodiments, either or both of the first and second oligonucleotides may include at least one label, which can be directly or indirectly detectable.

Detectable labels include, e.g., a radionuclide, a fluorophore, a fluorescence resonance energy transfer ("FRET")

tandem fluorophore, a FRET donor and/or acceptor, or a mass tag. Indirectly detectable labels include, e.g., an enzyme, a genotypic label, or a hapten.

The label may, for example, be a radionuclide, such as $^{33}$P, $^{32}$P, $^{35}$S, and $^{3}$H.

The label may instead be a fluorophore. Commercially available fluorescent nucleotide analogues readily incorporated into the first and/or second oligonucleotides include, for example, Cy3-dCTP, Cy3-dUTP, Cy5-dCTP, Cy3-dUTP (Amersham Biosciences, Piscataway, N.J., USA), fluorescein-12-dUTP, tetramethylrhodamine-6-dUTP, Texas Red®-5-dUTP, Cascade Blue®-7-dUTP, BODIPY® FL-14-dUTP, BODIPY® ™R-14-dUTP, BODIPY® TR-14-dUTP, Rhodamine Green™-5-dUTP, Oregon Green® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, Alexa Fluor® 546-14-UTP (Molecular Probes, Inc. Eugene, Oreg., USA). Protocols are available for custom synthesis of nucleotides having other fluorophores. Henegariu et al., "Custom Fluorescent-Nucleotide Synthesis as an Alternative Method for Nucleic Acid Labeling," *Nature Biotechnol.* 18:345-348 (2000), the disclosure of which is incorporated herein by reference in its entirety.

Other fluorophores available for post-synthetic attachment include, inter alia, Alexa Fluor® 350, Alexa Fluor® 532, Alexa Fluor® 568, Alexa Fluor® 594, Alexa Fluor® 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3.5, Cy5.5, and Cy7 (Amersham Biosciences, Piscataway, N.J. USA, and others).

FRET tandem fluorophores may also be used, such as PerCP-Cy5.5, PE-Cy5, PE-Cy5.5, PE-Cy7, PE-Texas Red, and APC-Cy7.

Pairs of individual fluorophores that can participate in FRET may also be used, with the two fluorophores of the pair present respectively on first and second oligonucleotides or present together on either or both of the first and second oligonucleotides.

Such FRET fluorophore pairs are well known in the art and include, e.g., fluorescein isothiocyanate (FITC) and tetramethylrhodamine isothiocyanate (TRITC); FITC/Texas Red™ (Molecular Probes, Inc.); FITC/N-hydroxysuccinimidyl 1-pyrenebutyrate (PYB); FITC/eosin isothiocyanate (EITC); FITC/tetramethylrhodamine (TAMRA); and various Alexa Fluor pairs (Molecular Probes, Inc.), such as Alexa Fluor 488 and any one of Alex Fluors 546, 555, 568, 594, or 647.

FRET donors may also be paired with quenchers, with the donor and quencher of the pair present respectively on first and second oligonucleotides, or present together on either or both of the first and second oligonucleotides.

Suitable fluorophore-quencher pairs are well known in the art and include, e.g., FAM, HEX, TAMRA, EDANS and Texas Red™ as fluorophore, with dabcyl useful as a common quencher. Other quenchers include, e.g., QSY 7, QSY 9, QSY 21 and QSY 35 (all from Molecular Probes, Inc., Eugene, Oreg.); gold nanoparticles (Dubertret et al., *Nature Biotechnol.* 19:365-370 (2001)), and other metals and metalloids, both as macroscopic solids and nanoparticles, including particles in colloid suspension.

Labels that are detectable by mass spectrometry, "mass tags", may also be used. Mass tags can be designed to provide hundreds of mass spectrally distinguishable species, allowing highly multiplexed reactions, and can be designed to be cleavable, typically photochemically cleavable, from the labeled nucleic acid, simplifying analysis. See, e.g., Kokoris et al., *Mol Diagn.* 5(4):329-40 (2000) and Pusch et al., *Pharmacogenomics* 3(4):537-48 (2002), the disclosures of which are incorporated herein by reference in their entireties.

At least one oligonucleotide, optionally both, may instead or in addition include at least one indirectly detectable label.

For example, the oligonucleotide may include an enzyme.

Enzymes useful for colorimetric detection are well known, and include alkaline phosphatase, β-galactosidase, glucose oxidase, horseradish peroxidase (HRP), and urease. Typical substrates for production and deposition of visually detectable products include o-nitrophenyl-beta-D-galactopyranoside (ONPG); o-phenylenediamine dihydrochloride (OPD); p-nitrophenyl phosphate (PNPP); p-nitrophenyl-beta-D-galactopyranoside (PNPG); 3',3'-diaminobenzidine (DAB); 3-amino-9-ethylcarbazole (AEC); 4-chloro-1-naphthol (CN); 5-bromo-4-chloro-3-indolyl-phosphate (BCIP); ABTS®; BluoGal; iodonitrotetrazolium (INT); nitroblue tetrazolium chloride (NBT); phenazine methosulfate (PMS); phenolphthalein monophosphate (PMP); tetramethyl benzidine (TMB); tetranitroblue tetrazolium (TNBT); X-Gal; X-Gluc; and X-Glucoside.

Enzymes may also be used for luminescent detection. Luminescent labels, such as enhanced chemiluminescence labels, are well known in the art.

For example, in the presence of hydrogen peroxide ($H_2O_2$), horseradish peroxidase (HRP) can catalyze the oxidation of cyclic diacylhydrazides, such as luminol, with subsequent light emission. Strong enhancement of the light emission can be produced by enhancers, such as phenolic compounds. Thorpe et al., *Methods Enzymol.* 133:331-53 (1986); Kricka et al., *J. Immunoassay* 17(1):67-83 (1996); and Lundqvist et al., *J. Biolumin. Chemilumin.* 10(6):353-9 (1995), the disclosures of which are incorporated herein by reference in their entireties. Kits for such chemiluminescent and enhanced chemiluminescent detection of nucleic acids are available commercially.

Either or both of the first and second oligonucleotides may include a "genotypic label,"—variously termed a "bar code tag" or "tag" in the art—which are short sequences designed algorithmically to maximize discrimination on a microarray having complements of the respective tags; a 1:1 correspondence as between tag sequence and first and/or second oligonucleotide permits each oligonucleotide so labeled to be detected by detection of the bar code uniquely associated therewith. See, e.g., Shoemaker et al., *Nature Genet.* 14(4): 450-6 (1996); EP 0799897; Fan et al., *Genome Res.* 10:853-60 (2000); and U.S. Pat. No. 6,150,516, the disclosures of which are incorporated herein by reference in their entireties.

The oligonucleotides can, in addition or in the alternative, include a detectable hapten, typically a hapten that is indirectly detectable. Haptens that are commonly conjugated to nucleotides for incorporation into oligonucleotides include biotin (biotin-11-dUTP, Molecular Probes, Inc., Eugene, Oreg., USA; biotin-21-UTP, biotin-21-dUTP, Clontech Laboratories, Inc., Palo Alto, Calif., USA), digoxigenin (DIG-11-dUTP, alkali labile, DIG-11-UTP, Roche Diagnostics Corp., Indianapolis, Ind., USA), and dinitrophenyl (dinitrophenyl-11-dUTP, Molecular Probes, Inc., Eugene, Oreg., USA).

Depending upon the choice of label, deproteinization-stable single or double D-loops may be detected in the methods of the invention by detecting radiation, as by autoradiography or phosphorimaging; by detecting fluorescence, including standard fluorescence, fluorescence resonance energy transfer, fluorescence polarization, and time-resolved fluorescence; colorimetrically; by mass spectrometry, typically time-of-flight mass spectrometry; or luminescently.

In distinguishing supercoiled targets from target variants, we have observed increased selectivity under certain conditions by further contacting the sample with a third oligonucleotide.

Thus, in certain embodiments, the methods further comprise contacting the sample with a third oligonucleotide, either contemporaneously with or subsequent to contact with the first and/or second oligonucleotide.

The third oligonucleotide is typically designed essentially according to the criteria described above for design of the second oligonucleotide, which description is incorporated here by reference, except that the third oligonucleotide includes a complementarity region that is perfectly complementary in sequence to at least a portion of the second strand of the query region of a target variant as to which the target is desired to be discriminated, and imperfectly complementary in sequence to at least a portion of the query region of the target itself.

The third oligonucleotide may, but need not, be detectable. If detectable, it is distinguishably detectable from the second oligonucleotide, and optionally from the first oligonucleotide. If detectable, the third oligonucleotide may be rendered detectable by any of the approaches above-described for the first and/or second oligonucleotides, which description is incorporated here by reference in its entirety.

In the methods of the first aspect of the present invention, the nucleic acid target and the variants to be distinguished therefrom are present in the nucleic acid sample in topologic forms other than supercoils. In the methods of the second aspect of the present invention, the nucleic acid target and variants to be distinguished therefrom are supercoiled.

Nonsupercoiled target and variants may, for example, be linear duplexes, partially duplexed linear molecules, or non-supercoiled circles, such as nicked circles or relaxed covalently closed circles. Linear or partially linearized samples are characteristic, for example, of cellular genomic DNA preparations from eukaryotes, artificial chromosomes, such as YACs, PCR products, and various viral preparations. Nonsupercoiled circles are characteristic, for example, of plasmid, cosmid, or BAC preparations that have been relaxed, either by nicking (as by nucleases, chemical treatment, UV exposure, or physical shearing) or by treatment with a topoisomerase. Supercoiled target and variants typically will be present within plasmids or cosmids.

Both nonsupercoiled and supercoiled samples may usefully include genomic DNA targets.

Genomic DNA samples may be derived directly from cellular chromosomes or may instead be derived from recombinant sources. Samples derived directly from cellular chromosomes lack vector sequences and will typically be in nonsupercoiled form; samples derived from recombinant sources include vector sequences in addition to the genomic target and may be supercoiled. Cellular genomic samples may include DNA in aqueous composition, or may instead include DNA in desiccated or fixed form as in chromosomal spreads typically used for karyotyping. Recombinant genomic samples will typically be in aqueous composition.

Nonsupercoiled recombinant genomic targets usefully discriminated from variants in the methods of the present invention include genomic targets present within artificial chromosomes, such as YACs (yeast artificial chromosomes), BACs (bacterial artificial chromosomes), PACs (P-1 derived artificial chromosomes), HACs (human artificial chromosomes), and PLACs (plant artificial chromosomes). Artificial chromosomes are reviewed in Larin et al., *Trends Genet.* 18(6):313-9 (2002); Choi et al., *Methods Mol. Biol.* 175:57-68 (2001); Brune et al., *Trends Genet.* 16(6):254-9 (2001); Ascenzioni et al., *Cancer Lett.* 118(2):135-42 (1997); Fabb et al., *Mol. Cell. Biol. Hum. Dis. Ser.* 5:104-24 (1995); Huxley, *Gene Ther.* 1(1):7-12 (1994), the disclosures of which are incorporated herein by reference in their entireties. Other vectors capable of including genomic DNA in nonsupercoiled form include various viral, typically eukaryotic viral, vectors, such as adenoviral, varicella, and herpesvirus vectors.

In certain useful embodiments, genomic targets to be distinguished from their respective variants are present within vectors that permit integration of the target into a cellular chromosome. In particularly useful embodiments, genomic targets are present within vectors that permit site-directed integration of the target into a cellular chromosome. Usefully, the vector is an artificial chromosome and site-specific integration may be performed by recombinase mediated cassette exchange (RMCE).

In RMCE, a region of DNA (cassette) desired to be integrated into a specific cellular chromosomal location is flanked in a recombinant vector by sites that are recognized by a site-specific recombinase, such as loxP sites and derivatives thereof for Cre recombinase and FRT sites and derivatives thereof for Flp recombinase. Other site-specific recombinases having cognate recognition/recombination sites useful in such methods are known (see, e.g., Blake et al., *Mol Microbiol* 23(2):387-98 (1997)).

The site in the cellular chromosome into which the cassette is desired site-specifically to be integrated is analogously flanked by recognition sites for the same recombinase.

To favor a double-reciprocal crossover exchange reaction between vector and chromosome, two approaches are typical. In the first, the two sites (such as lox or FRT) that flank the cassettes in both vector and cellular chromosome are heterospecific: that is, they differ from one another and recombine with each other with far lower efficiency than with sites identical to themselves. In the second, the lox or FRT sites are inverted. See, e.g., Baer et al., *Curr. Opin. Biotechnol.* 12:473-480 (2001); Langer et al., *Nucl. Acids Res.* 30:3067-3077 (2002); Feng et al., *J. Mol. Biol.* 292:779-785 (1999), the disclosures of which are incorporated herein by reference in their entireties.

Recombinational exchange of the cassettes from vector to cellular chromosome, with integration of the construct cassette site-specifically into the cellular chromosome, is effected by introducing the recombinant construct into the cell and expressing the site-specific recombinase appropriate to the recombination sites used. The site-specific recombinase may be expressed transiently or continuously, either from an episome or from a construct integrated into cellular chromosome, using techniques well known in the art.

In such embodiments, in which genomic targets to be distinguished from their respective variants are present within vectors that permit site-specific integration into chromosomes, the methods of the present invention can be used to detect and discriminate those vectors that include targets desired to be integrated site-specifically into a cellular chromosome, with selectivity sufficient to distinguish the genomic target from variants that differ from it by as few as one nucleotide.

As described in further detail below, the methods of the present invention further permit the separation and purification of targets from variants thereof, and also from unrelated targets. In embodiments in which genomic targets to be distinguished from their respective variants (or other targets) are present within vectors that permit site-specific integration into chromosomes, the methods of the present invention can be used to separate and purify those vectors that include targets desired to be integrated site-specifically into a cellular chromosome, with selectivity sufficient to isolate the genomic target from variants that differ from it by as few as one nucleotide.

Such embodiments may usefully be combined with methods for targeting nucleic acid sequence changes to the genomic targets present within such vectors.

We have recently described methods for targeting single nucleotide changes directly into long pieces of genomic DNA present within YACs, BACs, and even intact cellular chromosomes through use of sequence-altering oligonucleotides. See international patent publication nos. WO 01/73002, WO 01/92512, and WO 02/10364; and commonly owned and copending U.S. provisional patent application Nos. 60/326,041, filed Sep. 27, 2001, 60/337,129, filed Dec. 4, 2001, 60/393,330, filed Jul. 1, 2002, 60/363,341, filed Mar. 7, 2002; 60/363,053, filed Mar. 7, 2002, and 60/363,054, filed Mar. 7, 2002, the disclosures of which are incorporated herein by reference in their entireties.

Other approaches for targeting sequence changes using sequence altering oligonucleotides have also been described. See e.g. U.S. Pat. Nos. 6,303,376; 5,776,744; 6,200,812; 6,074,853; 5,948,653; 6,136,601; 6,010,907; 5,888,983; 5,871,984; 5,760,012; 5,756,325; and 5,565,350, the disclosures of which are incorporated herein by reference in their entireties.

Using such targeting methods, small changes, including single nucleotide changes, can be targeted to genomic targets that are present within recombinant vectors. The methods of the present invention can then be used to identify, quantify, separate, and purify the successfully targeted constructs. If the target is present in a vector that permits the subsequent site-specific integration of the target into a cellular chromosome, the successfully targeted variant can then be integrated site-specifically into a cellular chromosome.

This approach provides a single-copy integrant of defined and chosen sequence in a defined cellular genomic milieu. It is known that such site-specific integration provides more consistent expression than does random integration. Feng et al., *J. Mol. Biol.* 292:779-285 (1999).

We have recently described the use of oligonucleotide-mediated sequence alteration in the creation of collections of coisogenic eukaryotic cell lines—collections of genotypically distinct cells, derived from a common ancestor cell, that are engineered to differ from one another in genomic sequence at a predetermined target locus. Such coisogenic culture collections find utility, for example, in pharmacogenomics applications. See commonly owned and copending U.S. provisional patent application No. 60/325,992, filed Sep. 27, 2001, the disclosure of which is incorporated herein by reference in its entirety.

The methods of the present invention can be used to facilitate creation of such coisogenic cell collections.

With genomic samples, whether obtained directly from cellular chromosomes or within recombinant vectors, the query region may be within the coding region of a gene, within an intergenic region, including promoter or enhancer elements, within an intron if the genomic sample is eukaryotic, or within the 5' or 3' UTR of a gene. In recombinant genomic samples, the target query region may be within a vector sequence.

In another series of embodiments, the nucleic acid sample comprises cDNA, either in nonsupercoiled topologies—e.g. as a cDNA population lacking replicable vector sequences, as from an RT-PCR or cDNA preparation prior to ligation into a vector—or in supercoiled form, as in a plasmid cDNA library.

The sample may contain as little as 100 pg of target nucleic acid, typically no less than 1 ng of target nucleic acid, often 10 ng-100 ng of target nucleic acid, and may include more, including 200 ng, 300 ng, 400 ng, 500 ng of target DNA.

The nucleic acids of the sample to be queried may be derived from a single individual or pooled from a plurality of individuals. The plurality may include as few as two individuals, and may include as many as 3, 4, 5, 10, 20, 30, 40, 50, 75, or even as many as 100 individuals.

The nucleic acids may be derived from a body fluid, either a fluid having formed cellular elements that include nucleic acids or a fluid that lacks formed elements but otherwise includes nucleic acids, including blood, urine, sweat, saliva, sputum, semen, vaginal secretions, cerebrospinal fluid, lymph, breast nipple aspirate, pus, aqueous humor, vitreous humor, and amniotic fluid. The nucleic acids may be derived from a surgical sample, such as a biopsy, aspirate, or lavage. The nucleic acids may also usefully be derived from stool or scat.

In yet other embodiments, the sample may be drawn from cultured cells.

The nucleic acid samples and the targets therein may be drawn from viral, prokaryotic or eukaryotic sources.

Among viruses, targets that may usefully be discriminated from variants using the methods of the present invention include targets present in double-stranded DNA viruses, such as herpesviruses, including human herpesvirus 1 and 2 (HSV-1 and HSV-2), *varicella-zoster* (HSV-3), *cytomegalovirus* (HCMV), human herpesvirus 6, 7, 8 (HHV-6, HHV-7, HHV-8), or Epstein-Barr virus (EBV).

Other useful viral targets include double-stranded forms derived from retroviruses, such as provirus integrants or double-stranded cDNAs prepared synthetically from retrovirus RNA. Retroviruses having targets that may usefully be discriminated from variants using the methods of the present invention include, for example, mammalian type B retroviruses, such as mouse mammary tumor virus; mammalian type C retroviruses, such as murine leukemia virus and reticuloendotheliosis virus (strain T, A); avian type C retroviruses such as avian leukosis virus; type D retroviruses such as Mason-Pfizer monkey virus; BLV-HTLV retroviruses such as bovine leukemia virus; lentiviruses, such as bovine lentiviruses including bovine immunodeficiency virus, feline immunodeficiency virus, visna/maedi virus (strain 1514), and primate lentiviruses such as human immunodeficiency virus 1 (HIV1), human immunodeficiency virus 2 (HIV2), and simian immunodeficiency virus (SIV).

Among prokaryotes, the nucleic acid sample used in the methods of the present invention may usefully be drawn from eubacteria, including gram negative and gram positive bacteria, including *E. coli*.

Among eukaryotes, the nucleic acid sample and target may usefully be drawn from yeasts, such as *S. cerevisiae, Schizosaccharomyces pombe, Ustillago maydis, Neurospora crassa* and *Candida albicans*; mammals, such as primates, including humans, monkeys, and apes, small laboratory animals, such as rodents, including mouse or rat, guinea pigs, and rabbits, and livestock, such as cows, horses, chickens, goats, and sheep; plants, such as angiosperms, gymnosperms, and mosses, including *Chlamydomonas reinhardtii*, *Physcomitrella patens*, and *Arabidopsis thaliana*, and crop plants such as cauliflower (*Brassica oleracea*), artichoke (*Cynara scolymus*), fruits such as apples (*Malus*, e.g. *domesticus*), mangoes (*Mangifera*, e.g. *indica*), banana (*Musa*, e.g. *acuminata*), berries (such as currant, *Ribes*, e.g. *rubrum*), kiwifruit (*Actinidia*, e.g. *chinensis*), grapes (*Vitis*, e.g. *vinifera*), bell peppers (*Capsicum*, e.g. *annuum*), cherries (such as the sweet cherry, *Prunus*, e.g. *avium*), cucumber (*Cucumis*, e.g. *sativus*), melons (*Cucumis*, e.g. *melo*), nuts (such as walnut, *Juglans*, e.g. *regia*; peanut, *Arachis hypogeae*), orange (*Citrus*, e.g. *maxima*), peach (*Prunus*, e.g. *persica*), pear (*Pyra*, e.g. *communis*), plum (*Prunus*, e.g. *domestica*), strawberry (*Fragaria*, e.g. *moschata* or *vesca*), tomato (*Lycopersicon*, e.g. *esculentum*); leaves and forage, such as alfalfa (*Medicago*, e.g. *sativa* or *truncatula*), cabbage (e.g. *Brassica oleracea*), endive (*Cichoreum*, e.g. *endivia*), leek (*Allium*, e.g. *porrum*), lettuce (*Lactuca*, e.g. *sativa*), spinach (*Spinacia*, e.g. *oleraceae*), tobacco (*Nicotiana*, e.g. *tabacum*); roots, such as arrowroot (*Maranta*, e.g. *arundinacea*), beet (*Beta*, e.g. *vulgaris*), carrot (*Daucus*, e.g. *carota*), cassava (*Manihot*, e.g. *esculenta*), turnip (*Brassica*, e.g. *rapa*), radish (*Raphanus*, e.g. *sativus*), yam (*Dioscorea*, e.g. *esculenta*), sweet potato (*Ipomoea batatas*); seeds, including oilseeds, such as beans (*Phaseolus*, e.g. *vulgaris*), pea (*Pisum*, e.g. *sativum*), soybean (*Glycine*, e.g. *max*), cowpea (*Vigna unguiculata*), mothbean (*Vigna aconitifolia*), wheat (*Triticum*, e.g. *aestivum*), sorghum (*Sorghum* e.g. *bicolor*), barley (*Hordeum*, e.g. *vulgare*), corn (*Zea*, e.g. *mays*), rice (*Oryza*, e.g. *sativa*), rapeseed (*Brassica napus*), millet (*Panicum sp.*), sunflower (*Helianthus annuus*), oats (*Avena sativa*), chickpea (*Cicer*, e.g. *arietinum*); tubers, such as kohlrabi (*Brassica*, e.g. *oleraceae*), potato (*Solanum*, e.g. *tuberosum*) and the like; fiber and wood plants, such as flax (*Linum* e.g. *usitatissimum*), cotton (*Gossypium* e.g. *hirsutum*), pine (*Pinus sp.*), oak (*Quercus sp.*), eucalyptus (*Eucalyptus sp.*), and the like and ornamental plants such as turfgrass (*Lolium*, e.g. *rigidum*), petunia (*Petunia*, e.g. *x hybrida*), hyacinth (*Hyacinthus orientalis*), carnation (*Dianthus* e.g. *caryophyllus*), delphinium (*Delphinium*, e.g. *ajacis*), Job's tears (*Coix lacryma-jobi*), snapdragon (*Antirrhinum majus*), poppy (*Papaver*, e.g. *nudicaule*), lilac (*Syringa*, e.g. *vulgaris*), hydrangea (*Hydrangea* e.g. *macrophylla*), roses (including Gallicas, Albas, Damasks, Damask Perpetuals, Centifolias, Chinas, Teas and Hybrid Teas) and ornamental goldenrods (e.g. *Solidago spp.*).

Useful targets derived from human nucleic acids include alleles known or suspected to contribute to disease, to disease predisposition, or to responsiveness to therapeutic agents.

A large and increasing number of alleles of human genes that contribute to or predispose to disease have been identified. Such alleles are catalogued, inter alia, in the Human Gene Mutation Database (http://archive.uwcm.ac.uk/uwcm/mg/hgmd0.html)

and the Online Mendelian Inheritance of Man (OMIM™) (http://www.ncbi.nlm.nih.gov/entrez/query.fcgi?db=OMIM).

The methods of the present invention may be used to identify the presence of such alleles in a patient sample.

Human genomic samples may also usefully be queried using the methods of the present invention for alleles known to affect responsiveness to therapeutic agents.

Genetic polymorphisms in proteins, including the multidrug transporters and cytochromes, are known to play a role in drug sensitivity and in drug resistance. For example, the cytochrome P450 enzyme encoded by CYP2D6 is known to metabolize as many as 20% of commonly prescribed drugs. The enzyme's substrates include debrisoquine, an adrenergic-blocking drug; sparteine and propafenone, both anti-arrhythmic drugs; and amitryptiline, an anti-depressant. The gene is highly polymorphic in the population; certain alleles result in the poor metabolizer phenotype, characterized by a decreased ability to metabolize the enzyme's substrates.

Thus, in one series of embodiments, the targets to be detected by the methods of the present invention are alleles of genes that affect drug metabolism, including: CYP1A2, CYP2C17, CYP2D6, CYP2E, CYP3A4, CYP4A11, CYP1B1, CYP1A1, CYP2A6, CYP2A13, CYP2B6, CYP2C8, CYP2C9, CYP11A, CYP2C19, CYP2F1, CYP2J2, CYP3A5, CYP3A7, CYP4B1, CYP4F2, CYP4F3, CYP6D1, CYP6F1, CYP7A1, CYP8, CYP11A, CYP11B1, CYP11B2, CYP17, CYP19, CYP21A2, CYP24, CYP27A1, CYP51, ABCB1, ABCB4, ABCC1, ABCC2, ABCC3, ABCC4, ABCC5, ABCC6, MRP7, ABCC8, ABCC9, ABCC10, ABCC11, ABCC12, EPHX1, EPHX2, LTA4H, TRAG3, GUSB, TMPT, BCRP, HERG, hKCNE2, UDP glucuronosyl transferase (UGT), sulfotransferase, sulfatase, glutathione S-transferase (CST)-alpha, glutathione S-transferase-mu, glutathione S-transferase-pi, ACE, and KCHN2.

In other embodiments, the targets can be alleles that affect responsiveness to a single drug, or a single class of drugs. For example, the targets can be alleles of genes, or variants of gene fusions, such as the BCR-ABL gene fusion, that affect responsiveness to tyrosine kinase inhibitors, such as imatinib (Gleevec). Resistance-conferring alleles of BCR-ABL are disclosed in Shat et al., *Cancer Cell* 2:117-125 (2002), the disclosure of which is incorporated herein by reference in its entirety.

In some embodiments, the sample includes at least one target variant in addition to the target desired selectively to be detected.

In certain of these embodiments, the target variant differs from the target by as few as one nucleotide in the common query region, and up to 2, 3, 4, 5, 6, 7, 8, 9, even 10 nucleotides in the common query region. Frequently, the variant differs from the target in the common query region by no more than 9, 8, 7, 6 and even by no more than 5 nucleotides. In some embodiments, the sample includes at least one target variant in addition to the target desired selectively to be detected, the target and variant differing in the common query region by 1, 2, 3, 4, or 5 nucleotides.

The variant may be a naturally-occurring allelic variant, a separate member of a gene family, an orthologue from a heterologous species, or a recombinantly engineered variant.

In certain embodiments, the sample includes a plurality of variants in addition to the target desired selectively to be detected. Each of the plurality of variants differs from the target by as few as one nucleotide in the query region that is common therebetween, and up to 2, 3, 4, 5, 6, 7, 8, 9, even 10 nucleotides in the query region that is common therebetween. Frequently, each of the plurality of variants differs from the target in the common query region by no more than 9, 8, 7, 6 and even by no more than 5 nucleotides. In some embodiments, the sample includes a plurality of target variants in addition to the target desired selectively to be detected, the target and each of the variants differing in a query region common therebetween by 1, 2, 3, 4, or 5 nucleotides.

The methods of the present invention may further comprise a step in which single D-loop- or double D-loop-containing targets are separated from other nucleic acids in the sample. Such an optional separation step may be performed after an optional deproteinization step, and either before or after detection, with separation after deproteinization and before detection exemplified in Examples set forth herein below.

Separation may be based upon inherent physical properties of D-loops or dDloops that permit duplexes containing D-loops or dDloops to be distinguished from duplexes lacking such structures. Among such properties is altered mobility during electrophoresis, such as gel electrophoresis or capillary electrophoresis.

Separation may, in the alternative or in addition, be based upon properties that are engineered into the Dloops or dDloops.

For example, in certain embodiments, either or both of the first and second oligonucleotides may include a moiety that permits subsequent capture, and thus separation, of the D-loop or dDloop-containing duplexed DNA.

The capture moiety is typically one member of a specific binding pair.

"Specific binding" refers to the ability of two molecular species concurrently present in a heterogeneous (inhomogeneous) sample to bind to one another in preference to binding to other molecular species in the sample. Typically, a specific binding interaction will discriminate over adventitious binding interactions in the reaction by at least two-fold, more typically by at least 10-fold, often at least 100-fold; when used to detect analyte, specific binding is sufficiently discriminatory when determinative of the presence of the analyte in a heterogeneous (inhomogeneous) sample. Typically, the affinity or avidity of a specific binding reaction is least about $10^7 \, M^{-1}$, using at least $10^8 \, M^{-1}$ to at least about $10^9 \, M^{-1}$, and often greater, including affinities or avidities up to $10^{10} \, M^{-1}$ to $10^{12} \, M^{-1}$.

The phrase "specific binding pair" refers to pairs of molecules, typically pairs of biomolecules, that exhibit specific binding.

A wide range of specific binding pair members that can be used for capture of oligonucleotides are known in the art.

Among these are small capture moieties colloquially termed "haptens" irrespective of their antigenicity. Such haptens include biotin, digoxigenin, and dinitrophenyl, each of which may be incorporated enzymatically through use of prior-conjugated nucleotides: biotin-11-dUTP (Molecular Probes, Inc., Eugene, Oreg., USA); biotin-21-UTP, biotin-21-dUTP (Clontech Laboratories, Inc., Palo Alto, Calif., USA), digoxigenin-11-dUTP, alkali labile, digoxigenin-11-UTP (Roche Diagnostics Corp., Indianapolis, Ind., USA)), and dinitrophenyl-11-dUTP (Molecular Probes, Inc., Eugene, Oreg., USA).

Biotin may be captured using avidin, streptavidin, captavidin, neutravidin, or anti-biotin antibodies. Digoxigenin and dinitrophenyl can be captured using antibodies specific for the respective hapten.

Capture to a solid support, after formation of deproteinization-stable single or double D-loops at the target query region, permits separation of the D-loop-containing nucleic acids from nucleic acids in the sample that do not stably bind the oligonucleotide having the capture moiety.

Alternatively, either the first or the second oligonucleotide may be tethered, directly or indirectly, to a solid support at the time of single or double D-loop formation: separating the solid support from the sample after forming deproteinization-stable single or double D-loops at the target query region separates the D-loop-containing nucleic acids from nucleic acids in the sample that do not bind the tethering oligonucleotide.

The solid support, in either the capture moiety or tethered embodiments, may include one or more surfaces of a unitary object, such as a slide or microtiter plate, or may instead include surfaces of a plurality of discrete objects, such as beads.

The solid support may be glass, although other solid materials, such as amorphous silicon, crystalline silicon, or plastics, may also be used. Such plastics include polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, and mixtures thereof.

The solid support may be a surface of a bead, or pellet. The beads need not be spherical. In addition, the beads may be porous, thus increasing the available surface area of the bead available for assay. Bead sizes usefully range from nanometers, e.g. 100 nm, to millimeters, e.g. 5 mm, usefully from about 0.2 micron to about 200 microns, with beads from about 0.5 to about 5 microns being typical.

Suitable bead compositions include those used in peptide, nucleic acid and organic moiety synthesis, and include, for example, controlled pore glass, plastics, such as polystyrene, methylstyrene, acrylic polymers, ceramics, glass, paramagnetic materials, titanium dioxide, latex, cross-linked dextrans, cellulose, and nylon. See, e.g., "Microsphere Detection Guide" (Bangs Laboratories, Inc., http://www.bangslabs.com/products/bangs/guide.php).

Usefully, the beads are magnetic, paramagnetic, or superparamagnetic, permitting separation of the beads from the liquid sample by application of a suitable magnetic field. A variety of such beads may be purchased commercially from Dynal® Biotech Inc. (Lake Success, N.Y. USA) and Miltenyi Biotec Inc. (Auburn, Calif. USA).

In tethered embodiments, the first or second oligonucleotide may be tethered to the solid support by direct covalent linkage, by direct coordinate bonding (for example, as between a thiolated oligonucleotide and a gold or platinum surface), or indirectly using any of a variety of bonds. In a useful series of embodiments, the first or second oligonucleotide is tethered indirectly to a solid support by a strong noncovalent interaction between specific binding partners.

For example, a biotinylated first or second oligonucleotide may be tethered (or, in capture embodiments, captured subsequent to formation of deproteinization-stable single or double D-loops) to a solid support having streptavidin on its surface. Streptavidin-coated magnetic beads useful for this purpose are available commercially from a variety of vendors: Dynabeads M-280 Streptavidin and Dynabeads M-270 Streptavidin from Dynal® Biotech Inc. (Lake Success, N.Y. USA); 1 μm superparamagnetic beads covalently coupled to a highly pure form of streptavidin from New England Biolabs (Beverley, Mass., USA); magnetite- and polymer-coated 1 micron beads from Active Motif (Carlsbad, Calif., USA); streptavidin microbeads from Miltenyi Biotec, Inc. (Auburn, Calif., USA). Microbeads having anti-biotin antibodies are also useful and are available commercially (Miltenyi Biotec, Inc., Auburn, Calif., USA).

A further step of removing the first and second oligonucleotides from the target may be performed. This may usefully be accomplished, for example, by subjecting the sample to conditions, typically after deproteinization, under which the single or double D-loop, but not the target duplex as a whole, is unstable.

The separation step may be iterated as needed to provide the desired degree of separation of target from target variants.

The separation step can effect a purification of the target—measured as the fold-increase in molar ratio of target to a variant concurrently present within the sample that differs from the target within a common query region by as few as one nucleotide—by 2-fold, 3-fold, 4-fold, 5-fold, by as much as 10-fold, 50-fold, 100-fold, even by as much as $10^3$-fold, $10^4$-fold, $10^5$-fold and even as much as $10^6$-fold or more.

In various of the embodiments described above, target is separated from target variants before, after, or coincident with distinguishing the presence of target in the nucleic acid sample.

Detection of target is not required for separation, however.

Thus, in another aspect, the invention provides a method of separating a nonsupercoiled double-stranded nucleic acid target from other nonsupercoiled nucleic acids present within a sample of nucleic acids, with selectivity sufficient to separate the target from variants that differ from said target by as few as one nucleotide within a common target query region.

The method comprises using a recombinase to mediate formation of at least one deproteinization-stable double D loop in the query region of the target, under conditions that favor double D loop formation at the target query region over formation at variants that differ from the target by as few as one nucleotide thereof; and then separating nucleic acids having deproteinization-stable double D loops from other nucleic acids present within said sample.

Formation conditions are as described above, which description is incorporated here by reference in its entirety.

In another aspect, the invention provides a method of separating a supercoiled double-stranded nucleic acid target from other supercoiled nucleic acids present within a sample of nucleic acids, with selectivity sufficient to separate the target from variants that differ from said target by as few as one nucleotide within a common target query region.

The method comprises using a recombinase to mediate formation of at least one deproteinization-stable single D-loop or double D-loop in the query region of the target, under conditions that favor single D-loop or double D-loop formation at the target query region over formation at variants that differ from the target by as few as one nucleotide thereof; and then separating nucleic acids having deproteinization-stable double D loops from other nucleic acids present within said sample.

Formation conditions are as described above, which description is incorporated here by reference in its entirety.

The methods of the present invention may further include the step, after single- or double D-loop formation, of extending by polymerase either or both of the first or second oligonucleotides.

In one series of such embodiments, the first or second oligonucleotide is extended by a single base.

Single base extension (SBE) reactions are commonly used in the art for querying polymorphic sites. In SBE reactions, target specificity is achieved by hybridizing a primer of sufficient length to discriminate among targets; selectivity among target variants is achieved by using the sequence-specificity of a subsequent polymerase reaction to identify a polymorphic nucleotide situated adjacent to the priming site on the template. The extension reaction is limited to a single base in a number of ways, typically by including one or more species of chain-terminating nucleotide. For review, see Kirk et al., *Nucl. Acids Res.* 30:3295-3311 (2002); Syvanen, *Nature Reviews, Genetics* 2:930-942 (2001); Kwok, *Annu. Rev. Genomics Hum. Genet.* 2:235-258 (2001).

Although the methods of the present invention permit target specificity and variant selectivity to be achieved in a single step—by formation of deproteinization-stable single D-loops or double D-loops selectively at specific targets—an additional SBE reaction can provide additional selectivity, additional genotyping information, or facilitate selective isolation. In contrast to standard SBE reactions in the art, the target template is double-stranded, providing significant advantages in sample preparation and in separation and isolation of variants in double-stranded form.

For example, the single base extension may be performed in the presence of one or more distinguishably labeled chain terminating nucleotides.

In embodiments in which neither first nor second oligonucleotide is detectably labeled, label is incorporated, and signal detectable, only if the position queried by SBE has one of the desired sequences. In embodiments in which the first and/or second oligonucleotide is labeled, further label is incorporated only if the position queried by SBE one or more of the desired sequences.

The chain-terminating nucleotide may include a capture moiety.

In embodiments in which neither first nor second oligonucleotide includes a capture moiety, the capture moiety is incorporated, and the target separable from the sample, only if the position interrogated by SBE one of the desired sequences. In embodiments in which the first and/or second oligonucleotide includes a capture moiety, an additional capture moiety is incorporated only if the position interrogated by SBE has one of the desired sequences. If the capture moiety incorporated by single base extension is a different molecular species from that incorporated into first or second oligonucleotide, the polymerase-incorporated moiety can be used for a first round of separation, with the moiety earlier-incorporated into first or second oligonucleotide used for subsequent rounds of purification, or vice versa.

In another series of extension reactions, the first and/or second oligonucleotides are extended more than a single nucleotide. A variety of these embodiments permit amplification of the target query region, or portions thereof; with formation of single D-loops or double D-loops at targets with selectivity sufficient to distinguish target from variants that differ by as few as one nucleotide therefrom, these embodiments permit the selective amplification, from inhomogeneous nucleic acid samples, of desired variants, such as desired allelic variants.

Amplification may be unidirectional or bidirectional, isothermal or thermal cycling, in any combination.

For example, either or both of the first or second oligonucleotide may include a phage RNA polymerase promoter, such as an SP6, T3, or T7 promoter, 5' to its respective complementarity region. Transcription from the phage promoter after dDloop formation provides RNA transcripts that include at least a portion of the target query region. Transcription in the presence of one or more labeled nucleotides permits this RNA amplification product to be detected, for example by contact to a nucleic acid microarray, providing a convenient readout for the genotyping assay.

Isothermal bidirectional amplification may also be performed, essentially as described in U.S. Pat. No. 5,223,414, the disclosure of which is incorporated herein by reference in its entirety. Briefly, at least two D-loops (single or double, depending on the topology of the target) are formed on the target nucleic acid: the first D-loop, as described above, is formed at the query region with selectivity sufficient to distinguish the target from variants that differ in the common query region by as few as one nucleotide therefrom; the second D-loop is formed either 5' or 3' thereto.

The two sets of oligonucleotides are hybridized to the duplex target sequences in the presence of ATPγS and a reaction mixture comprising dNTPs, RecA protein and a DNA polymerase. The reaction is performed below the temperature required for thermal dissociation of the two target strands and continued until a desired degree of amplification of the target sequence is achieved. The reaction may further include repeated additions of (i) DNA polymerase and (ii) RecA protein-coated probes during the course of the amplification reactions. Other approaches to amplification are described in U.S. Pat. No. 5,223,414, incorporated herein by reference in its entirety.

In each set of first and second oligonucleotides, the 3' end of one oligonucleotide will be internal to the region defined by the two sets of oligonucleotides; free hydroxyls at these ends are necessary for the amplification reaction. However, in some embodiments of this amplification method, the 3' ends that are external to the region defined by the two primer sets may optionally be blocked to inhibit the formation of extension products from these ends.

This amplification method can also be used as a detection method or capture method, where detection or capture is accomplished by polymerase-facilitated primer extension from the 3'-ends of each oligonucleotide strand in the presence of dNTP(s), where one or more dNTP contains a detectable or capture moiety.

The methods of the present invention may also include a further step of contacting nucleic acids of the sample with an enzyme capable of cleaving DNA. Typically, the enzyme is capable of cleaving a site within or adjacent to the target query region.

In one series of embodiments, the single or double D-loop formed selectively at the target query region directly blocks cleavage of a restriction site present therein. In these embodiments, D-loops are formed at the target query region with selectivity sufficient to distinguish the target query region from variants that differ therefrom by as few as one nucleotide, according to the methods of the present invention. Before the sample is deproteinized, a cleaving enzyme, such as a restriction endonuclease, is added. Cleavage sites, such as restriction sites, that are within the target query region are complexed within the protein-containing D-loop and are protected from cleavage. Cleavage sites present within the query region of variants that differ from the target by as few as one nucleotide are typically not complexed within protein-containing D-loops, and are thus cleaved.

In other embodiments, formation of the single or double D-loop selectively at the target query region is exploited selectively to alter the methylation state of the target or of the target variants; contact thereafter with a cleaving enzyme, such as a restriction endonuclease, that is sensitive to the methylation state of the duplex effects selective cleavage of target or variants, as desired.

In one such approach, for example, the first and/or second oligonucleotide, is methylated. If the first oligonucleotide is methylated, it is methylated at positions that do not substantially diminish RecA binding and nucleofilament formation.

If the target is unmethylated, the deproteinization-stable single or double D-loop formed at the target will include at least one hemimethylated duplex region. Contact with a restriction endonuclease that is unable to cleave hemimethylated DNA results in selective cleavage of target variants that differ from target by as few as one nucleotide in the query region common therebetween; the target itself is not cleaved. Conversely, contact with a restriction endonuclease that requires hemimethylated DNA results in selective cleavage of the target; variants that differ from target by as few as one nucleotide in the query region common therebetween are not cleaved.

Many restriction enzymes that are sensitive to the presence of methyl groups in various target sequences are known and can be used in such methods, including, for example, AatI, AatII, AccI, AccII, AccIII, Acc65I, AccB7I, AciI, AclI, AdeI, AfaI, AfeI, AflI, AflII, AflIII, AgeI, AhaII, AhdI, AloI, AluI, AlwI, Alw21I, Alw26I, Alw44I, AlwNI, AmaI, AorI, Aor51HI, AosII, ApaI, ApaLI, ApeI, ApoI, ApyI, AquI, AscI, Asp700I, Asp718I, AspCNI, AspMI, AspMDI, AtuCI, AvaI, AvaII, AviII, BaeI, BalI, BamFI, BamHI, BamKI, BanI, BanII, BazI, BbeI, BbiII, BbrPI, BbsI, BbuI, BbvI, BbvCI, Bca77I, Bce243I, BceAI, BcgI, BciVI, BclI, BcnI, BepI, BfiI, Bfi57I, Bfi89I, BfrI, BfuI, BglI, BglII, BinI, BloHI, BlpI, BmaDI, Bme216I, Bme1390I, Bme1580I, BmeTI, BmgBI, BnaI, BoxI, BpiI, BplI, BpmI, BpuI, Bpu10I, Bpu1102I, BsaI, Bsa29I, BsaAI, BsaBI, BsaHI, BsaJI, BsaWI, BsaXI, BscI, BscFI, BseCI, BseDI, BseGI, BseLI, BseMI, BseMII, BseRI, BseSI, BseXI, BsgI, Bsh1236I, Bsh1285I, Bsh1365I, BshGI, BshNI, BshTI, BsiBI, BsiEI, BsiHKAI, BsiLI, BsiMI, BsiQI, BsiWI, BsiXI, BslI, BsmI, BsmAI, BsmBI, BsmFI, BsoBI, BsoFI, Bsp49I, Bsp51I, Bsp52I, Bsp54I, Bsp56I, Bsp57I, Bsp58I, Bsp59I, Bsp60I, Bsp61I, Bsp64I, Bsp65I, Bsp66I, Bsp67I, Bsp68I, Bsp72I, Bsp91I, Bsp105I, Bsp106I, Bsp119I, Bsp120I, Bsp122I, Bsp143I, Bsp143II, Bsp1286I, Bsp2095I, BspAI, BspDI, N.BspD6I, BspEI, BspFI, BspHI, BspJ64I, BspKT6I, BspLI, BspLU11III, BspMI, BspMII, BspPI, BspRI, BspST5I, BspT104I, BspT107I, BspXI, BspXII, BspZEI, BsrBI, BsrBRI, BsrDI, BsrFI, BsrPII, BssHII, BssKI, BssSI, BstI, Bst1107I, BstAPI, BstBI, BstEII, BstEIII, BstENII, BstF5I, BstGI, BstKTI, BstNI, BstOI, BstPI, BstSCI, BstUI, Bst2UI, BstVI, BstXI, BstYI, BstZ17I, Bsu15I, Bsu36I, BsuBI, BsuEII, BsuFI, BsuMI, BsuRI, BsuTUI, BtcI, BtgI, BtrI, BtsI, CacI, Cac8I, CaiI, CauII, CbiI, CboI, CbrI, CceI, CcrI, CcyI, CfoI, CfrI, Cfr6I Cfr9I, Cfr10I, Cfr13I, Cfr42I, CfrBI, CfuI, ClaI, CpeI, CpfI, CpfAI, CpoI, CspI, Csp5I, Csp6I, Csp45I, Csp68KII, CthII, CtyI, CviAI, CviAII, CviBI, M.CviBIII, CviJI, N.CviPII, CviQI, N.CviQXI, CviRI, CviRII, CviSIII, CviTI, DdeI, DpnI, DpnII, DraI, DraII, DraIII, DrdI, DsaV, EaeI, EagI, Eam1104I, Eam1105I, EarI, EcaI, EciI, Ecl136II, EclXI, Ecl18kI, Eco24I, Eco31I, Eco32I, Eco47I, Eco47III, Eco52I, Eco57I, Eco72I, Eco88I, Eco91I, Eco105I, Eco147I, Eco1831I, EcoAI, EcoBI, EcoDI, EcoHI, EcoHK31I, EcoKI, EcoO65I, EcoO109I, EcoPI, EcoP15I, EcoRI, EcoRII, M.EcoRII, EcoRV, EcoR124I, EcoR124II, EcoT22I, EheI, EsaBC3I, EsaBC4I, EsaLHCI, Esp3I, Esp1396I, FauI, FbaI, FnuDII, FnuEI, Fnu4HI, FokI, FseI, FspI, Fsp4HI, GsuI, HaeII, HaeIII, HaeIV, HapII, HgaI, HgiAI, HgiCI, HgiCII, HgiDI, HgiEI, HgiHI, HhaI, HhaII, Hin1I, Hin6I, HinP1I, HincII, HindII, HindIII, HinfI, HpaI, HpaII, HphI, Hpy8I, Hpy99I, Hpy99II, Hpy188I, Hpy188III, HpyAIII, HpyAIV, HpyCH4III, HpyCH4IV, HsoI, ItaI, KasI, KpnI, Kpn2I, KspI, Ksp22I, KspAI, Kzo9I, LlaAI, LlaKR2I, MabI, MaeII, MamI, MbiI, MboI, MboII, MflI, MlsI, MluI, Mlu9273I, Mlu9273II, MlyI, MmeI, MmeII, MnlI, MroI, MscI, MseI, MslI, MspI, M.MspI, MspA1I, MspBI, MspR9I, MssI, MstII, MthTI, MthZI, MunI, MvaI, Mva1269I, MvnI, MwoI, NaeI, NanII, NarI, NciI, NciAI, NcoI, NcuI, NdeI, NdeII, NgoBV, NgoBVIII, NgoCI, NgoCII, NgoFVII, NgoMIV, NgoPII, NgoSII, NgoWI, NheI, NlaIII, NlaIV, NlaX, NmeSI, NmuCI, NmuDI, NmuEI, NotI, NruI, NsbI, NsiI, NspI, NspV, NspBII, NspHI, PacI, PaeI, PaeR7I, PagI, PauI, PdiI, PdmI, Pei9403I, PfaI, Pfl23II, PflFI, PflMI, PleI, Ple19I, PmaCI, PmeI, PmlI, PpiI, PpuMI, PshAI, Psp5II, Psp1406I, PspGI, PspOMI, PspPI, PstI, PsuI, PsyI, PvuI, PvuII, Ral8I, RalF40I, RflFI, RflFII, Rrh4273I, RsaI, RshI, RspXI, RsrI, RsrII, SacI, SacII, SalI, SalDI, SapI, Sau96I, Sau3239I, Sau3AI, SauLPI, SauMI, Sbo13I, ScaI, Scg2I, SchI, ScrFI, SdaI, SduI, SenPI, SexAI, SfaNI, SfiI, SfoI, SfuI, SgfI, SgrAI, SinI, SmaI, SmlI, SnaBI, SnoI, SolI, SpeI, SphI, SplI, SpoI, SrfI, Sru30DI, SscL1I, Sse9I, Sse8387I, SsoI, SsoII, SspRFI, SstI, SstII, Sth368I, StsI, StuI, StyD4I, StyLTI, StyLTIII, StySJI, StySPI, StySQI, TaaI, TaiI, TaqI, TaqII, TaqXI, TfiI, TflI, ThaI, TliI, TseI, Tsp45I, Tsp509I, TspRI, Tth111I, TthHB8I, Van91I, VpaK11BI, VspI, XapI, XbaI, XceI, XcmI, XcyI, XhoI, XhoII, XmaI, XmaIII, XmiI, XmnI, XorII, XspI, and ZanI. Similarly, many enzymes that can be used to methylate the duplex target nucleic acid molecule (methylases) are known, including, for example, M.AacDam, M.AaoHemKP, M.AarAIP, M.AatII, M.AbrI, M.AccI, M.AccIII, M.AciI, M.AclI, M.AflII, M.AflIII, M.AfuHemKP, M.AfuORF1409P, M.AfuORF1715P, M.AfuORF2345P, M.AgeI, M.AhdI, M.AimAI, M.AimAII, M.AloI, M.AluI, M.AlwI, M.Alw26I, M.ApaI, M.ApaLI, M.ApeKHemKP, M.ApeKORF73P, M.ApeKORF446P, M.ApeKORF554P, M.ApeKORF872P, M.ApeKORF1835P, M.ApeKORF2002P, M.ApoI, M.AquI, M.AscI, M.AseI, M.AsiSI, M.AspCNI, M.AthBP, M.AthI, M.AthIII, M.AthIVP, M.AthVP, M.AthVIP, M.AthVIIP, M.AthVIIIP, M.AtuCHemKP, M.AtuCHemK2P, M.AtuCHemK3P, M.AtuCORF8P, M.AtuCORF1453P, M.AtuCORF1997P, M.AvaI, M.AvaII, M.AvaIII, M.AvaIVP, M.AvaV, M.AvaVI, M.AvaVII, M.AvaVIII, M.AvaIX, M.AvrII, M.BabI, M.BalI, M.BamHI, M.BamHII, M.BanI, M.BanII, M.BanIII, M.BbuB31HemKP, M.Bbulp25ORF2P, M.Bbulp25ORF29P, M.Bbulp560RF67P, M.BbvI, M.BbvCIA, M.BbvCIB, M.Bce10987IP, M.BceAIA, M.BceAIB, M.BcgI, M.BchI, M.BclI, M.BcnIA, M.BcnIB, M.BepI, M.BfaIA, M.BfaIB, BfaHemKP, M.BfaORFC113P, M.BfaORFC143P, M.BfaORFC157P, M.BfaORFC196P, M.BfaORFC198P, M.BfaORFC205P, M.BfaORFC223P, M.BfaORFC240P, M.BfiIA, M.BfiIB, M.BfuAIA, M.BfuAIB, M.BglI, M.BglII, M.BhaHemKP, M.BhaORF3508P, M.BhaORF3535P, M.BhaORF4003AP, M.BhaORF4003BP, M.BlpI, M.BmrIA, M.BmrIB, M.BoIIP, M.BolIIP, M.BpmIA, M.BpmIB, M.Bpu10IA, M.Bpu10IB, M.BsaIA, M.BsaIB, M.BsaAI, M.BsaJI, M.BsaWI, M.BscGIA, M.BscGIB, M.Bse634I, M.BseCI, M.BseDI, M.BseMII, M.BseRIA, M.BseRIB, M.BseYI, M.BsgIA, M.BsgIB, M.BslI, M.BsmIA, M.BsmIB, M.BsmAI, M.BsmBI, M.BsoBI, M.Bsp6I, M.Bsp98I, M.BspCNIA, M.BspCNIB, M.BspHI, M.BspLU11IIIA, M.BspLU11IIIB, M.BspLU11IIIC, M.BspMIA, M.BspMIB, M.BspRI, M.BsrIA, M.BsrIB, M.BsrBIA, M.BsrBIB, M.BsrDIA, M.BsrDIB, M.BsrFI, M.BssHI, M.BssHII, M.BssSI, M.BstF5I, M.BstLVI, M.BstNBI, M.BstNBII, M.BstVI, M.BstYI, M.Bsu36I, M.Bsu168IP, M.Bsu168IIP, M.Bsu168IIIP, M.BsuBI, M.BsuFI, M.BsuRI, M.BusHemKP, M.BusHemK2P, M.Cac824I GCNGC, M.Cac824HemKP, M.Cac824ORF1222P, M.Cac824ORF2309P, M.Cac824ORF3358P, M.Cac824ORF3534AP, M.Cac824ORF3534BP, M.CauJHemKP, M.CauJORFC101P, M.CauJORFC102P, M.CauJORFC103P, M.CauJORFC104P, M.CauJORFC107P, M.CauJORFC110P, M.CauJORFC111P, M.CauJORFC112P, M.CauJORFC113P, M.CauJORFC114P, M.CauJORFC116P, M.CauJORFC117P, M.CauJORFC119P, M.CcrMI GANTC, M.CcrMHemKP, M.CcrMHemK2P, M.CcrMHemK3P, M.CcrMORF620P, M.CcrMORF1033P, M.CcrMORF3626P, M.Cdi630HemKP, M.Cdi630ORFC636P, M.Cdi630ORFC861P, M.Cdi630ORFC898P, M.Cdi630ORFC633aP, M.Cdi630ORFC633bP, M.CelHemKP, M.CeqI, M.Cfr9I, M.Cfr10I, M.CfrBI, M.CglI, M.ChuAHemKP, M.ChuAORFC123P, M.ChuAORFC127P, M.CjeI, M.CjeNHemKP, M.CjeNORF31P, M.CjeNORF208P, M.CjeNORF690P, M.CjeNORF1051P, M.CjeNORF1553P, M.CmuHemKP, M.CpaIOWAIP, M.CpnAHemKP, M.CpnHemKP, M.CpnJHemKP, M.CsyAIP, M.CsyBIP, M.CtrHemKP, M.CviAI, M.CviAII, M.CviAIIIP, M.CviAIV, M.CviAV, M.CviBI, M.CviBIII, M.CviJI, M.CviPI, M.CviQI, M.CviQIII, M.CviQVP, M.CviQVI, M.CviQVII, M.CviRI, M.CviSI, M.CviSII, M.CviSIII, M.CviSVIP, M.DcaI, M.DcaII, M.DdeI, M.DhaHemKP, M.DhaORFC135P, M.DhaORFC140P, M.DhaORFC141P, M.DhaORFC512P, M.DmeORFAP, M.DmeORFBP, M.DnoIP, M.DpnIIA, M.DpnIIB, M.DraIII, M.DraRHemKP, M.DraRORFB138P, M.DraRORFC20P, M.DreIP, M.DsaV, M.EaeI, M.EagI, M.EarIA, M.EarIB, M.EcaI, M.Ecl18kI, M.Eco31I, M.Eco47I, M.Eco47II, M.Eco56I, M.Eco57IA, M.Eco57IB, M.Eco72I, M.EcoAI, M.EcoBI, M.Eco67Dam, M.EcoEI, M.EcoHK31I, M.EcoKI, M.EcoKIIP, M.EcoK12AhemKP, M.EcoKDam, M.EcoKDcm, M.EcoKHemKP, M.EcoKO157DamP, M.EcoKO157DcmP, M.EcoKO157HemKP, M.EcoKO157HemK2P, M.EcoKO157HemK3P, M.EcoKO157ORF1196P, M.EcoKO157ORF1780P, M.EcoKO157ORF2981P, M.EcoKO157ORF4134P, M.EcoKO157ORF5307P, M.EcoNI, M.EcoN15ORF52P, M.EcoN15ORF58P, M.EcoO109I, M.EcoO157IP, M.EcoO157DamP, M.EcoO157DcmP, M.EcoO157HemKP, M.EcoO157HemK2P, M.EcoO157HemK3P, M.EcoO157HemK4P, M.EcoO157ORF1454P, M.EcoO157ORF2060P, M.EcoO157ORF2389P, M.EcoO157ORF3349P, M.EcoO157ORF4622P, M.EcoO1570RF5947P, M.EcoPI, M.EcoP15I, M.EcoP1Dam, M.EcoRI, M.EcoRII, M.EcoRV, M.EcoR9I, M.EcoR124I, M.EcoR124II, M.EcoT1Dam, M.EcoT2Dam, M.EcoT4Dam, M.EcoVIII, M.EcoVT2Dam, M.Eco933WdamP, M.Eco29kI, M.EcoprrI, M.EfaAHemKP, M.EfaAORFC149P, M.EfaAORFC151P, M.EfaAORFC154P, M.EfaORFAP, M.EfaORFC154P, M.EniIP, M.EsaBC1I, M.EsaBC2I, M.EsaBC3I, M.EsaBC4I, M.EsaBS1I, M.EsaBS2I, M.EsaDix1I, M.EsaDix2I, M.EsaDix3I, M.EsaDix4I, M.EsaDix5I, M.EsaDix6I, M.EsaDix7I, M.EsaLHCI, M.EsaLHCII, M.EsaLHCIII, M.EsaLHC2I, M.Esp3I, M.FacHemKP, M.FacHemK2P, M.FacORFC156P, M.FacORFC157AP, M.FacORFC157BP, M.FacORFC158P, M.FacORFC160P, M.FauI, M.FnuDI, M.Fnu4HI, M.FokI, M.FseI, M.FspI, M.Fsp7605IP, M.Fvi3I, M.GgaI, M.GshIP, M.GsuI, M.H2I, M.HaeII, M.HaeIII, M.HaeIV, M.HgaIA, M.HgaIB, M.HgiBI, M.HgiCI, M.HgiCII, M.HgiDI, M.HgiDII, M.HgiEI, M.HgiGI, M.HhaI, M.HhaII, M.HinHP1Dam, M.HinP1I, M.HincII, M.HindI, M.HindII, M.HindIII, M.HindIV, M.HindV, M.HindHemKP, M.HindHemK2P, M.HindORF1056P, M.HindORF1286P, M.HinfI, M.HpaI, M.HpaII, M.HphIA, M.HphIB, M.HpyI, M.Hpy8I, M.Hpy99I, M.Hpy99II, M.Hpy99III, M.Hpy99IV, M.Hpy99VA, M.Hpy99VBP, M.Hpy99VI, M.Hpy99VII, M.Hpy99VIII, M.Hpy99IX, M.Hpy99X, M.Hpy99XI, M.Hpy166DP, M.Hpy166EP, M.Hpy166FP, M.Hpy166IVP, M.Hpy178IP, M.Hpy188I, M.Hpy188II, M.Hpy188III, M.HpyAI, M.HpyAIIA, M.HpyAIIB, M.HpyAIII, M.HpyAIV, M.HpyAV, M.HpyAVIA, M.HpyAVIB, M.HpyAVII, M.HpyAVIII, M.HpyAIX, M.HpyAX, M.HpyAXI, M.HpyAHemKP, M.HpyAORF263P, M.HpyAORF369P, M.HpyAORF463P, M.HpyAORF481P, M.HpyAORF483P, M.HpyAORF850P, M.HpyAORF1354P, M.HpyAORF1370P, M.HpyAORF1403P, M.HpyAORF1472P, M.HpyAORF1517P, M.HpyAORF1522P, M.HpyCH4IV, M.HpyCH4V, M.Hpy166GP, M.Hpy166HP, M.Hpy99HemKP, M.Hpy99ORF415P, M.Hpy99ORF430P, M.Hpy99ORF433P, M.Hpy99ORF613P, M.Hpy99ORF786P, M.Hpy99ORF846P, M.Hpy99ORF1012P, M.Hpy99ORF1284P, M.Hpy99ORF1296P, M.Hpy99ORF1365P, M.Hpy99ORF1409P, M.Hpy99ORF1411P, M.Hpy99ORF1423P, M.HsaIB, M.HsaIIP, M.HsaIIIA, M.HsaIIIB, M.HsaIVP, M.HsaHemKP, M.HsaHemK2P, M.HspNIP, M.HspNHemKP, M.HspNORF106P, M.HspNORF1543P, M.HspNORF2242P, M.HspNORF6135AP, M.HspNORF6135BP, M.KpnI, M.Kpn2I, M.KpnAI, M.LdvIP, M.LesIP, M.LinHemKIP, M.LlaI, M.Lla82I, M.Lla1403I, M.Lla2009IP, M.Lla2614I, M.LlaAIA, M.LlaAIB, M.LlaBI, M.LlaBIIP, M.LlaBIII, M.LlaCI, M.LlaDII, M.LlaDCHIA, M.LlaDCHIB, M.LlaFI, M.LlaGI, M.Lla1403HemKP, M.LlaKR2I, M.Lla509ORFAP, M.LlaPI, M.LldI, M.LmoA118I, M.Lsp1109I, M.MamI, M.MarMIP, M.MbaHemKP, M.MbaORFC198P, M.MbaORFC203P, M.MbaORFC206P, M.MbaORFC207P, M.MbaORFC531P, M.MbaORFC533P, M.MboIA, M.MboIB, M.MboIIA, M.MboIIB, M.MboAHemKP, M.MboAORFC210P, M.MboAORFC263P, M.MboAORFC271P, M.Mca27343I, M.MfeI, M.MgeHemKP, M.MgeORF184P, M.MgrIP, M.MjaI, M.MjaII, M.MjaIII, M.MjaIVP, M.MjaV, M.MjaVI, M.MjaHemKP, M.MjaORF132P, M.MjaORF563P, M.MjaORF1200P, M.MjaORF1220P, M.MjaORFCL42P, M.MleHemKAP, M.MleHemKBP, M.MleSHemKP, M.MleSORF756P, M.MloHemKP, M.MloORFmll9056P, M.MloORFmll9333P, M.MloORFmlr7520P, M.MloORFmlr7992P, M.MloORFmlr8517P, M.MluI, M.MlyI, M.MmaMHemKP, M.MmaMHemK2P, M.MmaMHemK3P, M.MmaMORF527P, M.MmaMORFC170P, M.MmaMORFC174P, M.MmaMORFC175AP, M.MmaMORFC175BP, M.MmaMORFC525P, M.MmaMORFC527P, M.MmuI, M.MmuIIP, M.MmuIIIA, M.MmuIIIB, M.MmyIP, M.MneAORF1590P, M.MnlIA, M.MnlIB, M.MpnIP, M.MpnHemKP, M.MpnORFDP, M.MpuCHemKP, M.MpuCORF430AP, M.MpuCORF430BP, M.MpuCORF810AP, M.MpuCORF810BP, M.MpuCORF1850AP, M.MpuCORF1850BP, M.MpuCORF3960P, M.MpuCORF3970P, M.MpuCORF3980P, M.MpuCORF4330P, M.MpuCORF4800P, M.MpuCORF6780P, M.MpuCORF6880P, M.MpuUI, M.MsaRVIP, M.MsaV2IP, M.MsaV3IP, M.MsaV4IP, M.MseI, M.MspI, M.MspA1I, M.MspMCHemKP, M.MspMCHemK2P, M.MspMCHemK3P, M.MspMCORFC183P, M.MspMCORFC184P, M.MspMCORFC186P, M.MspMCORFC187AP, M.MspMCORFC187BP, M.MthHHemKP, M.MthHORF495P, M.MthHORF724P, M.MthHORF942P, M.MthTI, M.MthZI, M.MtuCTHemKP, M.MtuCTORF2076P, M.MtuCTORF2082P, M.MtuCTORF2826P, M.MtuCTORF3363P, M.MtuHHemKP, M.MtuHORF2756P, M.MtuHORF3263P, M.MunI, M.MvaI, M.MwoI, M.NaeI, M.NarAORFC306P, M.NcoI, M.NcrNI, M.NdeI, M.NeuHemKP, M.NeuORFC215AP, M.NeuORFC215BP, M.NeuORFC218P, M.NeuORFC219P, M.NgoBI, M.NgoBIIP, M.NgoBV, M.NgoBVIIIA, M.NgoBVIIIB, M.NgoFVII, M.NgoLII, M.NgoLHemKP, M.NgoMIV, M.NgoMX, M.NgoMXV, M.NgoMorf2P, M.NgoPII, M.NgoSII, M.Ngo125VIIP, M.NheI, M.NlaIII, M.NlaIV, M.NlaX, M.NmeAHemKP, M.NmeAHemK2P, M.NmeAORF59P, M.NmeAORF191P, M.NmeAORF427P, M.NmeAORF532P, M.NmeAORF561P, M.NmeAORF1035P, M.NmeAORF1038P, M.NmeAORF1385P, M.NmeAORF1432P, M.NmeAORF1453P, M.NmeAORF1467P, M.NmeAORF1500P, M.NmeAORF1590P, M.NmeBIA, M.NmeBIB, M.NmeBF13P, M.NmeBHemKP, M.NmeBHemK2P, M.NmeBORF76P, M.NmeBORF826P, M.NmeBORF829P, NmeBORF1033P, M.NmeBORF1223P, M.NmeBORF1261P, M.NmeBORF1290P, M.NmeBORF1375P, M.NmeB1940ORF1P, M.NmeDIP, M.Nme2120ORF1P, M.NmeSI, M.NmeST1117ORF1P, M.NotI, M.NpuHemKP, M.NpuORFC221P, M.NpuORFC222P, M.NpuORFC224P, M.NpuORFC226P, M.NpuORFC227P, M.NpuORFC228P, M.NpuORFC229P, M.NpuORFC230P, M.NpuORFC231P, M.NpuORFC232P, M.NpuORFC234P, M.NpuORFC237P, M.NpuORFC242P, M.NspI, M.NspIII, M.NspV, M.NspHI, M.OkrAI, M.OsaIP, M.PabHemKP, M.PabORF588P, M.PabORF1205P, M.PabORF1283P, M.PabORF2149P, M.PabORF2246P, M.PabORF2317P, M.Pac25I, M.PaePAHemKP, M.PaePAHemK2P, M.PaePAHemK3P, M.PaePAHemK4P, M.PaePAORF370P, M.PaePAORF2735P, M.PaeR7I, M.PcopB4P, M.PflMI, M.PflPHemKP, M.PflPHemK2P, M.PflPHemK3P, M.PflPHemK4P, M.PfuAIP, M.PgiI, M.PhaAI, M.PhaBI, M.PhiBssHII, M.PhiCh1I, M.PhiGIP, M.PhiHIAP, M.PhiHIBP, M.PhiHII, M.PhiMx8I, M.Phi3TI, M.Phi3TII TCGA, M.PhoHemKP, M.PhoORF39P, M.PhoORF338P, M.PhoORF584P, M.PhoORF905P, M.PhoORF1032P, M.PhoORF1948P, M.PleI, M.PliMCI, M.PmaMEDHemKP, M.PmuDamP, M.PmuHemKP, M.PmuHemK2P, M.PmuHemK3P, M.PmuORF698P, M.PmuORF1537P, M.Ppu21I, M.ProHemKP, M.ProORFC262P, M.PsaI, M.PshAI, M.PspGI, M.PspPI, M.PstI, M.PstII, M.PvuII, M.QpaIP, M.RcoHemKP, M.RcoORF690P, M.RcoORF1350P, M.RhmIP, M.Rho11sI, M.RhvI, M.Rle39BI, M.RmeADamP, M.RmeAHemKP, M.RmeAHemK2P, M.RmeAORFC243P, M.RmeAORFC246P, M.RnoIP, M.RpaORFC296AP, M.RpaORFC296BP, M.RpaORFC298P, M.RpaORFC302P, M.RpaORFC303P, M.RprHemKP, M.RsaI, M.RshYP, M.RshXP, M.RspAIP, M.RspDORFC282AP, M.RspDORFC282BP, M.RspDORFC283P, M.RspDORFC285P, M.RspDORFC291P, M.RsrI, M.SPBetaI, M.SPRI, M.SacI, M.SacII, M.SalI, M.SapIA, M.SapIB, M.Sau42I, M.Sau96I, M.Sau3AI, M.SauMu50HemKP, M.SauMu50ORF431P, M.SauMu50ORF1808P, M.SauN315HemKP, M.SauN315ORF391P, M.SauN315ORF1626P, M.ScaI, M.SceHemKP, M.SciSpV1P, M.ScoA3HemKP, M.ScrFIA, M.ScrFIB, M.SenPI, M.SeqHemKP, M.SeqORFC20AP, M.SeqORFC20BP, M.SeqORFC57P, M.SeqORFC175P, M.SeqORFC272P, M.SeqORFC395P, M.SeqORFC448P, M.SfiI, M.SfoI, M.SgrAI, M.SinI, M.SmaI, M.SmaII, M.SmeIP, M.SmeHemK1P, M.SmeHemK2P, M.SmeORF2296P, M.SmeORF3763P, M.SnaBI, M.SobIP, M.SpeI, M.SphI, M.Spn526IP, M.Spn5252IP, M.SpnHemKP, M.SpnORF505P, M.SpnORF886P, M.SpnORF1221P, M.SpnORF1336P, M.SpnORF1431P, M.SpnRHemKP, M.SpnRHemK2P, M.SpnRORF449P, M.SpnRORF790P, M.SpnRORF1101P, M.SpnRORF1287P, M.SpnRORF1665P, M.SpomI, M.SpomHemKP, M.SprHemKP, M.SpyHemKP, M.SpyORF1077P, M.SpyORF1906P, M.Sse9I, M.SsfORF265P, M.SsoI, M.SsoII, M.SspI, M.Ssp6803I, M.Ssp6803HemKP, M.Ssp6803ORF729P, M.Ssp6803ORF1803P, M.SssI, M.Ssu2479IA, M.Ssu2479IB, M.Ssu4109IA, M.Ssu4109IB, M.Ssu4961IA, M.Ssu4961IB, M.Ssu8074IA, M.Ssu8074IB, M.Ssu11318IAP, M.Ssu11318IBP, M.SsuDAT1IA, M.SsuDAT1IB, M.Sth368I, M.SthER35IP, M.SthSfi1ORF535P, M.SthSt0IP, M.SthSt8IP, M.StoHemKP, M.StoORF335P, M.StsI, M.StyCORFAP, M.StyD4I, M.StyDam, M.StyDcmIP, M.StyLTI, M.StyLTIII, M.StyLT2DamP GATC, M.StyLT2DcmP, M.StyLT2FelsDamP, M.StyLTHemKP, M.StyLT2HemKP, M.StyLT2HemK2P, M.StyLT2ORF357P, M.StyLT2ORF3386P, M.StyLT2ORF4525P, M.StyR27ORF41P, M.StyR27ORF43P, M.StyR27ORF154P, M.StySBLI, M.StySBLIIP, M.StySJI, M.StySKI, M.StySPI, M.SwaI, M.TaqI TCGA, M.TfiI GAWTC, M.TfuORFC321AP, M.TfuORFC321BP, M.TfuORFC325P, M.TfuORFC327P, M.ThaI, M.ThaHemKP, M.ThaHemK2P, M.ThaORF318P, M.ThaORF644P, M.ThaORF1168P, M.ThaORF1336AP, M.ThaORF1336BP, M.ThaORF1417P, M.TliI, M.TmaI, M.TmaHemKP, M.TpaI, M.TpaHemKP, M.TseI, M.Tsp45I, M.Tsp509I, M.TspRI, M.Tth111I, M.TthHB8I, M.TvoORF124AP, M.TvoORF124BP, M.TvoORF442P, M.TvoORF681P, M.TvoORF725P, M.TvoORF849P, M.TvoORF1192P, M.TvoORF1400P, M.TvoORF1413P, M.TvoORF1416P, M . TvoORF1436P, M.UurHemKP, M.UurORF98P, M.UurORF100P, M.UurORF477P, M.UurORF528P, M.Van91II, M.Vch01IP, M.VchADamP, M.VchAHemKP, M.VchAHemK2P, M.VchAORF198P, M.VchAORF1769P, M.VspI, M.XamI, M.XbaI, M.XcmI, M.XcyI, M.XfaAORFC332P, M.XfaAORFC333P, M.XfaAORFC340P, M.XfaHemKP, M.XfaHemK2P, M.XfaORF297P, M.XfaORF641P, M.XfaORF935P, M.XfaORF1774P, M.XfaORF1804P, M.XfaORF1968P, M.XfaORF2297P, M.XfaORF2313P, M.XfaORF2723P, M.XfaORF2724P, M.XfaORF2728P, M.XfaORF2742P, M.XhoI, M.XhoII, M.XlaI, M.XmaI, M.XmaXhI, M.XmnI, M.XorII, M.YpeIP, M.ZmaI, M.ZmaIIA, M.ZmaIII, M.ZmaV, and M.ZmaORFAP.

In another methylation-based approach, analogous to the Achilles' heel cleavage approach described in Szybalski, Curr. Opin. Biotechnol. 8:75-81 (1997) and Ferrin et al., Science 254:1494-7 (1991), single or double D-loops are formed at the target query region, depending on target topology; in accordance with the methods of the present invention, D-loops are formed with selectivity sufficient to distinguish target from variants that differ by as few as one nucleotide therefrom within a query region common therebetween. Before deproteinization, a methyltransferase, such as EcoRI methylase, is added. Methylation sites that are within the target query region are complexed within the protein-containing D-loop and are protected from methylation. Methylation sites within variants that differ from target by as few as one nucleotide in the common query region are not so protected, and are subject to methylation.

The sample is deproteinized and contacted with a cleaving enzyme. Contact with a cleaving enzyme, such as a restriction endonuclease, that preferentially cleaves methylated sequences cleaves variants, not target; contact with an endonuclease that preferentially cleaves unmethylated DNA leads to target cleavage.

In embodiments in which the sample is methylated, demethylase enzymes may be employed in the converse of the above-described approach.

In another approach, single or double D-loops, depending on target topology, are formed at the target query region with selectivity sufficient to discriminate variants that differ from target by as few as one nucleotide; the single or double D-loop are used to generate one or more specific cleavage sites that thus appear exclusively within the target.

In these embodiments, type IIs restriction endonucleases are particularly useful.

Type IIs restriction enzymes have distinct DNA binding and cleavage domains; therefore, they recognize a specific sequence but cleave a defined distance away. For example, the Type IIs restriction enzyme, FokI, binds to a site containing the sequence GGATG and cleaves 9 and 13 base pairs away from the recognition site in a staggered fashion.

Other Type IIs and Type IIs-like enzymes can be used including, for example, restriction enzyme StsI, Group I intron homing endonuclease I-TevI, R2 retrotransposon endonuclease R2, P1 transposase SCEI and bacterial recombination RecBCD. Other homing endonucleases include, for example, F-SceI, F-SceII, F-SuvI, F-TevI, F-TevII, I-AmaI, I-AniI, I-BmoI, I-CeuI, I-CeuAIIP, I-ChuI, I-CmoeI, I-CpaI, I-CpaII, I-CreI, I-CrepsbIP, I-CrepsbIIP, I-CrepsbIIIP, I-CrepsbIVP, I-CsmI, I-CvuI, I-CvuAIP, I-DdiI, I-DdiII, I-DirI, I-DmoI, I-HmuI, I-HmuII, I-HspNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PpbIP, I-PpoI, I-SPBetaIP, I-ScaI, I-SceI, I-SceII, I-SceIII, I-SceIV, I-SceV, I-SceVI, I-SceVII, I-SexIP, I-SneIP, I-SpomCP, I-SpomIP, I-SpomIIP, I-SquIP, I-Ssp6803I, I-SthPhiJP, I-SthPhiST3P, I-SthPhiS3bP, I-TdeIP, I-TevI, I-TevII, I-TevIII, I-UarAP, I-UarHGPA1P, I-UarHGPA13P, I-VinIP, I-ZbiIP, PI-MgaI, PI-MtuI, PI-MtuHIP, PI-MtuHIIP, PI-PfuI, PI-PfuII, PI-PkoI, PI-PkoII, PI-PspI, PI-Rma43812IP, PI-SPBetaIP, PI-SceI, PI-TfuI, PI-TfuII, PI-ThyI, PI-TliI, and PI-TliII.

Type IIB restriction enzymes that cleave on both sides of the binding site may also be used, such as BcgI and BplI.

In one series of embodiments, a recognition site for a Type IIs, Type IIs-like or Type IIB restriction enzyme is formed by an extension on either or both of the first and second oligonucleotides; within the single or double D-loop (depending upon target topology), the extension folds back on the respective oligonucleotide, forming a double-stranded portion containing the recognition site.

Alternatively, a recognition site for a Type IIs, Type IIs-like or Type IIB restriction enzyme can be formed by recognition regions within the first and second oligonucleotides; the recognition regions are situated outside the regions of complementarity to target, and are complementary therebetween.

In yet other approaches, a cleavage moiety or peptide having nonspecific endonucleolytic activity is targeted to and cleaves the target. The cleavage moiety or peptide may be linked directly to the first or second oligonucleotide or may be linked thereto through a specific binding pair interaction, such as a biotin-streptavidin interaction. Examples of such an endonucleolytic moiety include, for example, EDTA-Fe$^{II}$ (for iron/EDTA facilitated cleavage), non-specific phosphodiesterases, and non-specific restriction endonucleases.

In yet other approaches, the single or double D-loop may be cleaved with a single-strand specific endonuclease, for example, S1 nuclease, or a resolvase that recognizes the double D-loop structure, such as the MRE11.

Selective cleavage of target variants by any of the above-described methods may be used to deplete samples of such variants, either as a complement to affirmative separation of the target, or alone. Selective cleavage finds particular use when the target and variants thereof are present within replicable vectors, and reduces the percentage of contaminating variants in subsequent host cell transformations.

Selective cleavage may also be used to facilitate selective cloning of targets, such as cloning of specific allelic variants of a gene of interest.

In certain of these embodiments, at least two D-loops (either single or double, depending upon target topology) are formed on the target nucleic acid: the first D-loop, as described above, is formed at the query region with selectivity sufficient to distinguish the target from variants that differ in the common query region by as few as one nucleotide therefrom; the second D-loop is formed at a second site distant thereto.

Applying one of the selective cleavage methods set forth above, cleavage is effected at the first site and at the second site. With formation selectively at the target query region, fragments unique to the target are obtained.

Such unique fragments also permit the detection of targets and/or variants thereof by restriction fragment length polymorphism analysis.

In another series of such embodiments, selective cleavage is used to prevent subsequent amplification. In embodiments in which variants are selectively cleaved, target can be amplified with selectivity sufficient to distinguish target from variants that differ by as few as one nucleotide therefrom. Amplification may be according to the D-loop methods above-described, or may instead be methods that do not rely upon D-loop formation, such as polymerase chain reaction (PCR), nucleic acid sequence-based amplification (NASBA), self-sustained sequence recognition (3SR), ligase chain reaction (LCR), transcription-mediated amplification (TMA), rolling circle amplification (RCA), and strand displacement amplification (SDA).

The methods of the present invention may further comprise the additional step of quantifying the abundance of target. Abundance may be measured as absolute abundance of target within a nucleic acid sample or as abundance relative to one or more additional targets and/or target variants.

Absolute abundance of a target within a sample may, for example, usefully signal the presence or absence of an allelic variant associated with a defined phenotype, such as predisposition to or presence of a disease. Absolute abundance of one or more targets within a sample may additionally be used to categorize or identify a sample, as in forensic applications.

To measure relative abundance of a target, it is useful to be able to detect a plurality of targets and/or variants within a single sample.

The ability distinguishably to detect a plurality of targets (or target variants) within a single sample also finds use in generating comprehensive haplotypes or genotypes from individual samples for prognostic, diagnostic, or monitoring purposes; in screening large numbers of loci in a plurality of individuals to associate genotypes with phenotypes of interest; and as a way to increase genotyping throughput and lower costs per interrogated locus.

Accordingly, in another aspect, the invention provides a method of distinguishably detecting the presence of a plurality of nonsupercoiled targets within a sample of nucleic acids with selectivity sufficient to distinguish each of the plurality of targets from variants that respectively differ by as few as one nucleotide therefrom at a query region that is common therebetween.

The method comprises using a recombinase to mediate formation, separately for each of the plurality of targets desired to be detected, of at least one deproteinization-stable double D loop in the target's query region, under conditions that favor double D loop formation at the target query region over formation at variants that differ from the target by as few as one nucleotide therefrom, each target's double D-loop being distinguishably detectable from all others of the double D-loops formed in the sample; and then distinguishably detecting each of the stable double-D loops so formed.

In this aspect of the invention, conditions typically comprise contacting the sample, for each of the plurality of targets desired to be detected, with a first oligonucleotide and a second oligonucleotide. The first oligonucleotide includes a complementarity region that is perfectly complementary in sequence to a first strand of its respective target across the entirety of the target query region, the second oligonucleotide includes a complementarity region that is perfectly complementary in sequence to a second strand of the same target across at least a portion of the target query region, and either or both of the oligonucleotide regions is imperfectly complementary in sequence to respective first and second strands of the query region of each of the other targets desired discriminably to be detected.

The first oligonucleotide is bound by a recombinase and the second oligonucleotide comprises base modifications and does not substantially bind the recombinase, and at least one of the first and second oligonucleotides is distinguishable from the first and second oligonucleotides used to detect each of the others of the plurality of targets desired to be detected.

Analogously, in another aspect the invention provides methods of distinguishably detecting the presence of a plurality of supercoiled targets within a sample of nucleic acids with selectivity sufficient to distinguish each of the plurality of targets from variants that respectively differ by as few as one nucleotide therefrom at a query region that is common therebetween.

The method comprises using a recombinase to mediate formation, separately for each of the plurality of targets desired to be detected, of at least one deproteinization-stable single D-loop or double D-loop in the target's query region, under conditions that favor single D-loop or double D-loop formation at the target query region over formation at variants that differ from the target by as few as one nucleotide therefrom, each target's single or double D-loop being distinguishably detectable from all others of the D-loops formed in said sample; and then distinguishably detecting each of the stable double-D loops so formed.

Typically, the formation conditions comprise contacting the sample, for each of the plurality of targets desired to be detected, with a first oligonucleotide, wherein the first oligonucleotide includes a complementarity region that is perfectly complementary in sequence to a first strand of its respective target across the entirety of the target query region and is imperfectly complementary in sequence to a first strand of the query region of each of the other targets desired discriminably to be detected.

The first oligonucleotide is bound by a recombinase and is distinguishable from the first oligonucleotide used to detect each of the others of the plurality of targets desired to be detected.

The method may further comprise contacting the sample, for each of the plurality of targets desired to be detected, with a second oligonucleotide.

For each of the plurality of targets desired to be detected, the second oligonucleotide comprises base modifications and does not substantially bind said recombinase. The second oligonucleotide includes a complementarity region that is perfectly complementary in sequence to a second strand of the target across at least a portion of the target query region, and at least one of the first and second oligonucleotide complementarity regions is imperfectly complementary to the respective strand of the query region of each of the target variants. The second oligonucleotide is distinguishably detectable.

The plurality of single or double D-loops in the multiplexed aspects of the present invention may be formed concurrently or seriatim, and the D loops so formed may be detected concurrently or seriatim.

Methods well suited for concurrent detection include microarray detection, including detection of oligonucleotide-associated bar code tags using a microarray having tag complements, Shoemaker et al., *Nature Genet.* 14(4):450-6 (1996); EP 0799897; Fan et al., *Genome Res.* 10:853-60 (2000); and U.S. Pat. No. 6,150,516, the disclosures of which are incorporated herein by reference in their entireties.

As used herein, the term "microarray" and the equivalent phrase "nucleic acid microarray" refer to a substrate-bound collection of plural nucleic acids, hybridization to each of the plurality of bound nucleic acids being separately detectable. The substrate can be solid or porous, planar or non-planar, unitary or distributed. As so defined, the term "microarray" and phrase "nucleic acid microarray" include all the devices so called in Schena (ed.), *DNA Microarrays: A Practical Approach* (*Practical Approach Series*), Oxford University Press (1999) (ISBN: 0199637768); *Nature Genet.* 21(1) (suppl):1-60 (1999); and Schena (ed.), *Microarray Biochip: Tools and Technology*, Eaton Publishing Company/BioTechniques Books Division (2000) (ISBN: 1881299376), the disclosures of which are incorporated herein by reference in their entireties.

The term "microarray" and phrase "nucleic acid microarray" also include substrate-bound collections of plural nucleic acids in which the plurality of nucleic acids are distributably disposed on a plurality of beads, rather than on a unitary planar substrate, as is described, inter alia, in Brenner et al., *Proc. Natl. Acad. Sci. USA* 97(4):166501670 (2000), the disclosure of which is incorporated herein by reference in its entirety; in such case, the term "microarray" and phrase "nucleic acid microarray" refer to the plurality of beads in aggregate. The term "microarray" and phrase "nucleic acid microarray" also include substrate-bound collections of plural nucleic acids in which the plurality of nucleic acids are incorporated within a gel, as is described, inter alia, in U.S. Pat. No. 6,174,683, the disclosure of which is incorporated herein by reference in its entirety.

The plurality of single or double D-loops may also be detected concurrently using mass tags and mass spectrometry, typically time of flight mass spectrometry.

The plurality of targets to be distinguishably detected may include a plurality of targets that differ from one another at a query region common thereamong by as few as one nucleotide. The targets may differ from one another by 2, 3, 4, 5, 6, 7, 8, 9, even 10 nucleotides in a common query region. Such targets desired concurrently to be detected may differ in a common query region by no more than 9, 8, 7, 6 and even by no more than 5 nucleotides. In some embodiments, the targets desired concurrently and distinguishably to be detected differ in a common query region by 1, 2, 3, 4, or 5 nucleotides.

Such targets may be naturally-occurring allelic variants, separate members of a gene family, or recombinantly engineered variants of a single progenitor nucleic acid.

Additionally, or in the alternative, the plurality of targets to be distinguishably detected may include a plurality of unrelated targets. Such targets may, for example, be separate and discrete loci present in a common genome.

The plurality of targets distinguishably to be detected may include as few as 2, 3, 4, or 5 targets, and may include 10, 20, 30, 40, or even 50 or more targets. The plurality of targets distinguishably to be detected may include as many as 100 targets, 250 targets, 500 targets, even as many as 1,000, 2,000, 3,000, 4,000, or 5,000 or more targets. Even as many as 10,000 to 100,000 targets may be distinguishably detected.

As noted above, the methods of this aspect of the invention may further include the step of quantifying the abundance of one or more of the targets within the sample.

The relative abundance of allelic variants within a population—including single nucleotide polymorphisms and haplotypes comprising a plurality of variants at multiple loci—may be used, for example, to associate genotypes with phenotypes of interest. Such phenotypes include monogenic and polygenic diseases, or predispositions thereto.

In a single individual, the relative abundance of a particular variant at a particular locus, as compared to the abundance of a target at another locus, may be used e.g. to diagnose loss of heterozygosity, and thus the presence of a clonal subpopulation of transformed cells in a biological sample, which can be diagnostic of the presence of a cancerous or precancerous lesion.

In one series of such embodiments, the invention permits detection of a trace amount of DNA derived from neoplastic or preneoplastic cells in a biological sample containing a majority of wild type DNA or whole cells.

In these embodiments, the invention comprises the comparative measurement of two genomic sequences. One genomic sequence is stable through transformation—that is, it is identical in both malignant and wild type cells in the sample. A second genomic sequence typically undergoes change during the course of transformation—that is, it is mutated or lost during the development of malignant precursor cells. The relative abundance of the sequences is determined: if a statistically significant difference in abundance is observed, diagnosis may be made.

Statistical methods for determining significance of abundance differences are described in U.S. Pat. No. 5,670,325, the disclosure of which is incorporated herein by reference in its entirety.

For detection of colorectal carcinoma and precancerous colonic lesions, the sample is usefully a stool sample voided by a patient. Methods for physical preparation of stool samples for genetic detection are disclosed in U.S. Pat. Nos. 5,670,325 and 6,303,304, the disclosures of which are incorporated herein by reference in their entireties.

In other embodiments, the first and second genomic samples may be maternal and paternal alleles of a single locus of a heterozygous individual. A statistically different abundance of one of the two alleles can indicate loss of heterozygosity, and the presence of a clonal subpopulation of transformed cells.

Genes for which loss of heterozygosity has been implicated in the etiology of one or more human cancers, and which are thus usefully assayed using these embodiments of the methods of the present invention, include p53, DCC, APC, CDK2AP1, DBCCR1, DDX26, DEC, DEC1, DLC1, DLEC1, DLEU1, DLEU2, DMBT1, DNB5, DOC-1R, DSS1, RERE (nomenclature pursuant to CancerGene database, Infobiogen, France: http://caroll.vjf.cnrs.fr/cancer-gene/HOME.html).

In another aspect, the invention provides nucleic acid compositions within which nucleic acid targets that differ by as few as a single nucleotide may be distinguished.

In one series of embodiments, the nucleic acid composition is characterized by the presence of at least one deproteinized double D loop at a query region within a nucleic acid target. The deproteinized double D-loop includes a first and a second oligonucleotide.

The first oligonucleotide includes a complementarity region that is perfectly complementary in sequence to a first strand of the target across the entirety of the target query region. The second oligonucleotide includes a complementarity region that is perfectly complementary in sequence to a second strand of the target across at least a portion of the target query region. The first oligonucleotide is bound by a recombinase, the second oligonucleotide comprises base modifications and does not substantially bind the recombinase, and at least one of said first and second oligonucleotides is distinguishably detectable.

The first and second oligonucleotides have the features set forth above in the description of the methods of the present invention, which description is incorporated here by reference in its entirety.

In certain embodiments, the composition further comprises at least one variant that differs from the target by as few as one nucleotide within a query region that is common therebetween; the query region of each of the target variants lacks a double D loop.

In another aspect, the invention provides a nucleic acid composition characterized by the presence of a plurality of deproteinized double D-loops, each of the plurality formed at a query region within a respective nucleic acid target.

Each double D-loop includes a first and a second oligonucleotide. Each first oligonucleotide includes a complementarity region that is perfectly complementary in sequence to a first strand of its respective target across the entirety of the target query region. Each second oligonucleotide includes a complementarity region that is perfectly complementary in sequence to a second strand of its respective target across at least a portion of the target query region.

The first oligonucleotide is bound by a recombinase; the second oligonucleotide comprises base modifications and does not substantially bind said recombinase.

In certain embodiments, at least two of the plurality of targets differ in sequence by at least one, and by fewer than 10 nucleotides as between their respective query regions, including 1, 2, 3, 4, 5, 6, 7, 8, or even 9 nucleotides as between their respective query regions, with a sequence difference of 1-5 nucleotides being typical. In embodiments in which single nucleotide polymorphisms may be distinguished, at least two of the plurality of targets having double D-loops differ by exactly 1 nucleotide as between their respective query regions.

The plurality of targets may include at least 10 targets, 100 targets, 1000 targets, even as many as 10,000 targets or more. The targets may be nonsupercoiled or supercoiled.

In another aspect, the invention provides kits that are useful for performing the methods of the present invention. In some embodiments, the kits provide buffers; and/or wash solutions; and/or detergents useful for removing recombinase, such as SDS; and/or a recombinase such as RecA, modified RecA or a yeast, human or mammalian analog of RecA; and/or annealing and/or incoming oligonucleotides; and/or positive and/or negative control samples; and/or instructions.

The following examples are offered by way of illustration and not by limitation.

EXAMPLE 1

General Protocols for Formation and Detection of Double D-Loops and Y-Arms

Formation of double D-loops. Typically, we form double D-loops or Y-arms (Y-arms are D-loops formed at the end of a duplex target; hereinafter, unless otherwise dictated by context, the term D-loop includes Y-arms) by combining the following in a 7 µl reaction so that the final concentration in 10 µl is: 80 nM of the first or "incoming" oligonucleotide; 2.5 µM *Escherichia coli* RecA protein; 1.0 mM ATP-γ-S; 25 mM Tris-acetate, pH 6.8; 1 mM dithiothreitol; and 1 mM magnesium acetate. This reaction is incubated for 10 minutes at 37° C. to allow for binding of RecA protein to the oligonucleotide ("presynapsis", see FIG. 1 for an outline of the method).

We then add double-stranded nucleic acid target, which is generally $^{32}$P-end-labeled using T4 polynucleotide kinase to facilitate detection of the complex, at a concentration of approximately 20 nM and 10 mM magnesium acetate to a final volume of 10 µl. We incubate this reaction for 10 minutes at 37° C. to allow for synapsis between to the incoming oligonucleotide and the target nucleic acid molecule. We then add the second or "annealing" oligonucleotide in 1 µl to a concentration of 640 nM (calculated for the original 10 µl reaction volume) and incubate for 10 minutes at 37° C. to allow the second oligonucleotide to anneal to the target nucleic acid. We then denature the RecA bound to the oligonucleotide:target complex by cooling the reaction to about 4° C. in an ice bath and adding 1 µl of 10% SDS. The samples are then used immediately or stored at −20° C.

Detection of double D-loops. We may analyze the samples prepared as described above by separating by polyacrylamide gel electrophoresis (PAGE). We dry the gels and detect the $^{32}$P-labeled target duplex nucleic acid by either autoradiography or using a phosphorimager. We monitor the formation of the double D-loops under these assay conditions by detecting the retarded migration of the labeled nucleic acid in the gel: the labeled target nucleic acid in double D-loops migrates more slowly than duplex target nucleic acid.

EXAMPLE 2

Double D-Loop Formation Using an Oligonucleotide Comprising LNA

Oligonucleotides used in this example. We employ the protocol described in Example 1 to form double D-loops between two DNA oligonucleotides and linear, duplex target DNA. The target duplex DNA is composed of two linear 70-mer oligonucleotides with sequence complementary to each other. The sequence of the first target strand, designated "OligoA", is: 5'-CTCCGGCCGCTTGGGTGGAGAGGC-TATTCGGCTA<u>C</u>GACTGGGCACAACAGACAATCGGCTGCTCTGATGC-3' (SEQ ID NO: 1) and the sequence of the second target strand, designated "OligoB", is: 3'-GAGGCCGGCGAACCCAC-CTCTCCGATAAGCCGAT GCTGACCCGTGTTGTCTGTTAGCCGACGAGACTACG-5' (SEQ ID NO: 2). The nucleotide which is approximately at the center of the target sequence is indicated in underlined to allow for easy identification of the complementary sequence of subsequent DNA oligonucleotides. The first or incoming oligonucleotide, designated "OligoC", is a 30-mer with the following sequence: 5'-AGGCTATTCGGCTA<u>C</u>GACTGGGCACAACAG-3' (SEQ ID NO: 3) which is complementary to OligoB. The second or annealing oligonucleotide, designated "OligoI", is a 25-mer with the following sequence: 5'-TTGTGCCCAGTC<u>G</u>TAGCCGAATAGC-3' (SEQ ID NO: 4) which is complementary to OligoA. In certain experiments, we use in place of OligoI as the annealing oligonucleotide the following 15-mer LNA oligonucleotide, designated "OligoN": 5'-GCCCAGTC<u>G</u>TAGCCG-3' (SEQ ID NO: 5).

To test the formation of Y-arms under our assay conditions, we use a different target duplex DNA composed of two linear 67-mer oligonucleotides with sequence complementary to each other. The sequence of the first target strand, designated "OligoT", is: 5'-ACAACTGTGTTCACTAGCAACCT-CAAACAGACACCATGGTGCACCTGACTC-CTGAGGAGAAGTCTGC-3' (SEQ ID NO: 6) and the sequence of the second target strand, designated "OligoU", is: 3'-TGTTGACACAAGTGATCGTTG-GAGTTTGTCTGTGGTACCACGTGGACT-GAGGACTCCTCTTCAGACG-5' (SEQ ID NO: 7). We use two oligonucleotides complementary to the end of the OligoT/OligoU linear target duplex in these Y-arm experiments. The first or incoming oligonucleotide, designated "OligoX", is a 30-mer with the following sequence: 5'-GCAGACT-TCTCCTCAGGAGTCAGGTGCACC-3' (SEQ ID NO: 8) which is complementary to the end of the OligoT strand of the target duplex. The second or annealing oligonucleotide, designated "Oligo5", is a 30-mer with the following sequence: 5'-GTTGCACCTGACTCCTGAGGAGAAGTCTGC-3' (SEQ ID NO: 9) which is complementary to OligoU.

Figure 2:
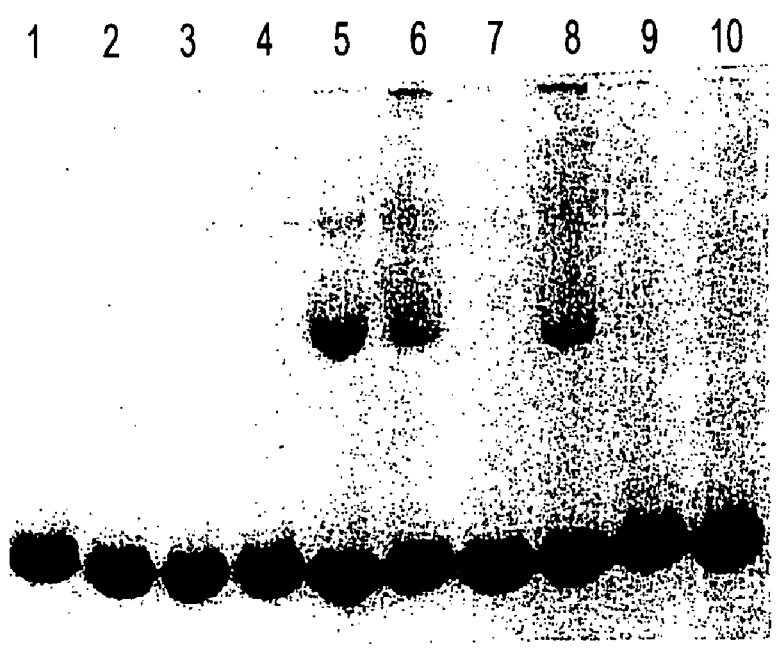
FIG. 2 is an autoradiogram showing double D-loop formation on a radiolabeled linear target under various conditions, according to embodiments of the present invention.

Annealing oligonucleotide and RecA are required for formation of double D-loops. We demonstrate that both the annealing oligonucleotide and a recombination protein are required by following the protocol as described in Example 1 but omitting certain reagents or steps. The results of these experiments are shown in FIG. 2 (using OligoA/OligoB target and OligoC/OligoI), FIG. 3 (using OligoA/Oligo B target and OligoC/OligoN) and FIG. 4 (using OligoT/OligoU target and OligoX/Oligo5).

In a control experiment shown in lane 1 of these Figures, omitting both oligonucleotides leads to no complex formation. Similarly, when we deproteinize the complex after the addition of the incoming oligonucleotide and omit the annealing oligonucleotide, we do not observe any stable complexes (lane 2). This confirms that single D-loops containing DNA oligonucleotides are unstable after deproteinization.

Finally, as shown in lanes 3 and 4 of these figures, when we deproteinize the complex while adding the annealing oligonucleotide, we observe no double D-loop formation. This was observed regardless of whether the annealing step was carried out at 37° C. (lane 3) or 4° C. (lane 4). These results indicate that the single D-loop must remain stabilized by the recombination protein for the annealing oligonucleotide to be incorporated into the structure.

To confirm this result, we perform a competition experiment where we add an excess of incoming oligonucleotide after the formation of the single D-loop and before the addition of the annealing oligonucleotide. As shown in lane 7 of FIGS. 2, 3 and 4, the addition of excess incoming oligonucleotide that has not been coated with RecA abolishes formation of double D-loops where the target sequence is in the middle of the linear duplex (FIGS. 2 and 3) and dramatically reduces the formation of Y-arms (FIG. 4). By sequestering the annealing oligonucleotide in a hybrid with the complementary incoming oligonucleotide, formation of a double D-loop is inhibited.

However, if the double D-loop or Y-arm structure is formed first by adding annealing oligonucleotide before the addition of excess free incoming oligonucleotide there is essentially no impairment of double D-loop formation. This result confirms that the annealing oligonucleotide is incorporated into the double D-loop prior to deproteinization of the complex.

Oligonucleotides comprising LNA form double D-loops more efficiently. The results shown in FIG. 2 (using OligoA/OligoB target and OligoC/OligoI), FIG. 3 (using OligoA/Oligo B target and OligoC/OligoN) and FIG. 4 (using OligoT/OligoU target and OligoX/Oligo5) lanes 5 and 6 demonstrate that using an oligonucleotide comprising LNA results in much greater double D-loop formation than when oligonucleotides containing only DNA residues are used. We observe this result both when we perform the deproteinization step, i.e. addition of SDS, at 4° C. as in the standard protocol described in Example 1 (lane 6) or when we perform deproteinization at 37° C. (lane 5). In addition, comparison of the results shown in FIG. 3, lanes 5 and 6 to the results shown in FIG. 2, lanes 5 and 6 also clearly shows that the use of an oligonucleotide comprising LNA results in much greater formation of double D-loops than when oligonucleotides containing only DNA residues are used.

Oligonucleotides comprising LNA can form double D-loops in a single-step reaction. If incoming and annealing oligonucleotides are added simultaneously to the target duplex, double D-loop formation is severely impaired or absent. We demonstrate this using DNA oligonucleotides (OligoC/OligoI with OligoA/OligoB target) as shown in FIG. 2, lane 9 and lane 10. For these experiments we follow the protocol outlined in Experiment 1, except that we coat both oligonucleotides with RecA and then simultaneously add them in equivocal amounts to the target nucleic acid. In FIG. 2, lane 9 the oligonucleotides are combined and coated with RecA together before adding them to the target nucleic acid and in FIG. 2, lane 10 the oligonucleotides are first separately coated with RecA and then added together to the target nucleic acid. As shown in FIG. 4, lane 9 and lane 10, simultaneous addition of two DNA oligonucleotides also fails to support the formation of Y-arms.

Figure 3:
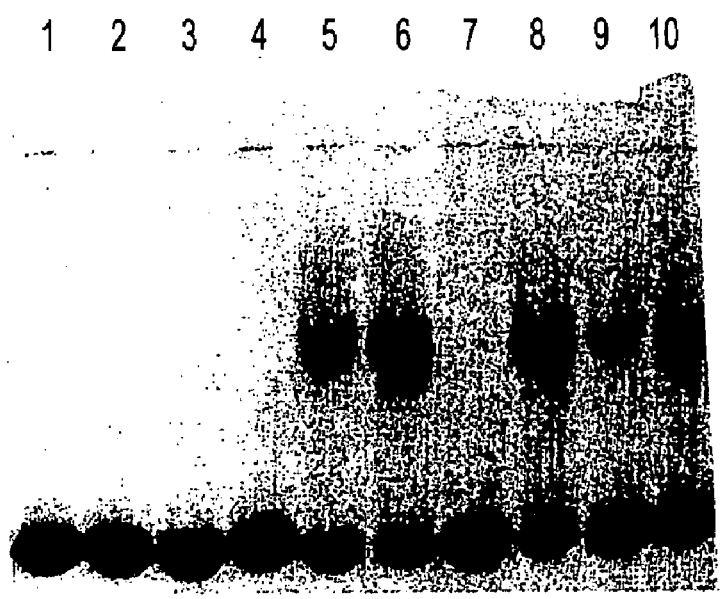
FIG. 3 is an autoradiogram showing double D-loop formation on a radiolabeled linear target under various conditions, according to embodiments of the present invention.
Figure 4:
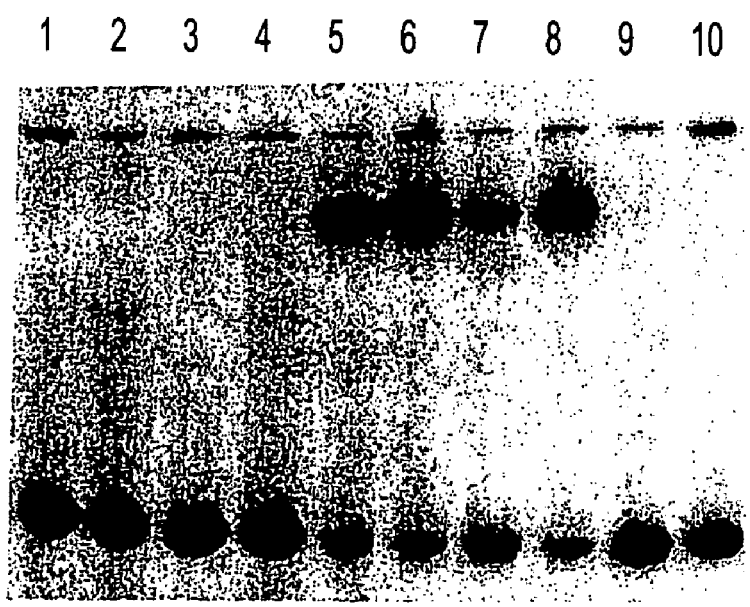
FIG. 4 is an autoradiogram showing double D-loop formation on a radiolabeled linear target under various conditions, according to embodiments of the present invention.

However, as shown in FIG. 3, lane 9 and lane 10, simultaneous addition of two oligonucleotides where one of the oligonucleotides is composed of LNA residues results in surprisingly significant formation of double D-loops. The extent of double D-loop formation is greater when the oligonucleotides were separately coated with RecA before addition to the target nucleic acid (lane 10) than when they are mixed together before coating with RecA (lane 9).

EXAMPLE 3

Figure 5:
FIG. 5 is an autoradiogram showing temperature effects on double D-loop formation, according to embodiments of the present invention.

Determination of Optimal Temperature and Annealing Times for Formation of Double D-Loops Determination of optimal annealing temperature. We test the formation of double D-loops using the OligoA/OligoB duplex as the target, OligoC as the incoming oligonucleotide and OligoI as the annealing oligonucleotide (target sequence and oligonucleotides as described in Example 2). We follow the protocol described in Example 1, except we vary the temperature at which the reaction is incubated after the addition of the annealing oligonucleotide. As shown in FIG. 5, we test incubation at 4° C., 15° C., 25° C., 37° C. and 45° C. We observe increased formation of the double D-loop as we increase the temperature up to approximately 37° C. In this experiment, the extent of double D-loop formation at 37° C. is approximately equal to the extent of double D-loop formation at 45° C.

Figure 6:
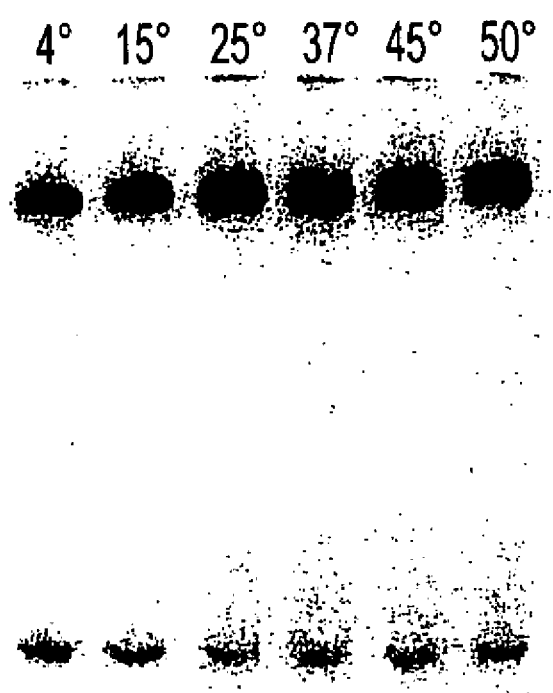
FIG. 6 shows Y-loop (Y-arm) formation over a range of temperatures, according to embodiments of the present invention.

We also determine the optimal temperature for the formation of Y-arms using the OligoT/OligoU duplex as the target, OligoX as the incoming oligonucleotide and Oligo5 as the annealing oligonucleotide. We vary the temperature as described above for the OligoA/OligoB experiment. As shown in FIG. 6, we test incubation at 4° C., 15° C., 25° C., 37° C., 45° C. and 50° C. We observe almost quantitative conversion of the free duplex target to oligonucleotide-containing Y-arms at all temperatures. However, as seen in the OligoA/OligoB experiment, increasing temperature clearly result in incremental increases in Y-arm formation, with optimal Y-arm formation at approximately 37° C.

It is readily apparent to one of skill in the art that this procedure can be applied to any target nucleic acid or set of oligonucleotides to determine the annealing temperature that leads to optimal formation of the corresponding double D-loop or Y-arm structure.

Figure 7:
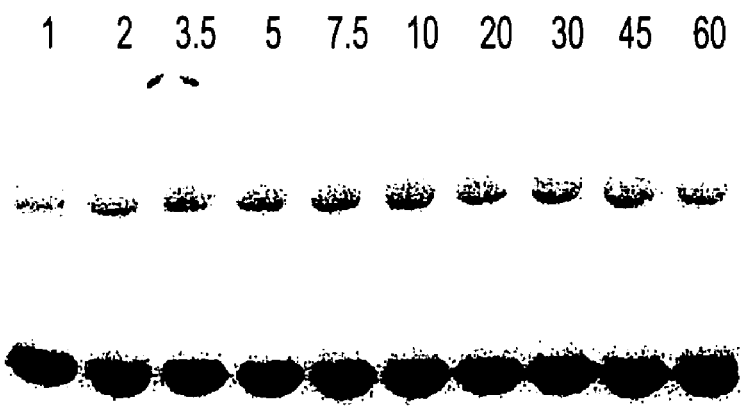
FIG. 7 shows double D-loop formation over a range of times, in minutes, according to embodiments of the present invention.

Determination of optimal annealing time. We test the formation of double D-loops using the OligoA/OligoB duplex as the target, OligoC as the incoming oligonucleotide and OligoI as the annealing oligonucleotide. We follow the protocol described in Example 1, except we vary the incubation time at 37° C. after the addition of the annealing oligonucleotide. As shown in FIG. 7, we test incubation for 1, 2, 3.5, 5, 7.5, 10, 20, 30, 45 and 60 minutes. We observe that double D-loop formation occurs very rapidly and that the extent of double D-loop formation increases up to an incubation time of approximately 10 minutes. After 10 minutes, we observe that the proportion of target nucleic acid in double D-loops begins to decrease, probably due to instability of the double D-loop, which contained only DNA oligonucleotides.

Figure 8:
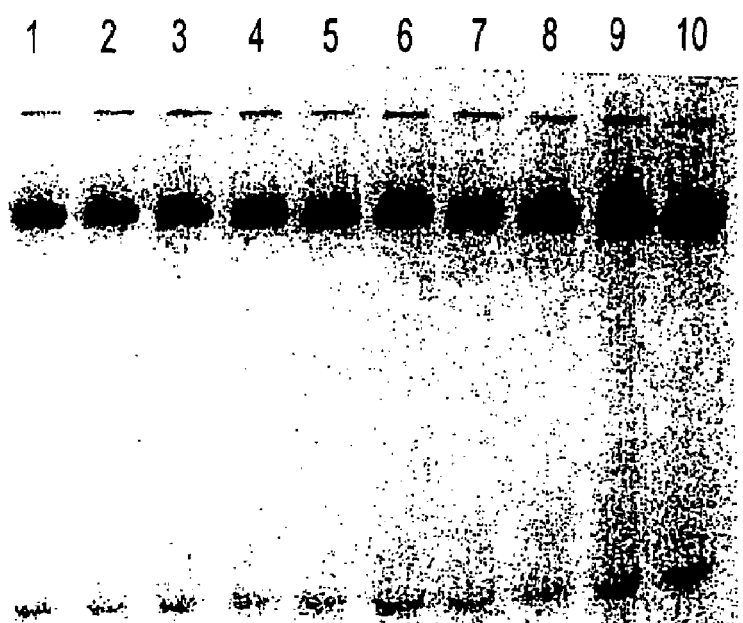
FIG. 8 shows Y-arm formation over a range of times, in minutes, according to embodiments of the present invention.

We determine the optimal annealing time for the formation of Y-arms using the OligoT/OligoU duplex as the target, OligoX as the incoming oligonucleotide and Oligo5 as the annealing oligonucleotide. We vary the annealing time as described above for the OligoA/OligoB experiment. As shown in FIG. 8, we test incubation at 37° C. for 1, 2, 3, 4, 5, 6, 8, 10, 15 and 20 minutes. We observe almost quantitative conversion of the free duplex target to oligonucleotide-containing Y-arms at the one-minute time point and we do not observe a substantial increase in Y-arm formation with longer incubation times. In contrast to the OligoA/OligoB experiment, however, we do not see a reduction in the ratio of free duplex target to target complexed with oligonucleotides in the Y-arms, which is probably due to the fact that double D-loops formed at the end of a linear duplex target (i.e. Y-arms) are generally more stable that double D-loops formed in the middle of a linear duplex target.

It is readily apparent to one of skill in the art that this procedure can be applied to any target nucleic acid or set of oligonucleotides to determine the annealing time that leads to optimal formation of the corresponding double D-loop.

EXAMPLE 4

Determination of Optimal Oligonucleotide Lengths for Formation of Double D-Loops or Y-Arms Oligonucleotides used in this example. We use the OligoT/OligoU duplex as the target nucleic acid for these experiments. We use incoming DNA oligonucleotides complementary over a range of lengths to the end of the duplex target as follows: OligoV is a 20-mer with the sequence 5'-GCAGACTTCTCCTCAGGAGT-3' (SEQ ID NO: 10); OligoW is a 25-mer with the sequence 5'-GCAGACTTCTCCTCAGGAGTCAGGT-3' (SEQ ID NO: 11); OligoX is a 30-mer (SEQ ID NO: 8); OligoY is a 35-mer with the sequence 5'-GCAGACTTCTCCTCAGGAGTCAGGTGCACCATGGT-3' (SEQ ID NO: 12); OligoZ is a 40-mer with the sequence 5'-GCAGACTTCTCCTCAGGAGTCAGGTGCACCATGGTGTCTG-3' (SEQ ID NO: 13); and Oligo1 is a 46-mer with the sequence 5'-GCAGACTTCTCCTCAGGAGTCAGGTGCACCATGGTGTCTGTTTGAG-3' (SEQ ID NO: 14). We use annealing DNA oligonucleotides complementary to the end of the duplex target (and to the incoming oligonucleotides) over a range of lengths as follows: Oligo2 is a 20-mer with the sequence 5'-ACTCCTGAGGAGAAGTCTGC-3' (SEQ ID NO: 15); Oligo4 is a 25-mer with the sequence 5'-ACCTGACTCCTGAG-GAGAAGTCTGC-3' (SEQ ID NO: 16); Oligo5 is a 30-mer with the sequence 5'-GTTGCACCTGACTCCTGAG-GAGAAGTCTGC-3' (SEQ ID NO: 9); Oligo6 is a 35-mer with the sequence 5'-ACCATGGTGCACCTGACTCCT-GAGGAGAAGTCTGC-3' (SEQ ID NO: 17); Oligo7 is a 40-mer with the sequence 5'-CAGACACCATGGTGCAC-CTGACTCCTGAGGAGAAGTCTGC-3' (SEQ ID NO: 18); and Oligo8 is a 46-mer with the sequence 5'-ACCTGACTC-CTGAGGAGAAGTCTGCCGTTACTGCCCT-GTGGGGCAA-3' (SEQ ID NO: 19).

Figure 9:
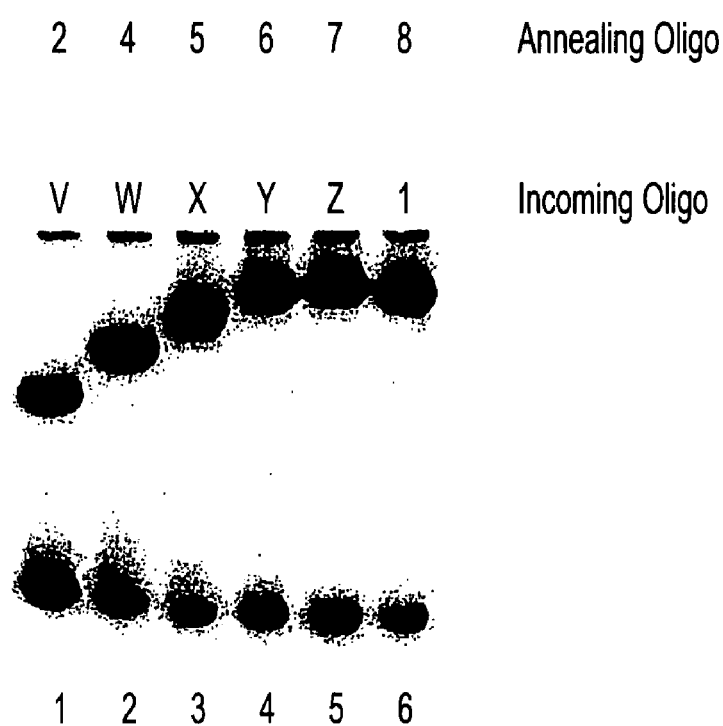
FIG. 9 shows Y-arm formation with varying incoming and annealing oligonucleotides, according to embodiments of the present invention.
Figure 10:
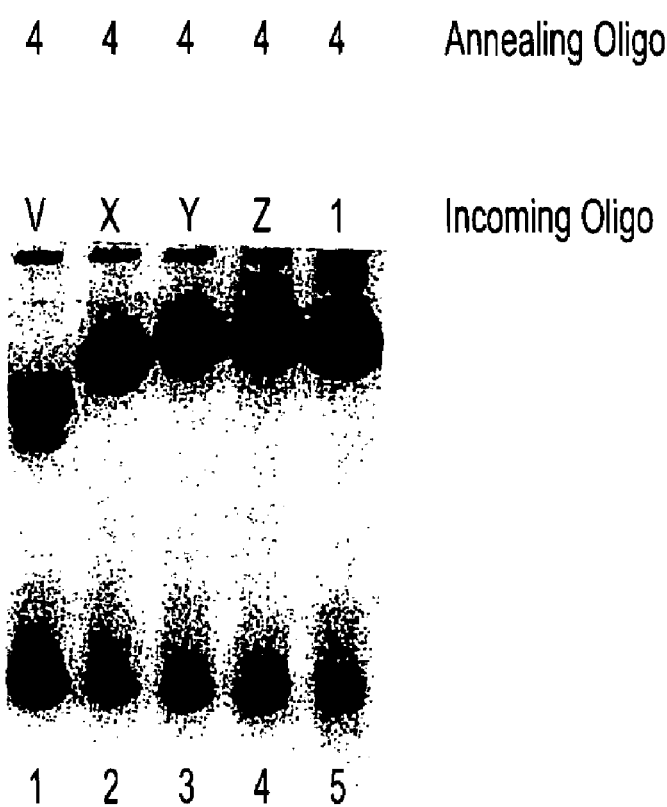
FIG. 10 shows Y-arm formation with varying incoming and annealing oligonucleotides, as indicated, according to embodiments of the present invention.

Oligonucleotides of different lengths form double D-loops and Y-arms. We use the oligonucleotides described above to form Y-arms according to the protocol detailed in Example 1. As shown in FIG. 9, lanes 1-6, all of these oligonucleotides, ranging in size from 20 nucleotides to 46 nucleotides, efficiently form a Y-arm when the oligonucleotides are of equal length. This experiment does show, however, that longer oligonucleotides appear to form a Y-arm more efficiently. We show in FIG. 10, lanes 1-5, that the oligonucleotides used for the formation of a Y-arm do not need to be of the same length and that the annealing oligonucleotide can be either longer (lane 1) or shorter (lanes 2-5) than the incoming oligonucleotide.

It is readily apparent to one of skill in the art that this procedure can be applied to any target nucleic acid or set of oligonucleotides to determine the length of the oligonucleotides that lead to optimal formation of the corresponding double D-loop.

EXAMPLE 5

Determination of Optimal Oligonucleotide Composition for Formation of Double D-Loops Oligonucleotides used in this example. We use the OligoA/OligoB duplex as the target nucleic acid for these experiments. As the incoming oligonucleotide, we use either OligoC (SEQ ID NO: 3) or the complementary oligonucleotide which targets the opposite strand of the duplex target, designated "OligoD", which has the sequence 5'-CTGTTGTGC-CCAGTCCTAGCCGAATAGCCT-3' (SEQ ID NO: 20). We then use the following annealing oligonucleotides: OligoE is a DNA 30-mer with the sequence 5'-AGGCTATTCGGCTACGACTGGGCACAACAG-3' (SEQ ID NO: 21); OligoF is a DNA 25-mer with the sequence 5'-GCTATTCGGCTACGACTGGGCACAA-3' (SEQ ID NO: 22); OligoG is a DNA 20-mer with the sequence 5'-ATTCGGCTACGACTGGGCAC-3' (SEQ ID NO: 23); OligoH is a DNA 30-mer with the sequence 5'-CTGTTGTGCCCAGTCCTAGCCGAATAGCCT-3' (SEQ ID NO: 24); OligoI is a DNA 25-mer with the sequence 5'-TTGTGCCCAGTCGTAGCCGAATAGC-3' (SEQ ID NO: 4); OligoJ is a 2'-O-methyl-RNA (2'-OMe-RNA) 25-mer with the sequence 5'-GCUAUUCGGCUACGACUGGGCACAA-3' (SEQ ID NO: 25); OligoK is a 2'-OMe-RNA 30-mer with the sequence 5'-CUGUUGUGCCCAGUCCUAGCCGAAUAGCCU-3' (SEQ ID NO: 26); OligoL is a 2'-O-methyl-RNA 25-mer with the sequence 5'-UUGUGCCCAGUCGUAGCCGAAUAGC-3' (SEQ ID NO: 27); OligoM is a DNA 25-mer with phosphorothioate backbone linkages with the sequence 5'-TTGTGCCCAGTCGTAGCCGAATAGC-3' (SEQ ID NO: 28); OligoN is an LNA 15-mer (SEQ ID NO: 5); OligoO is a LNA-DNA-LNA 15-mer with the sequence 5'-GCCCagtcgtaGCCG-3', where the LNA residues are indicated with capital letters and the DNA residues are in lowercase (SEQ ID NO: 29); OligoP is an LNA-DNA-LNA 25-mer with the sequence 5'-TTGtgcccagtcgtagccgaatAGC-3', where the LNA residues are indicated with capital letters and the DNA residues are in lowercase (SEQ ID NO: 30); OligoQ is a PNA 18-mer with the sequence lys-ACGGGTCAG G̲ATCGGCTT-gly (SEQ ID NO: 31); OligoR is a PNA 18-mer with the sequence lys-ACGGGTCAGCATCGGCTT-gly (SEQ ID NO: 32); OligoS is a PNA 20-mer with the sequence Ac-E-GTGCCCAGTCC̲TAGCCGAAT-E-NH$_2$ (SEQ ID NO: 33). All of the oligonucleotides (or PNAs) are completely complementary to the target sequence except OligoH, OligoK, OligoQ and OligoS which each have a single basepair mismatch.

Figure 11:
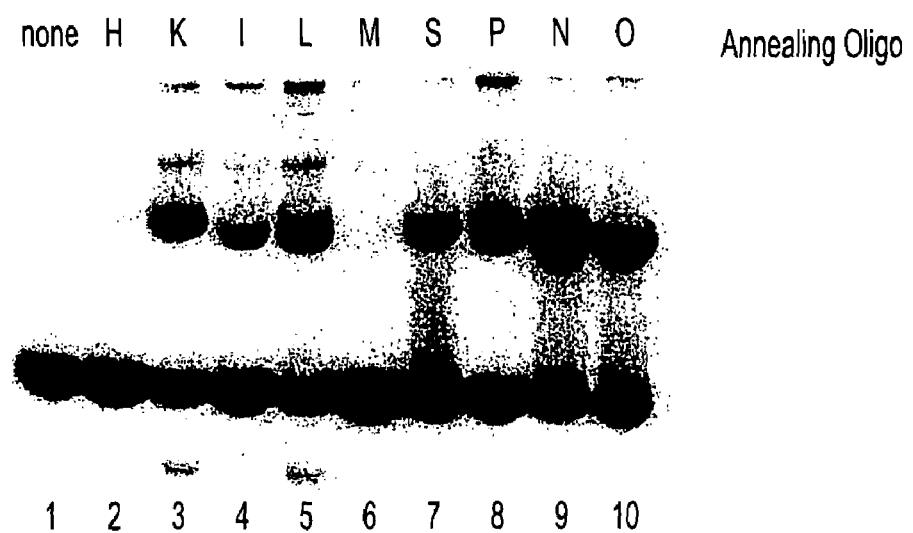
FIG. 11 shows double D-loop formation with annealing oligonucleotides as indicated, according to embodiments of the present invention.

We show in FIG. 11 the formation of double D-loops using OligoA/OligoB as the target nucleic acid, OligoC as the incoming oligonucleotide and the oligonucleotides as the annealing oligonucleotide as indicated in the Figure. From these data it is apparent that oligonucleotides with a mismatched base can form a double D-loop (lanes 2 and 3) and that when we use 2'-OMe-RNA oligonucleotides (lanes 3 and 5), PNA (lane 7) and LNA oligonucleotides (lanes 8-10) as annealing oligonucleotides the formation of double D-loops is more robust that with DNA oligonucleotides. We also find that annealing oligo-nucleotides containing phosphorothioate modifications do not function as well as DNA for the formation of double D-loops (lane 6). Finally, this experiment confirms that oligonucleotides that are partially modified still enhance double D-loop formation relative to a DNA oligonucleotide (lanes 8 and 10).

Figure 12:
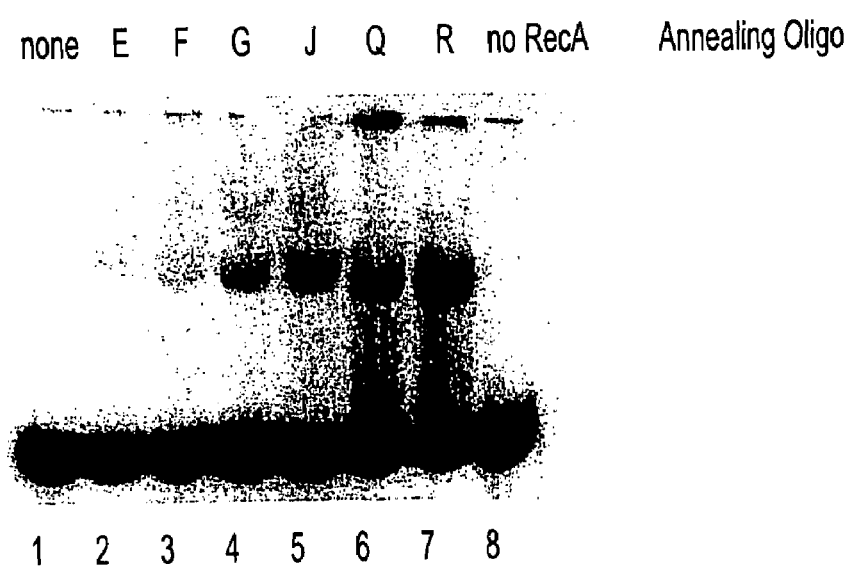
FIG. 12 shows double D-loop formation using annealing oligonucleotides as indicated, according to embodiments of the present invention.

We confirm these results using the OligoA/OligoB target nucleic acid, OligoD as the incoming oligonucleotide, which recognizes the opposite strand of the OligoA/OligoB target nucleic acid relative to the previous experiment, and annealing oligonucleotides as indicated in FIG. 12. These data confirm that an oligonucleotide with a mismatched base can form a double D-loop (lane 6) and that when we use 2'-OMe-RNA oligonucleotides (lane 5) and PNA (lanes 6 and 7) as annealing oligonucleotides the formation of double D-loops is more robust that with DNA oligonucleotides. Combined with the previous experiment, these data also show that the double D-loop can be formed when the incoming oligonucleotide recognizes either strand of the target duplex.

It is readily apparent to one of skill in the art that this procedure can be applied to any target nucleic acid or set of oligonucleotides to determine the composition of the oligonucleotides that lead to optimal formation of the corresponding double D-loop and that a wide range of oligonucleotides functions in the methods of the invention.

EXAMPLE 6

Oligonucleotide:Target Capture and DNA Detection

Oligonucleotides used in this example. We use the OligoA/OligoB duplex as the target nucleic acid for these experiments. We use a $^{32}$P-labeled DNA oligonucleotide as the incoming oligonucleotide. We then use a biotin-labeled annealing oligonucleotide comprising at least one modified backbone that enhances hybrid stability or a modified base that enhances hybrid stability.

The capture/detection assay. We assay the presence of two oligonucleotides (one biotin-labeled and the other $^{32}$P-labeled) on the OligoA/OligoB duplex target molecule by capturing biotin-containing-oligonucleotide:target double D-loops on streptavidin-coated paramagnetic beads. The beads are washed in 1×RecA reaction buffer (1.0 mM ATP-γ-S; 25 mM Tris-acetate, pH 6.8; 1 mM dithiothreitol; and 1 mM magnesium acetate), 10×RecA reaction buffer, and finally in 1×RecA reaction buffer. Before DNA capture, equal aliquots of washed beads are added to individual 1.5 ml microcentrifuge tubes and the final wash buffer is removed.

Liquid is removed from all bead suspensions by placing microcentrifuge tubes containing the bead mixtures in a magnetic separating rack.

The double D-loop containing samples from above are each added to a microcentrifuge tube containing an aliquot of the washed paramagnetic beads. The samples are mixed, and incubated at room temperature for 15 min. The mixtures are shaken several times during incubation to ensure efficient biotin:streptavidin interaction. After the capture reaction, i.e., the binding of streptavidin to biotin, the paramagnetic beads in each reaction are amassed with a magnet and the reaction buffer removed.

Each sample of beads is washed three times is with 1×RecA reaction buffer. The presence of $^{32}$P-labeled probe strand is assessed by scintillation counting of the DNA captured by each bead reaction.

The results indicate that the hybridization product, containing two complementary but differentially labeled oligonucleotides, can be captured using the streptavidin interaction with the biotin labeled probe strand and subsequently detected by a label in the complementary probe strand.

EXAMPLE 7

RecA+ Facilitated DNA Amplification Without Target DNA Denaturation

Reaction conditions for RecA protein facilitated DNA amplification have been described in U.S. Pat. No. 5,223,414, incorporated herein by reference in its entirety.

We use a double-stranded duplex DNA target derived from plasmid DNA and two sets of oligonucleotides that form double D-loops at discrete sites separated by at least 200 nucleotides for ease of detection. We ensure that elongation of DNA primers occurs in only the desired direction, by terminating the 3'-ends of the appropriate primers with 2',3'-dideoxynucleotide, which lacks the 3'-hydroxyl group present in the conventional dNTPs and essential for elongation therefrom. We add the dideoxynucleotide to the primer using the enzyme terminal deoxynucleotide transferase.

We form double D-loops in the target nucleic acid using the two sets of oligonucleotides described above and the method described in Example 1. We then use the resulting two sets of double D-loops as the substrate in a typical DNA amplification reaction. The DNA reaction can be carried out in buffer containing 10 mM Tris-HCl (pH 7.5), 8-12 mM MgCl$_2$, and 50 mM NaCl supplemented with 200-750 μM dNTPs and DNA polymerase (e.g., exonuclease-free, DNA polymerase I, Klenow, or T7 DNA polymerase). The reaction may additionally be supplemented with other enzymes or proteins (e.g. DNA helicase, DNA ligase and SSB protein) which may facilitate the formation of the specific amplification product. The reaction is allowed to proceed for as long as necessary at 37° C. Upon termination, samples are optionally deproteinized and analyzed by gel electrophoresis. After electrophoretic separation, the resulting amplified DNA can be visualized by either ethidium bromide staining of the DNA in the gel or by DNA hybridization with a target specific DNA probe. Alternatively, one of the DNA oligonucleotides can be biotinylated and the newly synthesized DNA captured by appropriate means and then detected as previously described.

DNA synthesis reactions are initiated by the addition of 1-2 unit(s) of exonuclease-free E. coli DNA polymerase I (U.S. Biochemicals) and 750 μM of each DNTP. The reactions are incubated at 37° C.

Following the initial addition of polymerase, the reactions can be supplemented with 1 unit of e.g., Klenow and/or additional dNTPs, at specific intervals spaced over the time course of the reaction.

Samples are treated with proteinase K, before being loaded for electrophoretic separation. After electrophoretic separation the resulting amplified DNA fragments can be visualized by either ethidium bromide staining of the gel or by hybridization with a target specific probe.

For hybridization analysis the gel can be transferred by standard protocols onto hybridization transfer membrane. We then detect the DNA using end-labeled probe corresponding to the DNA sequence of the target nucleic acid internal to the two double D-loops. We then detect hybridization signal by autoradiography or using a phosphorimager.

EXAMPLE 8

In Situ DNA Detection Utilizing the Double D-Loop Reactions

Preparation of oligonucleotide complex. We design oligonucleotides to form a double D-loop in a target nucleic acid. One of these oligonucleotides comprises LNA and one of these oligonucleotides comprises a detectable fluorophore.

Preparation and transformation of HeLa cells. We grow HeLa cells at 37° C. and 5% $CO_2$ in a humidified incubator to a density of $2 \times 10^5$ cells/ml in an 8 chamber slide (Lab-Tek). We replace the DMEM with Optimem and transfect the cells with 5 µg of RecA-coated oligonucleotides that are previously complexed to 10 µg lipofectamine according to manufacturer's directions (Life Technologies). We treat the cells with the liposome, oligonucleotide mix for 6 hours at 37° C. We wash the treated cells with PBS and add fresh DMEM. After a 16-18 hour recovery period we assay the cells for fluorescence indicative of formation of the double D-loop. Specific signals are detected using standard fluorescence microscopy observation techniques.

EXAMPLE 9

RecA Mediated Double D-Loop Hybridization Reactions Using a Variety of Cofactors Oligonucleotides used in this example. We use the $^{32}$P-labeled OligoA/OligoB duplex as the target nucleic acid for these experiments. We use the DNA oligonucleotide OligoC as the incoming oligonucleotide and OligoN as the annealing oligonucleotide.

Double-D-loops can be formed using different cofactors for the RecA protein. We use the above-mentioned oligonucleotides to form double D-loops according to Example 1 except we substitute rATP, DATP or GTP-γ-S for ATP-γ-S in the RecA coating reaction. These reactions are performed with or without a regenerating system. The double D-loops are then deproteinized and detected as described previously.

EXAMPLE 10

Double D-Loop Formation Occurs Under a Range of Conditions

We test the ability of the double D-loop formation reaction to tolerate variations in reagent concentrations. We form double D-loops by combining 1.1 µl of fluorescently labeled incoming oligonucleotide LDF/45G (5'-Cy™ 5-GGTG-GAGAGGCTATTCGGCTAGGACTGGGCA-CAACAGACAATCGG-3'; SEQ ID NO: 34), 3 µl of 5× Synaptic Buffer (125 mM Tris-acetate, 5 mM Mg(acetate)$_2$ and 5 mM DTT), 1.5 µl 10 mM ATP-γ-S, water and 73.5 µM RecA. We vary the concentration of incoming oligonucleotide in the 1.1 µl sample using 2.25 µM, 4.5 µM, 9 µM or 18 µM. We vary the concentration of RecA relative to the concentration of the incoming oligonucleotide in the mixture, e.g. we add 0.5 µl RecA (73.5 µM) to the mixture when the concentration of the incoming oligonucleotide is 2.25 µM, 1.0 µl RecA when the concentration is 4.5 µM, and so on. Prior to the addition of RecA, water is added to the reaction mixture so that the final volume after the addition of RecA is 14 µl. We incubate this reaction for 10 minutes at 37° C. to allow for binding of RecA protein to the oligonucleotide ("presynapsis", see FIG. 1 for an outline of the method).

We prepare a double-stranded target by PCR from a neomycin phosphotransferase gene with a point mutation (Kan⁻) using two oligonucleotide primers: 3910U (5'-CAGGGGAT-CAAGATCTGAT-3'; SEQ ID NO: 35) and 3CGT$^{th}$ (5'-GCT-TCAGTGACAACGTCGAG-3'; SEQ ID NO: 36). The sequence of the resulting PCR product is shown in FIG. 13 (SEQ ID NO: 37). We add 3.5 µl of the PCR product at a concentration of 0.7 µM and 2.5 µl 74 mM Mg(acetate)$_2$. We incubate this reaction for 10 minutes at 37° C. to allow synapsis between the incoming oligonucleotide and the target nucleic acid molecule. We then add 0.74 µl of 27 µM annealing oligonucleotide KLO2 which comprises LNA modified residues (5'-GCCCAGTCGTAGCCG-3'; SEQ ID NO: 38). We incubate this reaction for 5 minutes at 37° C. to allow the annealing oligonucleotide to anneal to the target nucleic acid. We then stop the reaction by placing briefly on dry ice. We denature the RecA bound to the oligonucleotide:target complex by placing the reaction at about 4° C. in an ice bath and adding 2 µl of 10% SDS and 2 µl of 10× loading dye (15-25% Ficoll, optionally supplemented with 0.05% bromophenol blue).

We analyze the samples prepared as described above by separating on a 2.5% agarose gel at 4° C. The gel does not contain ethidium bromide. We strain the gels after running then with 1× SYBR® green, a dye which binds double-stranded DNA, and scan on a Typhoon™ imager. We monitor the gel positions of the double D-loop and the double-stranded target DNA by detecting the SYBR® green dye. We monitor the formation of double D-loops under these assay conditions by detecting the retarded migration of the fluorescently labeled incoming oligonucleotide.

We observe that double D-loops are formed at all incoming oligonucleotide concentrations. The fraction of target molecules that are in double D-loops at the different incoming oligonucleotide concentrations is 33% with 2.25 µM oligonucleotide; 37% with 4.5 µM oligonucleotide; 39% with 9 µM oligonucleotide; and 42% with 18 µM oligonucleotide. This indicates that the efficiency of double D-loop formation varies depending on the incoming oligonucleotide concentration. These results also indicate that double D-loop formation occurs over a wide range of oligonucleotide concentrations. Based on these results, unless indicated otherwise, the reaction in the following examples uses 1.11 µl of 18 µM incoming oligonucleotide and 2.0 µl of RecA.

EXAMPLE 11

Effect of Varying Annealing Oligonucleotide Composition and Target Sequence on Double D-Loop Formation We test the effect of varying the length, composition and sequence of the annealing oligonucleotide and the sequence of the target nucleic acid molecule on double D-loop formation.

We form double D-loops using the Kan⁻ double-stranded PCR product as the target nucleic acid molecule following the protocol described in Example 10 except that we incubate the reaction after adding the annealing oligonucleotide for 10 minutes at 37° C. We analyze the samples prepared by separating on a 2.5% agarose gel at 4° C. as described above.

Figure 14:
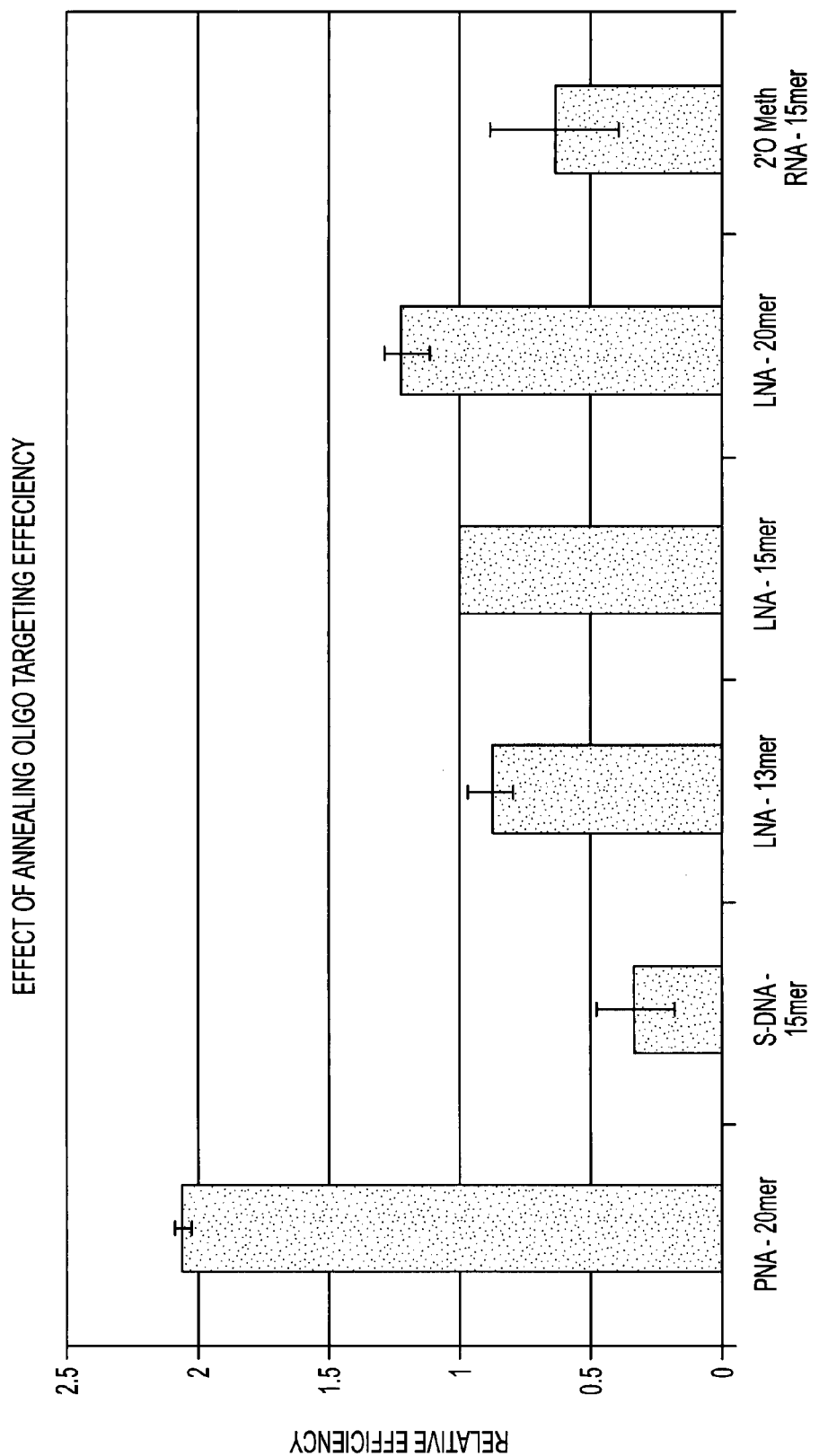
FIG. 14 shows the efficiency of double D-loop formation using the Kan⁻ PCR product as the target, with efficiency normalized to double D-loop formation efficiency with KLO2 (indicated in the figure as LNA-15mer), according to embodiments of the present invention.

We test annealing oligonucleotides comprising PNA; DNA with a phosphorothioate backbone; 2'-O-methyl RNA; and LNA as indicated in Table 1. As indicated in Table 1, we test annealing oligonucleotides of various lengths. We normalize the percentage of double D-loop formation relative to the percentage of double D-loop formation using KLO2 as the annealing oligonucleotide to calculate relative efficiency. As indicated in FIG. 14, we observe that stable double D-loop formation occurs using any of the test annealing oligonucleotides. In this reaction, we observe that double D-loop formation is most efficient when oligonucleotides comprising PNA are used in the reaction. As indicated by the error bars in FIG. 14, the variation in the efficiency of double D-loop formation is very low, indicating that double D-loop formation can be used in quantitative as well as qualitative applications.

We also form double D-loops using a PCR product produced from a plasmid containing the a functional hygromycin resistance gene (Hyg⁺) or a hygromycin resistance gene containing a point mutation (Hyg⁻; FIG. 15; SEQ ID NO: 115) using primers AUR123f (5'-TCTGCACAATATTTCAAGC-3'; SEQ ID NO: 45) and Hyg1560r (5'-AAATCAGCCATG-TAGTG-3'; SEQ ID NO: 46). We follow the protocol described in this Example for the formation of double D-loops in the Kan⁻ PCR product using HygUDF/45G as the incoming oligonucleotide (5'-Cy™5-CGCAGCTATTTAC-CCGCAGGACCTATCCACGCCCTCCTACATCGA-3'; SEQ ID NO: 47) and various annealing oligonucleotides as indicated in Table 2. We analyze the samples prepared by separating on a 2.5% agarose gel at 4° C. as described above.

Figure 16:
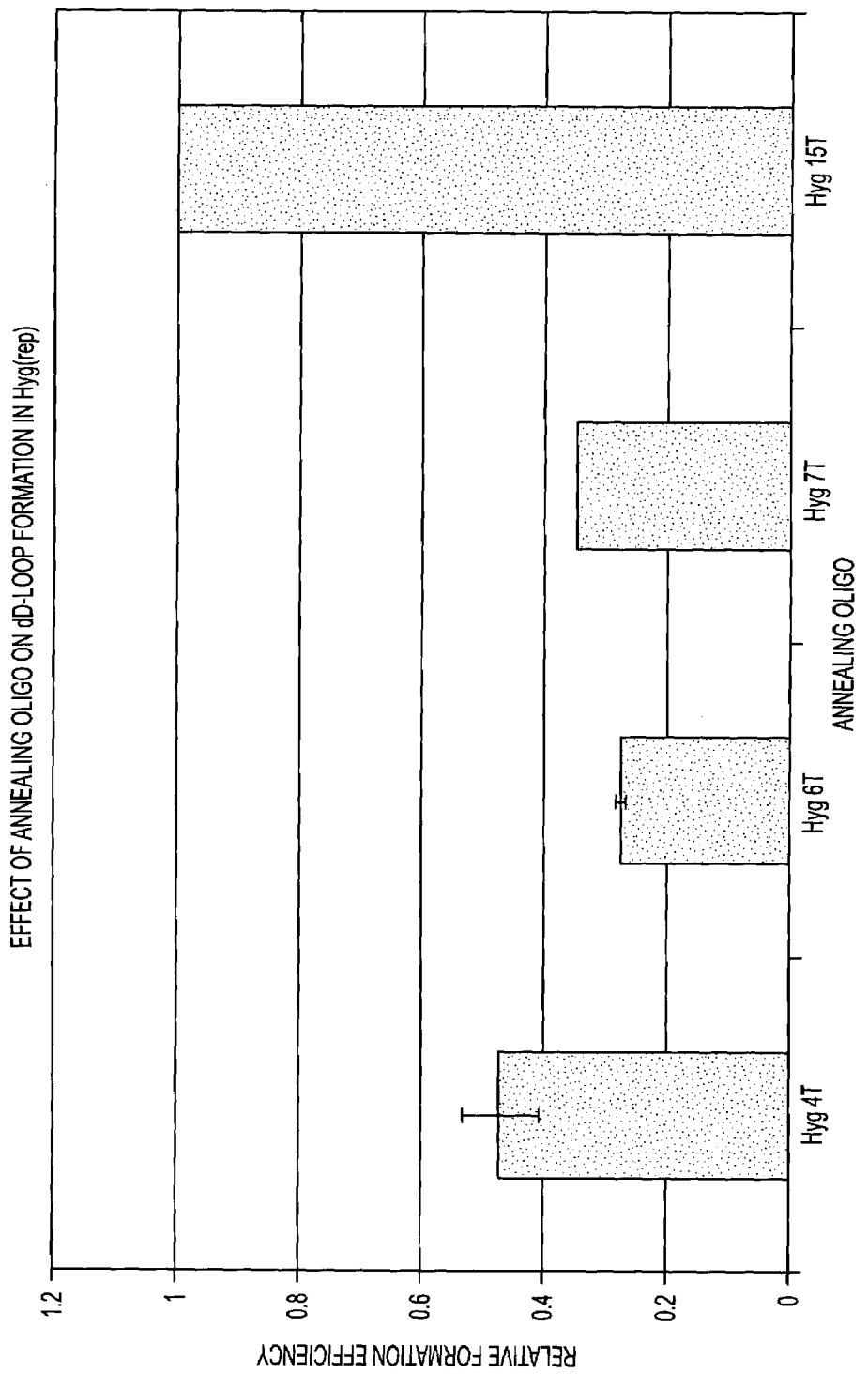
FIG. 16 shows the efficiency of double D-loop formation according to embodiments of the present invention, using the Hyg⁻ PCR product as the target, with efficiency normalized to double D-loop formation efficiency with Hyg15T.

We test annealing oligonucleotides comprising LNA as indicated in Table 2. As indicated in Table 2, we also test annealing oligonucleotides of various lengths. We normalize the percentage of double D-loop formation relative to the percentage of double D-loop formation using Hyg15T as the annealing oligonucleotide to calculate relative efficiency. As indicated in FIG. 16, we observe that stable double D-loop formation occurs using any of the test annealing oligonucleotides. In this reaction, we observe that double D-loop formation is most efficient when we use the longest of the test oligonucleotides. As indicated by the error bars in FIG. 16, the variation in the efficiency of double D-loop formation in this reaction is also very low.

TABLE 2

Annealing Oligonucleotides for Hyg⁻ Target

| Name | Composition* | Sequence | SEQ ID NO: |
|---|---|---|---|
| Hyg4 | LNA | 5'-GGATAGGTCC-3' | 48 |
| Hyg6 | LNA | 5'-TGGATAGGTCCT-3' | 49 |
| Hyg7 | LNA | 5'-GTGGATAGGTCCTGC-3' | 50 |
| Hyg15 | LNA | 5'-GTGGATAGGTCCTGC-3' | 51 |

*The underlined residues in these oligonucleotides are DNA, the remainder are LNA.

EXAMPLE 12

Double D-Loop Formation is Sequence-Specific

We test the effect of heterologous nucleic acid molecules on the efficiency of double D-loop formation. We form double D-loops using the Kan⁻ double-stranded DNA target as described in Example 10 except that we add heterologous competitor nucleic acid molecules along with the Kan⁻ target and Mg(acetate)$_2$. We perform the competition experiments using two competing nucleic acid molecules which do not have significant sequence homology with the Kan⁻ target or either the incoming or annealing oligonucleotides: the Hyg⁻ PCR product described above (FIG. 15; SEQ ID NO:_____) and poly dI-dC (Sigma).

We first add the Hyg⁻ PCR fragment to the mixture in a 1:1, 5:1 and 10:1 molar ratio relative to the amount of the Kan⁻ target nucleic acid molecule. We observe that the addition of the non-specific Hyg⁻ PCR fragment has no noticeable effect on the efficiency of double D-loop formation. We then add the poly dI-dC non-specific competitor nucleic acid molecule in vast excess ($10^1$-, $10^2$-, $10^3$-, $10^4$- and $10^5$-fold excess over the amount of the Kan⁻ target nucleic acid molecule) Even with such a vast excess of competitor, we observe no noticeable effect on the efficiency of double D-loop formation. In the presence of $10^5$-fold excess of the poly dI-dC non-specific

TABLE 1

Annealing Oligonucleotides for Kan⁻ Target

| Name | Composition* | Sequence | SEQ ID NO: |
|---|---|---|---|
| KM2 | PNA | Ac-E-GTGCCCAGTCCTAGCCGAAT-E-NH$_2$ | 39 |
| UDS15G | DNA with phosphorothioate backbone | 5'-GCCCAGTCGTAGCCG-3' | 40 |
| UR15G | 2'-O—Me RNA | 5'-GCCCAGUCGUAGCCG-3' | 41 |
| KLO2 | LNA | 5'-GCCCAGTCGTAGCCG-3' | 42 |
| KLO6 | LNA | 5'-CCCAGTCGTAGCC-3' | 43 |
| KLO15 | LNA | 5'-GTGCCCAGTCGTAGCCGAAT-3' | 44 |

*The underlined residues in KLO15 are DNA, the remainder are LNA.

competitor, we observed approximately 50% efficiency of double D-loop formation and the concentration of the Kan⁻ target nucleic acid molecule was limiting for double D-loop formation. These results indicate that double D-loop formation is sequence specific and that a nucleic acid molecule that represents a very small fraction of the nucleic acid molecules in a reaction serves as the target for double D-loop formation.

EXAMPLE 13

Double D-Loop Formation in a Linearized Plasmid Target

We test the efficiency of formation of double D-loops in a large plasmid target. We form double D-loops as described in Example 10 except that we add 2.5 µl (0.5 µg) of a linearized 8.2 kb plasmid comprising the Kan⁻ target gene and 7.35 µl of water. We add additional water to the reaction because of the higher target concentration. We then monitor the formation of double D-loops in the target plasmid using different annealing oligonucleotides (KM2, KLO2, KLO6, and KLO15; Table 1). We analyze the samples prepared by separating on a 1% agarose gel at 4° C. as described above and detect formation of the double D-loop by monitoring colocalization of the SYBR® green and the Cy™5 marker on the incoming oligonucleotide. We can not accurately assess the efficiency of double D-loop formation in these reactions because the formation of the double D-loop does not produce a large enough mobility shift in the target.

We observe efficient double D-loop formation in the plasmid target with any of the four annealing oligonucleotides. In contrast to our observations with a smaller Kan⁻ nucleic acid target molecule (Example 11; FIG. 14), we observe that the a shorter, 15mer oligonucleotide (KLO2; SEQ ID NO: 38) forms double D-loops at a slightly greater efficiency than a 20mer oligonucleotide (KLO15; SEQ ID NO: 43). In addition, we observe little or no difference in the apparent efficiency of double D-loop formation when we use an annealing oligonucleotide comprising PNA or LNA. These results indicate that the size of the target does not significantly affect the efficiency of double D-loop formation.

EXAMPLE 14

Topoisomerase I Enhances Double D-Loop Formation in a Supercoiled Plasmid Target We test the effect of adding topoisomerase I on the formation of double D-loops in a large, supercoiled plasmid target. We form double D-loops as described in Example 13 except that the plasmid comprising the Kan⁻ target gene is supercoiled and we add various amounts of topoisomerase I (0.5, 1.0 and 1.5 units. (One unit of topoisomerase I relaxes completely 0.5 µg of plasmid in 30 minutes at 37° C.) to the reaction along with the target and we increase the incubation during that step to 30 minutes at 37° C. We then monitor the formation of double D-loops in the target plasmid using different annealing oligonucleotides (KM2 and KLO2; Table 1). We analyze the samples by separating on a 1% agarose gel at 4° C. as described above and detect formation of the double D-loop by monitoring colocalization of the bound SYBR® green marker and the Cy™5 marker on the incoming oligonucleotide.

We observe efficient double D-loop formation in the supercoiled plasmid target with either annealing oligonucleotide in both the presence and absence of topoisomerase I. We observe that increasing the amount of topoisomerase I increases the amount of double D-loop formation. Both LNA and PNA support comparable levels of double D-loop formation in supercoiled target nucleic acid. The reactions in which the double D-loops are formed with PNA have less background than reactions using LNA. These results indicate that double D-loops can be formed in a supercoiled target following the teachings of the instant invention. Further, topoisomerase I enhances, but is not essential for, double D-loop formation in a supercoiled target.

EXAMPLE 15

Purification of Nucleic Acid Molecules Using Double D-Loops

We test whether the sequence specificity of double D-loop formation can be used for purification of a nucleic acid molecule of defined sequence from a complex mixture. We form double D-loops as described in Example 14 with the following exceptions: we use LDB/45G at a concentration of 18 µM and 5 units of topoisomerase I; the target nucleic acid is a 1:1 mixture of supercoiled pBR322 (AP$^R$, Tet$^R$) and the supercoiled Kan$^R$ plasmid used in Example 14; and the reaction is incubated for 1 hour at 37° C. after addition of the target and topoisomerase I. LDB/45G has the same sequence as LDF/45G (used in Example 10), except that LDB/45G is not labeled with Cy™5 and has a biotin molecule attached at the 3' end by a TEG linker (5'-GGTGGAGAGGCTATTCG-GCTAGGACTGGGCACAACAGACAATCGG-3'bioTEG; SEQ ID NO: 52). Neither the incoming oligonucleotide (LDF/45G) or the annealing oligonucleotide (KLO2) has significant sequence complementarity to any sequence in pBR322.

We denature the RecA by cooling the reaction to about 4° C. by placing it in an ice bath and adding 2 µl 10% SDS as above. We then add KCl to a final concentration of 100 mM to precipitate the SDS, spin at 5000 rpm for 5 minutes in a microcentrifuge to pellet the precipitated SDS and transfer the supernatant to another tube. We add 2 µl of Dynabeads™ diluted in 1× Synaptic Buffer and incubate the reaction for 2 hours at 4° C. with vertical rotation to mix the solution. We then separate the magnetic Dynabeads™ by placing in a magnetic tube holder for 5 minutes and remove the supernatant. We wash twice in 1× TE buffer (GibcoBRL) by suspending the pellets in 50 µl ice-cold TE and agitating for 5 minutes at 4° C., separating the magnetic Dynabeads™ by placing in a magnetic tube holder for 5 minutes at 4° C. and removing the supernatant. We elute the plasmid DNA from the Dynabeads™ by adding 10 µl TE and heating the solution at 65° C. for 15 minutes. We collect the eluant and mix 5 µl with 20 µl electrocompetent DH10B cells. We electroporate the sample in a Cell-Porator® set at 330 µF, 4 Ω and 400 V. We remove the cells and place them in 1 ml of SOC medium and allow them to recover by incubating at 37° C. for 1 hour. We then dilute the cells into 4 ml of SOC medium and incubate on a shaker at 37° C. for 2 hours. We spin the cells down in a table top centrifuge for 5 minutes at 3750 rpm and resuspend the cells in 750 µl LB. We dilute these cells 1:10 into fresh LB and plate 100 µl of cells on LB plates supplemented with either 10 µg/ml tetracycline or 20 µg/ml kanamycin. We incubate the plates at 37° C. overnight and count the colonies after approximately 16 hours.

We observe extremely clean purification of the target plasmid. See Table 3. We are unable to determine the efficiency of purification because we observe no background colonies. These results indicate that the double D-loops formed according to the methods of the invention can be used to purify a nucleic acid molecule of known sequence away from other nucleic acid molecules.

TABLE 3

Separation of Kan$^R$ plasmid from pBR322 using double D-loops

| Sample | Tet$^R$ Colonies | Kan$^R$ Colonies |
|---|---|---|
| No Dynabeads ™ | >5000 | >5000 |
| No annealing oligonucleotide | 0 | 0 |
| No RecA | 0 | 6 |
| Complete reaction | 0 | 163 |

We also test whether the sequence specificity of double D-loop formation can be used for purification of a large nucleic acid molecule, for example a YAC. We inoculate a 5 ml culture of growth medium with a single colony from a YAC-containing strain of yeast and allow it to grown overnight until saturated. The following day we inoculate an additional 100 ml culture of growth medium with 1 ml of the overnight starter culture and grow this culture overnight until saturated. We use a hemocytometer to determine the cell count, which is generally about 1×10$^8$ cells/ml. We harvest the cells by centrifugation at 1300×g for 5 minutes and wash the pellet twice with 50 mM EDTA pelleting between washes for 5 minutes at 1300×g. We resuspend the cells in 50 mM EDTA to a concentration of 2×10$^9$ cells/ml and warm the cell suspension to 45° C. for 5 minutes. We add an equal volume of 1% InCert agarose in 50 mM EDTA, also prewarmed to 45° C. Alternatively, we use 1% or 2% SeaPlaque agarose. We mix the suspension by vortexing and pipet 500 µl aliquots into an agarose plug mold to harden. A 100 ml culture will yield about 20 plugs. We allow the plugs to set at room temperature or at 4° C. which takes about 15 minutes.

We extrude each plug into a dish and add 6 ml of freshly prepared yeast spheroplasting solution (40 ml 1 M sorbitol; 1.6 ml 0.5 M EDTA, pH 8.0; 0.4 ml 1 M Tris-HCl, pH 7.5; 40 µl 2-mercaptoethanol; and 40 mg yeast lytic enzyme (ICN)). We incubate the plugs at 37° C. for 2 to 4 hours with gentle shaking. We aspirate off the spheroplast solution, add 6 ml of LDS solution (1% lithium dodecyl sulfate; 100 mM EDTA; and 10 mM Tris-HCl, pH 8.0) and incubate at 37° C. with gentle shaking for 1 hour. We remove the solution and add 6 ml fresh LDS solution and incubate with gentle shaking at 37° C. overnight. We wash the plugs three times with gentle shaking at room temperature for 30 minutes with 6 ml 0.2× NDS (1×NDS is 0.5 M EDTA; 10 mM Tris base; 1% Sarkosyl; pH 9.5). We then wash the plugs five times with gentle shaking at room temperature for 30 minutes with 6 ml TE, pH 8.0. Plugs are either used directly or stored at 4° C. in covered with TE, pH 8.0.

We form a double D-loop in the YAC DNA in the agarose plug. We coat an incoming biotinylated oligonucleotide with RecA using a 5× amount of reactants as described in Example 10. We soak the plug in the solution containing the RecA-coated incoming oligonucleotide at 37° C. for between 20 minutes and 2 hours. We then add 5× volume of annealing oligonucleotide to the plug and soak for an additional 10 minutes to 1 hour. We insert the plug into a pulse field electrophoresis gel containing low melt agarose and a strip of conjugated agarose-streptavidin. We run the pulse field gel such that the DNA migrates across the streptavidin containing band allowing the YAC DNA containing the biotinylated double-D loop to be captured by the band. We excise the strip, heat it to melt the agarose, and elute the target from the band. We then transform spheroplasted yeast cells with the eluant by lithium acetate transformation.

EXAMPLE 16

Double D-Loop Hybridization Reactions Can Discriminate Single Basepair Differences in Target Sequences We test whether the sequence specificity of double D-loop formation can be used to discriminate single basepair differences in a target sequence. We form the double D-loop as described in Example 10 except that we use a 50:50 mixture of two incoming oligonucleotides.

For example, we use 0.55 µl of an 18 µM solution of LDF/31G (5'-Cy™5-GAGGCTATTCGGCTAG-GACTGGGCACAACAG-3'; SEQ ID NO: 53) and 0.55 µl of an 18 µM solution of LDF/31C (5'-Cy™3-GAGGCTAT-TCGGCTACGACTGGGCACAACAG-3'; SEQ ID NO: 54). The incoming oligonucleotide LDF/31G is complementary to the sequence of the mutant Kan$^R$ gene with the nucleotide corresponding to the point mutation centrally positioned and the incoming oligonucleotide LDF/31C is fully complementary to the sequence of a functional Kan$^R$ gene. The RecA-coated mixture of incoming oligonucleotides is added separately to either the Kan$^-$ or the Kan$^+$ PCR product. We add KM2 (SEQ ID NO: 39) as the annealing oligonucleotide. The KM2 oligonucleotide is perfectly complementary to the Kan$^-$ target sequence. We also perform this experiment with an individual annealing oligonucleotide specific for the Kan$^+$ target sequence and with a mixture of the two oligonucleotides. We perform these experiments with annealing oligonucleotides comprising a variety of combinations of modfied backbones or bases, including, for example, LNA, PNA, 2'-O-methyl RNA and 2-aminoadenine or cytosine/uracil substituted at the 5 position with a methyl, propynyl or bromo group.

We test the stability of the double D-loops formed as described above by denaturing the RecA bound to the oligonucleotide:target complex by adding SDS and, optionally KCl, and heating the samples to various temperature, e.g. 37° C., for varying periods of time. We then analyze the samples by separating by agarose gel electrophoresis. We monitor the stability of the double D-loops under these assay conditions by detecting the fluorescent labels on the Cy™3- and Cy™5-labeled oligonucleotides. The migration of these labeled oligonucleotides is retarded when they are part of a double D-loop complex.

We observe that double D-loop complexes in which the labeled incoming oligonucleotide is mismatched to the template are significantly less stable after denaturing the RecA than complexes in which the oligonucleotide is perfectly complementary to the template. This difference is readily detectable and after only 2.5 minutes at 37° C. a double D-loop made with a mismatched annealing oligonucleotide is almost completely undetectable. Accordingly, it is possible to determine which target sequence is in a sample based on which fluorescently labeled incoming oligonucleotide is present in the complex. This result indicates that stable double D-loops may be used to detect a single-nucleotide polymorphism in a target sequence or a mixture of target sequences.

EXAMPLE 17

Double D-Loop Hybridization Reactions Can Discriminate Single Basepair Differences in a Genomic Target Sequence We test the effect of varying the annealing oligo sequence to double D-loop formation efficiency in genomic DNA. We form double D-loops as in Example 16 using a 50:50 mixture of HYG(NT)D5Cy5/31C(rep) (5'-Cy™5-ATTTACCCG-CAGGACCTATCCACGCCCTCCT-3'; SEQ ID NO: 55) which is perfectly matched to a hygromycin resistance gene with a point mutation (Hyg$^-$) and HYG/(NT)D5Cy3/31G (cnv) (5'-Cy™3-ATTTACCCGCAGGACGTATCCACGC-CCTCCT-3'; SEQ ID NO: 56) which is perfectly matched to a copy of the hygromycin resistance gene which contains a point mutation but which remains functional (Hyg$^+$). We add this to a genomic prep from two yeast strains, one from Mata-intHyg$^-$ which contains an integrated Hyg$^-$ gene. We compare this to a genomic prep of Mata-intHyg$^+$ strain which contains an integrated Hyg$^+$ gene. We use the following annealing oligonucleotides which are composed of LNA residues except for the underlined bases which are DNA: HygLNA15T (5'-GT<u>G</u>GAT<u>A</u>GGT<u>C</u>CTGC-3'; SEQ ID NO: 57) which is perfectly matched to Hyg$^-$, Hyg15LNAT(cnv)C (5'-GT<u>G</u>GAT<u>A</u>CGT<u>C</u>CTGC-3'; SEQ ID NO: 58) which is perfectly matched to Hyg$^+$, and Hyg15LNAT(wt)T (5'-GT<u>G</u>GAT<u>A</u>TGT<u>C</u>CTGC-3'; SEQ ID NO: 59) which is perfectly matched to the wild-type, functional hygromycin resistance gene sequence (Hyg(wt)). We add SDS to remove the RecA at 37° C. for 30 seconds, and run on a 0.7% agarose gel at 4° C.

Figure 17:
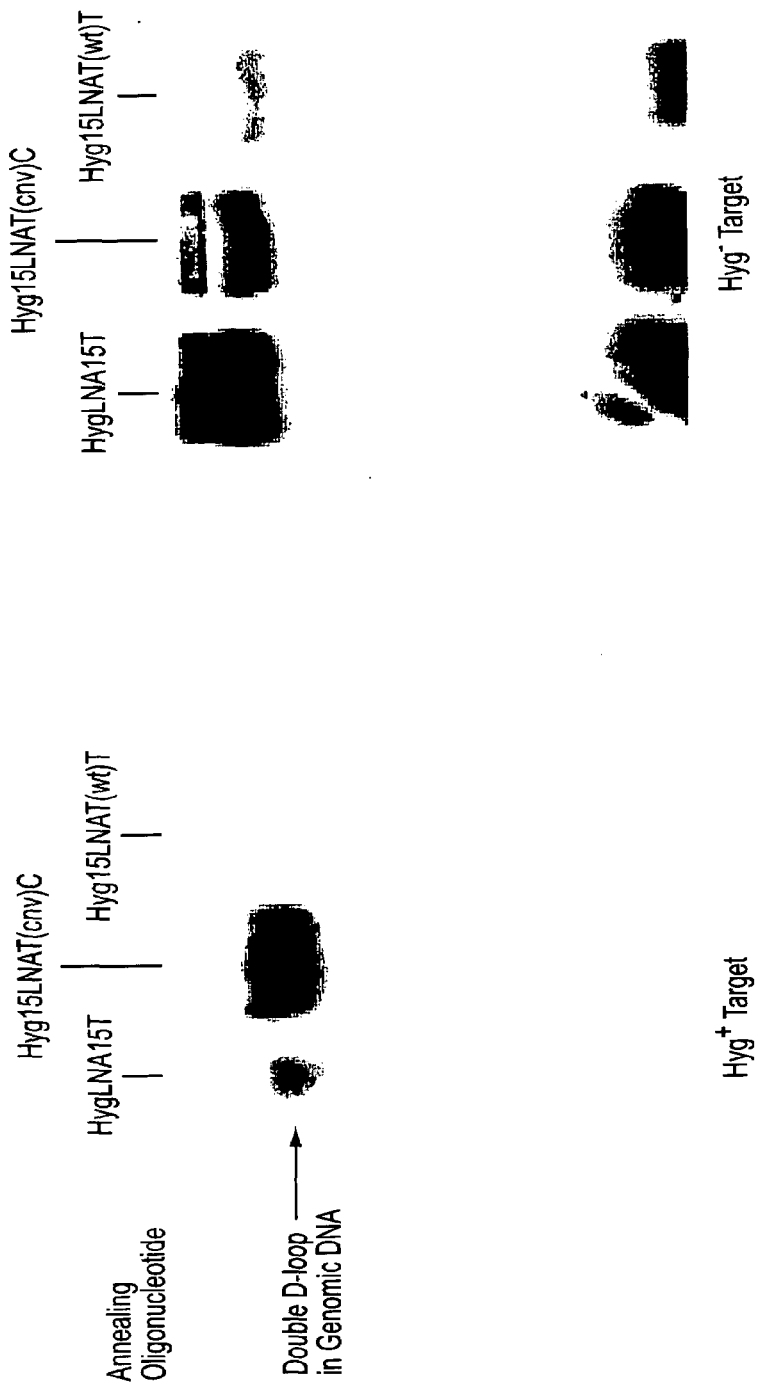
FIG. 17 shows double D-loop formation according to embodiments of the present invention in yeast genomic DNA from a strain with an integrated copy of a Hyg⁻ target and from a strain with an integrated copy of a Hyg⁺ target.

We observe efficient double D-loop formation in a genomic DNA target, indicating that target size and complexity do not limit the reaction. See FIG. 17. We also observe a readily detectable effect of the LNA sequence on formation efficiency. The presence of a mismatch on the annealing strand significantly destabilizes the molecule, as in Example 16. Accordingly, it is possible to discern the sequence of the target from a genomic DNA prep with high accuracy.

We also analyze metaphase chromosome spreads obtained from mammalian cells, including human cells. For example, we combine 0.5 to 0.8 ml whole blood with 0.2 ml phytohemaglutinin (PHA; M-form lyophilized from GibcoBRL or Sigma dissolved according to the manufacturer's instructions) and mix gently. The cells are added to a flask with 10 ml of complete cell culture media and we incubate them at 37° C. for 72 hours. We add 0.1 ml Actinomycin-D (5 mg/10 ml water) and incubate for 20 minutes. We then add 0.1 ml of colcemid (10 µg/ml; GibcoBRL) and incubate for 10 more minutes. We centrifuge the cells at 1000 rpm for 8 minutes, aspirate the supernatant and break up the cell pellet using a polyethylene pipet. We lyse the cells by adding prewarmed 37° C. hypotonic solution (75 mM KCl) drop by drop, mixing gently after each addition wth the pipet, until the final volume reaches about 2 ml. We then add a larger amount of hypotonic solution to bring the total volume to 10 ml and incubate at 37° C. for 15 minutes. We then at 10 drops of fixative solution (3 parts absolute methanol:1 part glacial acetic acid) and mix with the pipet. We then centrifuge the cells at 1000 rpm for 8 minutes, aspirate the supernatant and break up the cell pellet using a polyethylene pipet. We add fixative solution drop by drop, mixing gently after each addition wth the pipet, until the final volume reaches about 2 ml. We then add a larger amount of fixative solution to bring the total volume to 10 ml. We then use these cells directly or store them in a refrigerator overnight.

We make slides with the cells as follows. We pellet the cells 20 minutes after the first addition of fixative solution by centrifuging at 1000 rpm for 8 minutes. We remove the supernatant using an aspirator, break up the cell pellet with the pipet, and resuspend in 10 ml of fixative solution by mixing gently. We repeat the pelleting and resuspending steps two more times. After the final resuspension, we leave 0.5 ml to 3.0 ml of fixative solution above the cell pellet, mix and drop four to six drops of cell suspension onto a clean wet slide. We then allow the slide to either air dry or place it on a hot plate at 55° C.-60° C. to dry.

We test the ability of the double D-loop formed according to the methods of the invention to discriminate single basepair differences in a genomic target sequence. We incubate the slides with two RecA-coated incoming oligonucleotides, each specific for a target sequence corresponding to the two interrogated alleles and each separately labeled, for example with Cy™-3 and Cy™5. We then add two annealing oligonucleotides complementary to the incoming oligonucleotides. We determine the sequence of the target by destabilizing the mismatched double D-loop by denaturing RecA and detecting the label on the oligonucleotide in the resulting double D-loop.

Alternatively, for detection of a target sequence in the genome, the slides are incubated sequentially with incoming and annealing oligonucleotides complementary to a desired genomic target. One of these oligonucleotides is labeled with a detectable moiety which is monitored to detect the formation of a stable double D-loop.

EXAMPLE 18

Assessment of Gene Amplification By Detecting Double D-Loop Formation

We test the ability of double D-loop formation to detect multiple copies of a gene in a genome. We use two strains of yeast containing one or multiple copies of the Hyg(rep) gene. We extract the genomic DNA and form double D-loops using the same conditions as described in Example 17, using HygUDF45G as the incoming oligo, and HygLNA15T as the annealing oligo. We run the reaction on a 1% agarose gel and quantify the amount of double D-loop formed using Molecular Dynamics ImageQuant™ and a Typhoon™ imager.

We observe that the intensity of double D-loop band increases in proportion to copy number of the inserted gene. This indicates that detection of double D-loop formation can be used to quantify amplification of a target duplex nucleic acid molecule, including a target gene such a ERB2 and c-Myc.

EXAMPLE 19

Sequence Specific Cleavage of Nucleic Acid Molecules Using Double D-Loops

We test whether the sequence specificity of double D-loop formation can be used to direct cleavage of a target nucleic acid molecule at a desired location. We form double D-loop targets by sequential hybridization. We combine oligonucleotides in two separate tubes as follows. In one tube we combine 7 µl of a 4 µM solution of $^{32}$P-labeled 70mer oligonucleotide (OligoA; SEQ ID NO: 1); 1.9 µl of a 13 µM solution of a 25mer oligonucleotide (LD25G; 5'-GCTATTCGGCTAG-GACTGGGCACAA-3'; SEQ ID NO: 60); and 0.75 µl 10× hybridization buffer (100 mM Tris-HCl pH 7.5). In a second tube we combine 1.92 µl of a 12.5 µM solution of another 70mer oligonucleotide (OligoB; SEQ ID NO: 2); 1.46 µl of a 16.4 µM solution of another 25mer oligonucleotide (UD25C; 5'-TTGTGCCCAGTCCTAGCCGAATAGC-3'; SEQ ID NO: 61); 0.76 µl 10× hybridization buffer; and 3.46 µl water. These oligonucleotides are complementary to each other as follows: OligoA and OligoB are complementary; LD25G and UD25C are complementary; LD25G is complementary to OligoA such that LD25G hybridizes approximately in the center of OligoA; and UD25C is complementary to OligoB such that UD25C hybridizes approximately in the center of OligoB. We heat each of the separate tubes to 95° C. for 2 minutes and then cool to 60° C. for 20 minutes. This allows for OligoA/LD25G and OligoB/UD25C duplexes to form in the separate tubes. We then mix the tubes and incubate for 5 minutes at 37° C. This allows the overhanging ends on OligoA and OligoB to hybridize forming a double D-loop structure. We then cool the samples to 4° C. and separate the samples on a non-denaturing 12% polyacrylamide gel run at 4° C. for 2.5 hours at 8 W.

We detect the location of the double D-loops in the polyacrylamide gel by autoradiography and excise the band corresponding to the double D-loop. We incubate the polyacrylamide gel slice containing the double D-loops at 4° C. overnight in 1 ml of 2 mM Mg(acetate)$_2$ to elute the double D-loops from the gel slice. We transfer 250 µl of the solution containing the double D-loops into four different microfuge tubes and add 750 µl cold ethanol and 1 µg of poly dI-dC as a DNA carrier. We incubate this sample at 4° C. overnight and pellet the precipitate double D-loops by centrifugation at in a microcentrifuge at 4° C. for 30 minutes at 13,500 rpm. We aspirate the supernatant and wash the pellet by adding 200 µl 70% ethanol, centrifuging at 4° C. for 15 minutes at 13,500 rpm and aspirating the supernatant. We dissolve the double D-loops in 100 µl of 1× TBM (90 mM Tris-borate; 1 mM MgCl$_2$). We either use the double D-loops immediately or store at −20° C.

We combine 2 µl of $^{32}$P-labeled double D-loops in a reaction mix with 1 µl reaction buffer (300 mM BisTris-HCl pH 7.0; 500 mM KCl; 25 mM MnCl$_2$; 500 µg/ml BSA and 10 mM DTT), 0.5 µl MRE11 protein purified from *Saccaromyces cerevisiae*, 20 mM ATP and 4.5 µl water. optionally, we include 0.5 µl RAD50 purified from *Saccaromyces cerevisiae*. If RAD50 is added, we add 4 µl water. We incubate this mixture for 30 minutes at 37° C. to allow MRE11-mediated cleavage of the target. We separate the reaction by either a non-denaturing 12% polyacrylamide gel electrophoresis or by denaturing (7M urea) 20% polyacrylamide gele electrophoresis.

We observe approximately 60% cleavage of the target nucleic acid molecule, i.e. approximately 40% of the $^{32}$P-labeled 70mer oligonucleotide. The cleavage that we observe is highly specific, with about 80% of cleavage occuring at the ends of the double D-loop. The localization of the cleavage site to the junction of the double D-loop at the 5' end of the incoming and annealing oligonucleotides indicates that it is possible to select a specific cleavage site by selecting specific incoming and annealing oligonucleotides. Accordingly, it is possible using this method to site-specifically cleave at any given base in a nucleic acid target with a defined sequence.

EXAMPLE 20

Double D-Loop Formation in Membrane-Bound Nucleic Acid Targets

We test the efficiency of double D-loop formation on a target crosslinked to a membrane. We crosslink via a Stratalink various concentrations of linear Hyg$^-$ plasmid onto a Hybond-N+ (Amersham) membrane. We block the membrane by incubating at room temperature for 30 minutes with various concentrations of Denhardt's solution (100×: 2% BSA, 2% Ficoll, 2% PVP (polyvinylpyrrodilone)). We separately form the RecA filament using the same conditions as Example 10, with HygUDF45G with 5× the amount of reactants. We dilute the reaction to a final volume of 1 mL in 1× Synaptic buffer. Subsequently, we add the membrane to the reaction and incubate for 20 minutes at 37° C. We then add the 3.7 µL of 27 µM HYGLNA15T, and incubate 10 minutes at 37° C. We subsequently wash the membrane in various concentrations of SSC (20×: 3M NaCl, 0.3M Na$_3$Citrate) at elevated temperatures (37-65° C.), and visualize on the Molecular dynamics Typhoon™ Imager.

We observe efficient formation of double D-loop in a target crosslinked to a membrane. This results demonstrates that the methods of the invention can be used to form double D-loops in DNA crosslinked to a solid support such as a membrane, glass slide, or 96 well plate, with no serious detrimental effects. We can, thus, form a double-D loop sequence specifically, and visualize its structure without running a gel. Visualization of the formation of a stable double D-loop with a perfectly matched oligonucleotide as compared to the absence of a stable double D-loop structure with a mismatched oligonucleotide allows easy visualization of single nucleotide polymorphisms (SNPs).

EXAMPLE 21

Single Nucleotide Mismatch Discrimination in an 8 KB Plasmid Target Using PNA Annealing Oligonucleotides In this example, we test the ability to discriminate single nucleotide differences in an 8 kb nonsupercoiled plasmid target using annealing oligonucleotides composed of PNA.

Materials and Methods

Target Plasmids:

mt ("mutant"): pAURHyg(rep)eGFP

WT ("wild type"): pAURHyg(wt)eGFP

The plasmids are each 7982 bp, and differ in a single nucleotide. As a consequence of plasmid purification, a subset of the plasmids are no longer supercoiled, having been nicked or otherwise broken. Upon gel electrophoresis, a single band having various nonsupercoiled topoisomers can be observed.

Incoming Oligonucleotides:

Incoming oligonucleotides are HPLC purified, and have the following sequences.

```
mt: HYG(NT)D5Cy5/31C(rep)
                                    (SEQ ID NO: 55)
(5'-Cy5-atttacccgcaggacctatccacgccctcct-3')

WT: HYG(NT)D5Cy3/31A(wt)
                                    (SEQ ID NO: 62)
(5'-Cy3-atttacccgcaggacatatccacgccctcct-3')
```

Annealing Oligonucleotides:

Annealing oligonucleotides are composed of PNA, with an acetyl group ("Ac") to block a free reactive primary amine. The annealing oligonucleotides are used as received from Applied Biosystems, Inc. (crude prep).

```
mt: HYG(T)PNA/15G
    (Ac-gtggataggtcctgc)        (SEQ ID NO: 57)

WT: HYG(T)PNA/15T
    (Ac-gtggatatgtcctgc)        (SEQ ID NO: 63)
```

Protocol:
1. Prepare reaction mix (add RecA last) as follows:
   1.1 μL incoming oligo mix (18 μM)
      0.55 μL of 18 μM Hyg(nt)D5Cy5/31C(rep) (Cy-5 labeled)
      0.55 μL of 18 μM Hyg(nt)D5Cy3/31A(wt) (Cy-3 labeled)
   3 μL 5× Synaptic Buffer
   1.5 μL 10 mM ATPγS
   7.4 μL dH2O
   2 μL RecA (10.9 μM)
   15 μL
2. Incubate for 10 minutes at 37° C.
3. Add the following:
   2.5 μL (500 ng) nonsupercoiled target
      Hyg(rep) or Hyg(wt) target
   2.5 μL Mg(OAc)$_2$ (74 mM)
   20 μL
4. Incubate for 20 minutes at 37° C.
5. Add one or the other annealing oligo (at 36.5 μM)
   0.50 μL HYG(T)PNA/15G or
   0.50 μL HYG(T)PNA/15T
6. Incubate for 5 minutes at 37° C.
7. Stop reaction with 2 μL 10% SDS and incubate respectively under the following conditions:

| | Hyg(rep) | | | Hyg(wt) | |
|---|---|---|---|---|---|
| 1. | 37° C. | 0 min | 11. | 37° C. | 0 min |
| 2. | | 1 min | 12. | | 1 min |
| 3. | | 2.5 min | 13. | | 2.5 min |
| 4. | | 5 min | 14. | | 5 min |
| 5. | | 10 min | 15. | | 10 min |
| 6. | 45° C. | 0 min | 16. | 45° C. | 0 min |
| 7. | | 1 min | 17. | | 1 min |
| 8. | | 2.5 min | 18. | | 2.5 min |
| 9. | | 5 min | 19. | | 5 min |
| 10. | | 10 min | 20. | | 10 min |

After the indicated incubation time, place samples on dry ice.
8. Run gel:
   Add 10 μL of 10× loading dye (w/25% ficoll). Run on a 1× TBE, 1% agarose gel without EtBr at 4° C.
   Run gels at 120V for about 2 hours.
9. Scan on Typhoon Imager
10. Optional post-staining (not shown in FIGS. 18A and 18B)
    Stain with 1× SYBR green and scan on Typhoon imager Results The target in these experiments is one of two nonsupercoiled plasmids of about 8 kb, differing in a single nucleotide. The incoming oligonucleotides are 31-mer deoxyribonucleotides labeled at the 5' terminus with either Cy5 or Cy3; the annealing oligonucleotides are 15-mer PNA oligonucleotides acetylated at the N terminus. Deproteinization is performed by adding SDS at either 37° C. or 45° C. to aliquots of the reaction mixture and incubating at the indicated temperature for various amounts of time, after which time the aliquots are removed and placed on dry ice.

Two gels are run separately, but scanned at the same time to allow a direct comparison. Results are shown in FIGS. 18A and 18B for the 37° C. deproteinization data only.

Figure 18A:
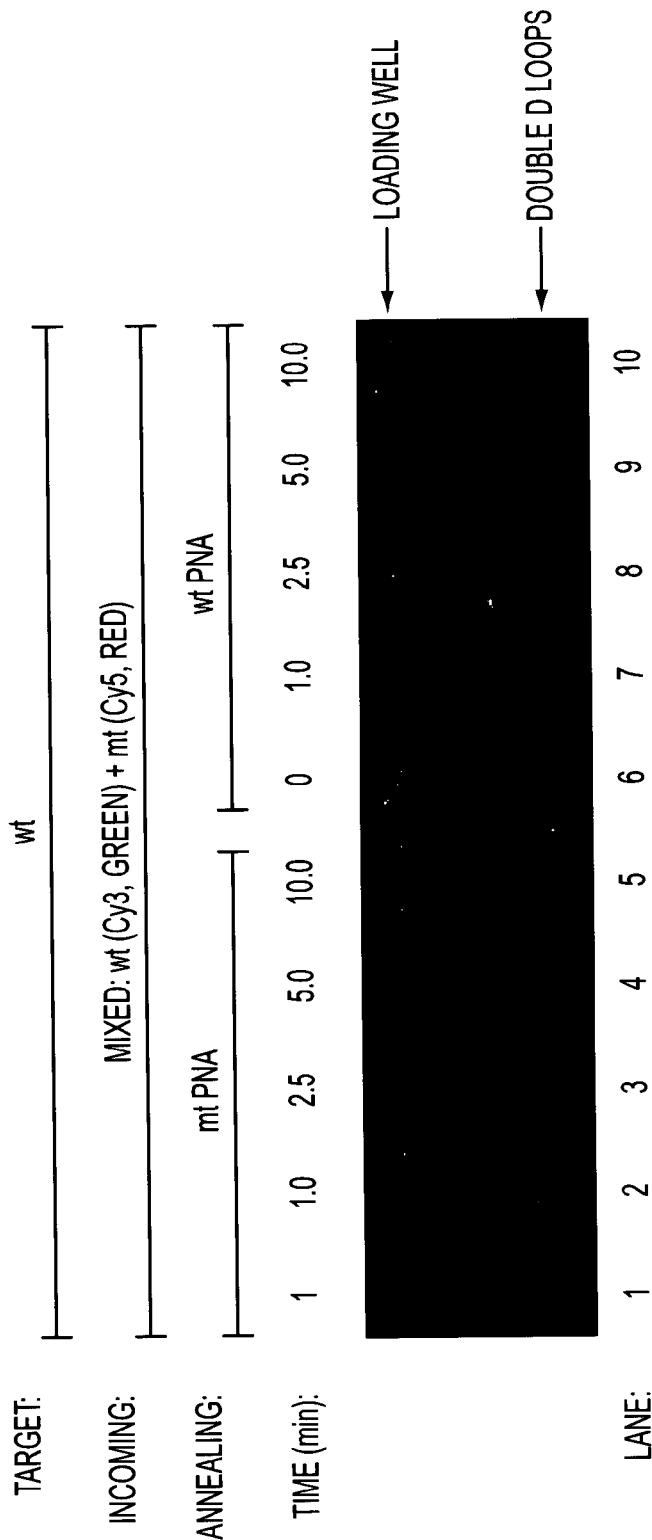
FIGS. 18A and 18B are two color fluorescence scans of electrophoresis gels showing single nucleotide mismatch discrimination in an 8 kb plasmid target using PNA annealing oligonucleotides according to embodiments of the present invention.
Figure 18B:
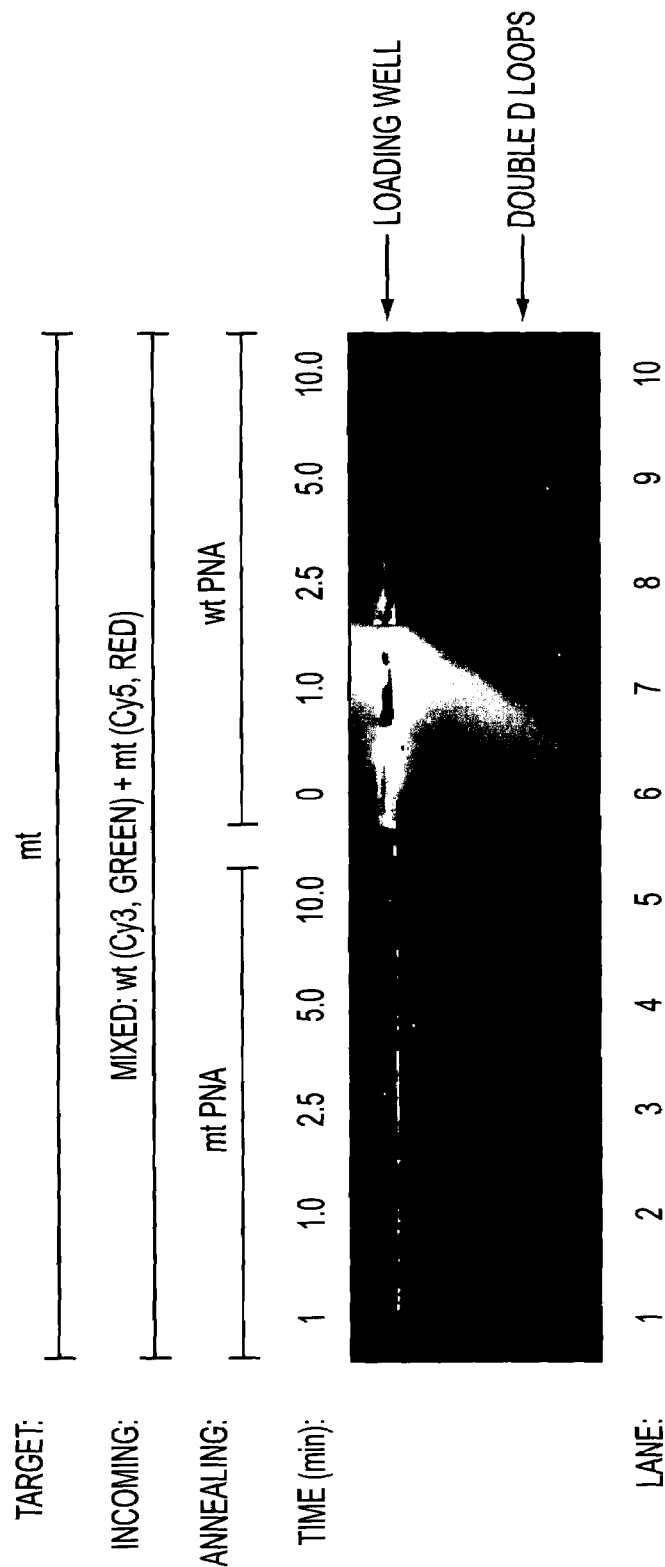

Despite the small size of the incoming and annealing oligonucleotides and the large target (8 kb), results shown in FIG. 18A (wt target pAURHyg(wt)eGFP) and FIG. 18B (mt target pAURHyg(rep)eGFP) demonstrate that the single nucleotide difference in the target query region can readily be distinguished, with stable double D loops (stable to deproteinization and subsequent electrophoresis) observed only when the annealing oligonucleotide and incoming oligonucleotide exactly match the target.

Furthermore, discrimination among target variants differing by a single nucleotide is achieved in the presence of a mixture of differentially labeled incoming oligonucleotides, demonstrating the ability to multiplex these assays.

In additionally, the gels demonstrate that the targets having stable double D loops are readily separated from those without, making possible the isolation of desired allelic variants.

Although lanes 6 and 7 of FIG. 18B suggest that stable double D loops are formed on the mutant (mt) target with a mismatched annealing oligonucleotide (wt PNA), these data are not representative, and may be due to the bright background in this part of the gel, which may artificially enhance the signals to detectable levels; most of our gels show no formation of stable double D loops unless all oligos (incoming and annealing) are perfectly matched to target.

In data that are not shown, the stringent requirement for both a perfectly matched incoming and perfectly matched annealing oligonucleotide to effect stable D loop formation is not observed with supercoiled plasmids.

For example, in the absence of a perfectly matched annealing oligonucleotide, we observe that perfectly matched incoming oligonucleotides can form stable single D loops, whereas incoming oligonucleotides mismatched by a single nucleotide do not. In the presence of a perfectly matched annealing oligonucleotide, stable double D loop formation is observed even when the incoming oligonucleotide is mismatched to target by one nucleotide. In this latter case, discrimination of allelic targets is enhanced when the label is on the annealing oligonucleotide.

EXAMPLE 22

Single Nucleotide Mismatch Discrimination in an 8 KB Plasmid Target Using LNA Annealing Oligonucleotides In this example, we detect a single nucleotide mismatch in an 8 kb plasmid target using LNA annealing oligonucleotides.

Materials and Methods
Target Plasmids:
Targets are the same as in Example 21: 8 kb nonsupercoiled plasmids differing in a single nucleotide.
  mt: pAURHyg(rep)eGFP
  WT: pAURHyg(wt)eGFP
Incoming Oligonucleotides:
Incoming oligonucleotides are HPLC purified.
  mt: HYG(NT)D5Cy5/31C(rep) (5'-Cy5-atttacccgcaggac-ctatccacgccctcct-3') (SEQ ID NO: 55)
  WT: HYG(NT)D5Cy3/31A(wt) (5° Cy3-atttacccgcagga-catatccacgccctcct-3') (SEQ ID NO: 62)
Annealing Oligos:
Annealing oligos containing LNA residues, synthesized by Proligo, are used as a crude prep. In the sequences listed below, LNA residues are prefixed by a "+" sign and deoxyribonucleotide residues are prefixed by a lower case "d".

mt: HYGLNA15T (5'-+G+TdG+G+A+TdA+G+G+TdC+C+T+G+C-3'-3') [SEQ ID NO: 57]
WT: HYG(T)LNA15T(wt) (5'-+G+TdG+G+A+TdA+T+G+TdC+C+T+G+C-3') [SEQ ID NO: 63]
Protocol:
Reactions are essentially as set forth in Example 21.

Results

Figure 19:
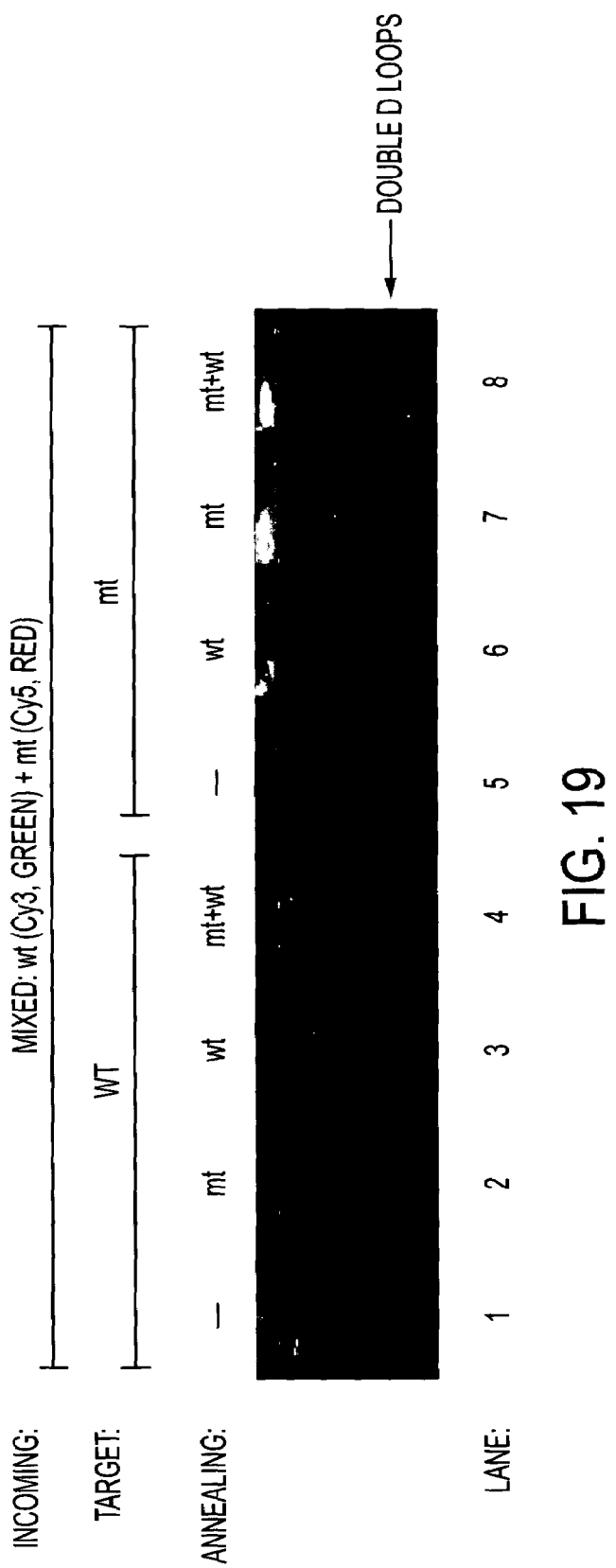
FIG. 19 is a two color fluorescence scan of an electrophoresis gel showing single nucleotide mismatch discrimination in an 8 kb plasmid target using LNA annealing oligonucleotides according to embodiments of the present invention.
Figure 20:
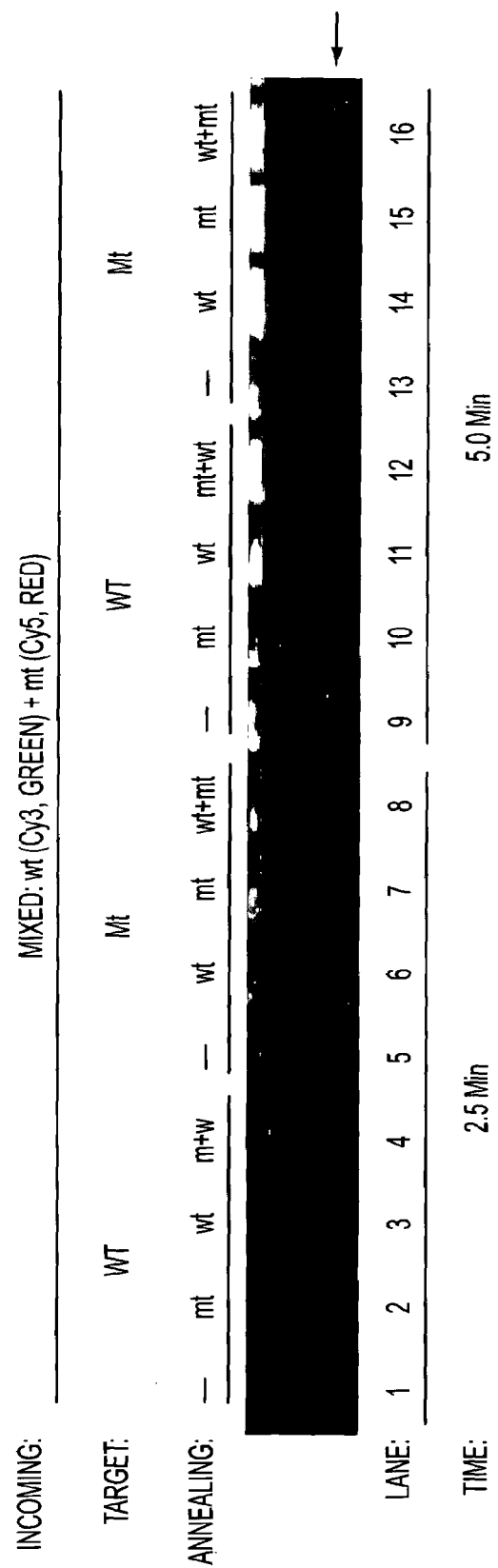
FIG. 20 is a two color fluorescence scan of an electrophoresis gel showing single nucleotide mismatch discrimination in an 8 kb plasmid target using LNA annealing oligonucleotides according to embodiments of the present invention, with temperatures as indicated.

FIG. 19 shows data from reactions stopped by addition of SDS at 37° C. followed by immediate freezing on dry ice; FIG. 20 shows data from reactions stopped by addition of SDS at 37° C. followed by 2.5 minute and 5 minute incubations at 37° C., as indicated, prior to freezing on dry ice.

As in Example 21, results shown in FIGS. 19 and 20 demonstrate that stable double D loops are formed only when both annealing and incoming oligonucleotides are perfectly matched to target. In contrast to Example 21, the annealing oligonucleotide comprises LNA residues, rather than PNA residues.

The data further demonstrate that single nucleotide variants of this 8 kb nonsupercoiled plasmid can be distinguished when both the incoming and annealing oligonucleotides are present in admixture, demonstrating the robust multiplexing capabilities of this approach.

EXAMPLE 23

Single Nucleotide Mismatch Discrimination in a Linear Target Without Competing Oligonucleotides The preceding two examples demonstrate that our assay provides excellent discrimination between two 8 kb plasmid targets differing by a single nucleotide, under conditions in which incoming oligonucleotides and/or annealing oligonucleotides that are perfectly matched to target are present in admixture with oligonucleotides that are not perfectly matched to target. In this example, we test whether similar selectivity (mismatch discrimination) is observed if no competing oligonucleotides are present.

In addition, the preceding two examples do not distinguish among various nonsupercoiled topoisomers of the 8 kb plasmid (linear, nicked, covalent closed circular). In this example, we test whether equivalent selectivity is observed in a linear target as large as 8 kb. In these experiments, therefore, we use one target, 8kb EcoRV-linearized pAURHyg(rep)eGFP plasmid, and the indicated combinations of oligonucleotides.

Materials and Methods
Target:
8kb EcoRV-linearized pAURHyg(rep)eGFP
Incoming Oligos:
HPLC purified
mt: HYG(NT)D5Cy5/31C(rep) (5'-Cy5-atttacccgcaggac-ctatccacgccctcct-3') [SEQ ID NO: 55]
WT: HYG(NT)D5Cy3/31A(wt) (5'-Cy3-atttacccgcagga-catatccacgccctcct-3') [SEQ ID NO: 62]
Annealing Oligos:
Synthesized by Proligo, used as a crude prep. LNA residues are prefixed by "+"; deoxyribonucleotides are prefixed by "d".
mt: HYGLNA15T (5'-+G+TdG+G+A+TdA+G+G+TdC+C+T+G+C-3') [SEQ ID NO: 57]
WT: HYG(T)LNA15T(wt) (5'-+G+TdG+G+A+TdA+T+G+TdC+C+T+G+C-3') [SEQ ID NO: 63]
Protocol:
1. Prepare reaction mix
   1.1 μL Incoming oligo (18 μM)
   2 μL 10× Syn Comp Buffer*
   12.74 μL dH2O
   1.16 μL RecA (10.9 μM) (added last)
   17 μL total
2. Incubate for 10 minutes at 37° C.
3. Add the following:
   2 μL Linear Hyg(rep) (250 ng/μl)
   19 μL total
4. Incubate for 10 minutes at 37° C.
5. Add 1 μL of annealing oligo (38.5 μM)
6. Incubate for 10 minutes at 37° C.
7. Stop reaction with 2 μL 10% SDS, put on ice or dry ice.
8. Run gel
   Add 10 μL of 10× loading dye (w/25% ficoll)
   Run on a 1XTBE, 1% agarose gel without EtBr
   * 10× Syn Comp Buffer:
   250 mM Tris-OAc pH7.15
   50 mM Mg(OAc)$_2$
   10 mM DTT
   10 mM ATPγS
   5× Denhardts
     (1 g ficoll400, 1 g PVP and 1 g
     BSA Fraction V in 50 ml H$_2$O)

Results

Figure 21:
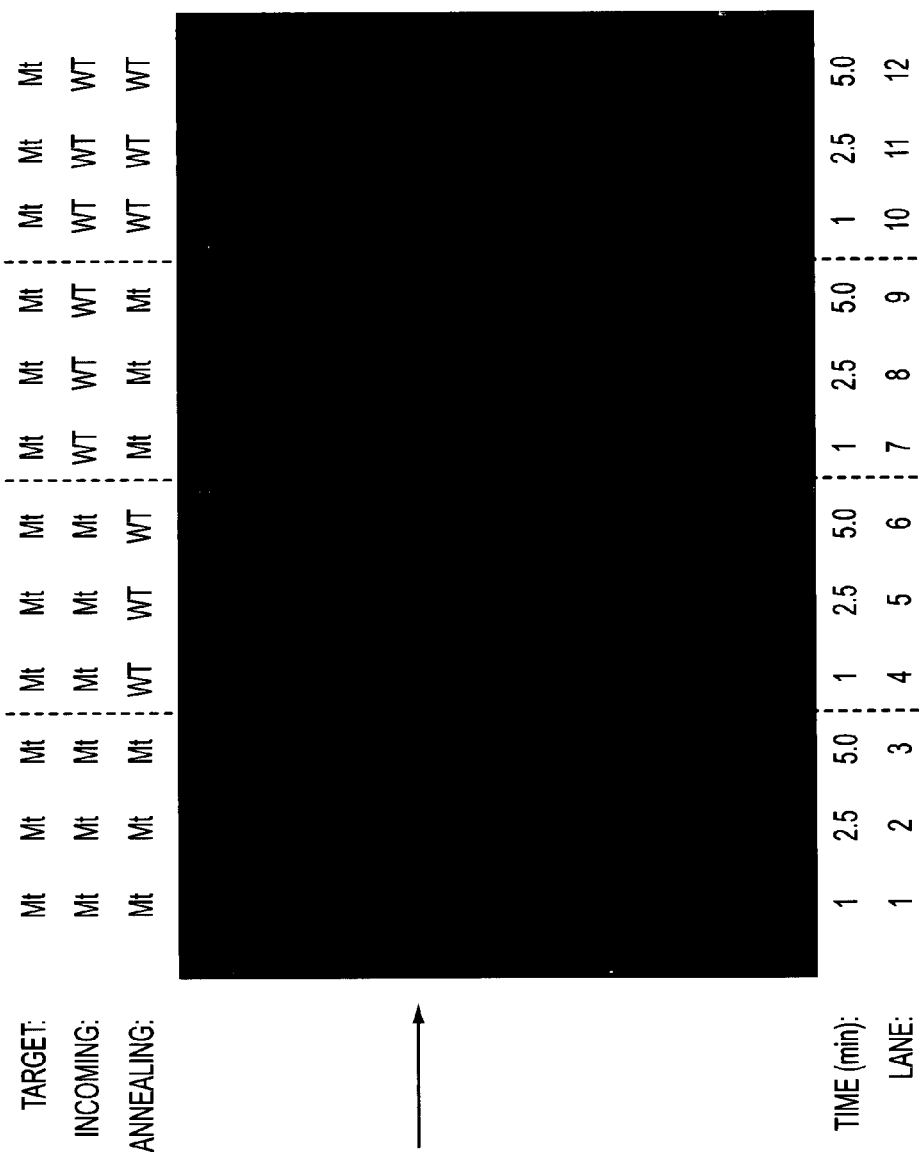
FIG. 21 is a two color fluorescence scan showing single nucleotide mismatch discrimination in a linear target without the presence of competing oligonucleotides, according to embodiments of the present invention.

Results are shown in FIG. 21: times represent duration of incubation at 37° C. following addition of SDS and before chilling.

As can readily be seen, double D loops are seen when both annealing and incoming oligonucleotides are perfectly matched to the target area of the 8 kb linear target.

EXAMPLE 24

Labeling of Annealing Oligonucleotide

In the preceding three examples (Examples 21, 22, and 23), only the incoming oligonucleotides are labeled. In this example, we compare labeling of incoming oligonucleotides with labeling of annealing oligonucleotides using an 8 kb linearized plasmid target. All oligonucleotides are perfectly matched to target.

Materials and Methods
Target:

Linear pAURHyg(rep)eGFP
Incoming Oligonucleotides:
Incoming oligonucleotides are HPLC purified and have the following sequences:
HYG/UD/45G    5'-cgcagctatttacccgcaggacctatc-cacgccctcctacatcga-3' [SEQ ID NO: 64]
HYG/UDF/45G   5'-Cy5-cgcagctatttacccgcaggacctatc-cacgccctcctacatcga-3' [SEQ ID NO: 65]
Annealing Oligonucleotides:
LNA-containing annealing oligonucleotides are used as a crude prep, as synthesized by Proligo. LNA residues are prefixed by "+", deoxyribonucleotides are prefixed by "d".
HYGLNA15T  5'-+G+TdG+G+A+TdA+G+G+TdC+C+T+G+C-3' [SEQ ID NO: 57]
HYG(T)/15GrCB (5'-/Cy5/+G+TdG+G+A+TdA+G+G+TdC+C+T+G+C-/BioTEG/3') [SEQ ID NO: 66]

Results

Figure 22:
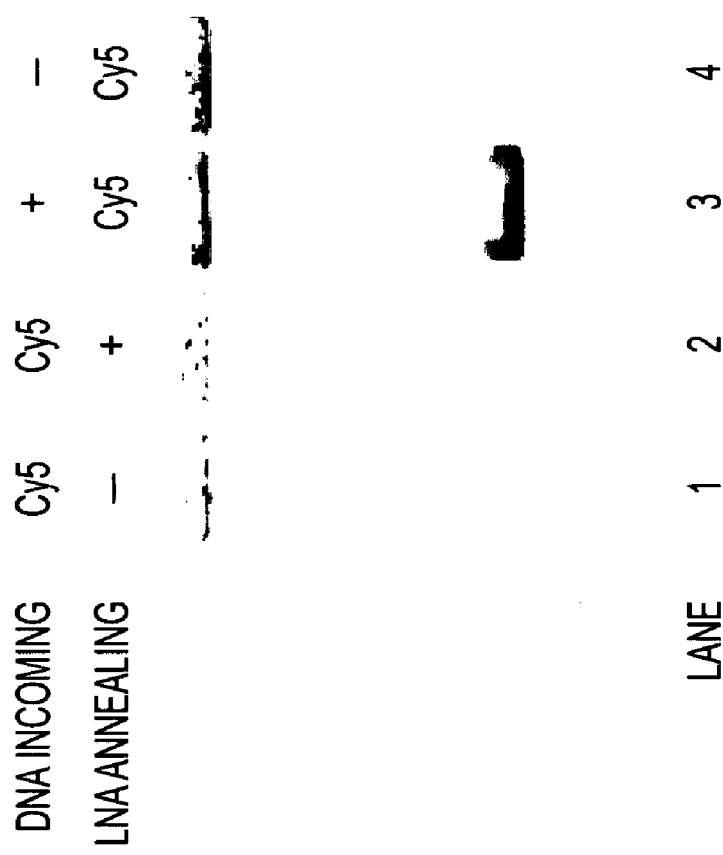
FIG. 22 is a single color fluorescence scan demonstrating that either the incoming or annealing oligonucleotides may be labeled in the methods of the present invention.

FIG. 22 demonstrates that either the incoming or annealing oligo nucleotides may be labeled. Under the indicated conditions, signal is stronger when the annealing oligonucleotide, rather than incoming oligonucleotide, is labeled. Not shown, both may be labeled.

EXAMPLE 25

Temperature Experiments

In this experiment we test for the optimal temperature for forming dDloops in linear duplex DNA.

We use reaction conditions and oligonucleotides as in Example 24 (FIG. 22), except that incubation temperatures are varied. The reactions are incubated for each step of complex formation at 8 temperatures: 22, 27, 32, 37, 45, 50, 55, and 60 degrees Celsius.

The oligonucleotides are Cy5 labeled and unlabeled 45mers as the incoming oligonucleotide, and Cy5 labeled and unlabeled LNA 15mers as the annealing oligonucleotide. The final concentration of the reaction is 7.5 µM RecA, 1 µM incoming Oligo, 1× synaptic comp buffer, 4.7 nM target (linearized pAurHyg(rep)eGFP plasmid), 1.825 µM annealing oligo.

In the first reaction of each temperature, Cy5 labeled incoming is used alone to show the need for the annealing oligo. In the second reaction, Cy5 labeled incoming is used with an unlabelled 15mer LNA. In the third, unlabelled incoming is used with a labeled Cy5 annealing. And in the fourth, the Cy5 labeled annealing is used without an incoming to show the need for the RecA filament.

Figure 23:
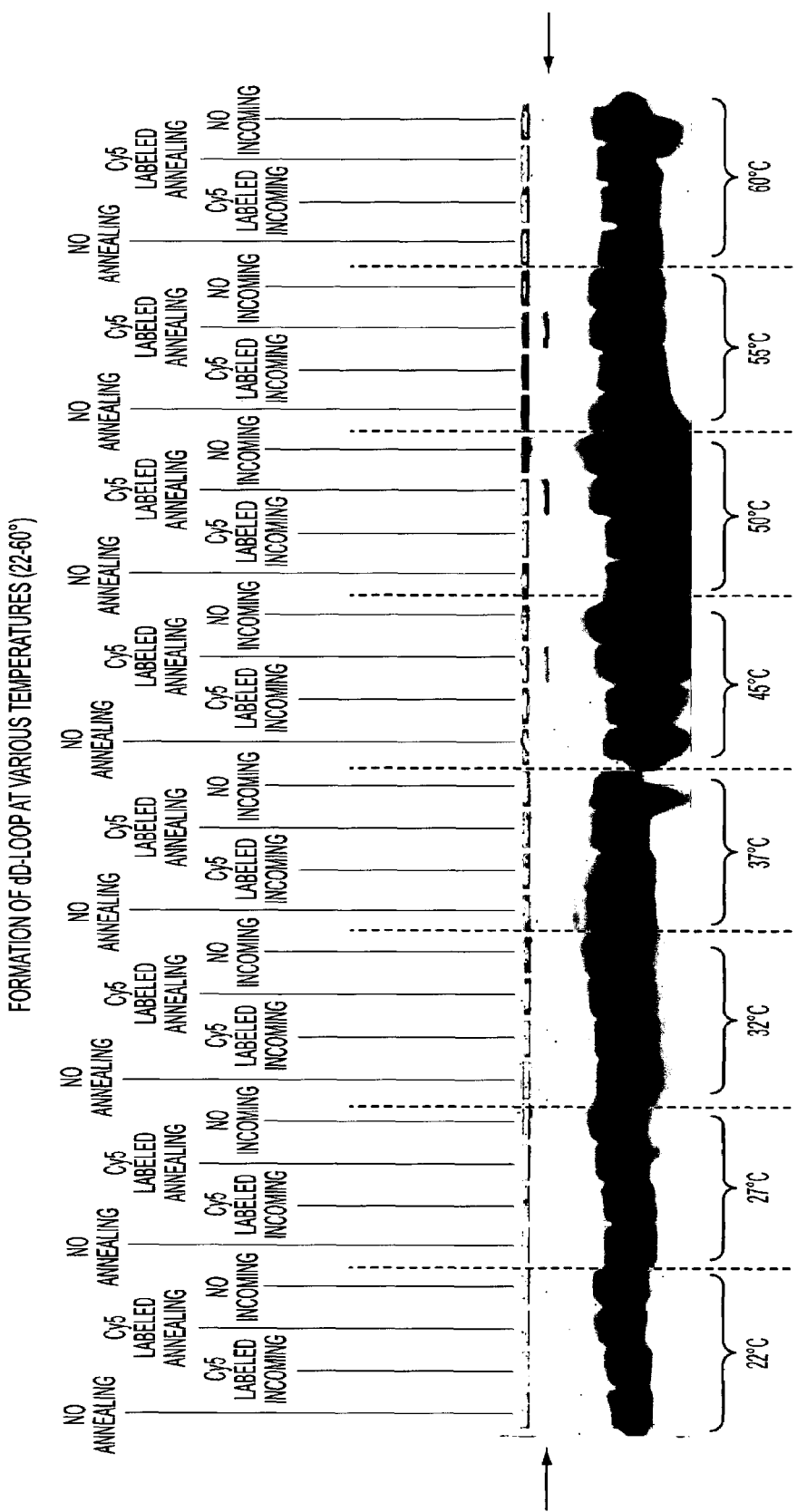
FIG. 23 is a single color fluorescence scan showing that minimal formation of double D-loops (indicated by arrows) is seen with incubations below about 37° C., with optimal formation observed from 50 to about 55° C. using a 45-mer incoming and 15-mer LNA-containing annealing oligonucleotide according to embodiments of the present ivnention.

Results are shown in FIG. 23. As can be seen, minimal formation of double D-loops (indicated by arrows) is seen with incubations below about 37° C., with increasing formation from 37° C. to about 55° C. At 65° C., formation is reduced.

Thus, optimal temperature for double D-loop formation on this target is 50-55° C. using a 45-mer incoming oligonucleotide and 15-mer LNA containing annealing oligonucleotide.

EXAMPLE 26

Mixed Annealing Oligonucleotides

In this experiment, we test the effect of using mixed incoming oligonucleotides—one perfectly matched to the target, one mismatched to target—with mixed annealing oligonucleotides. Label is on the annealing oligonucleotides.

Figure 24:
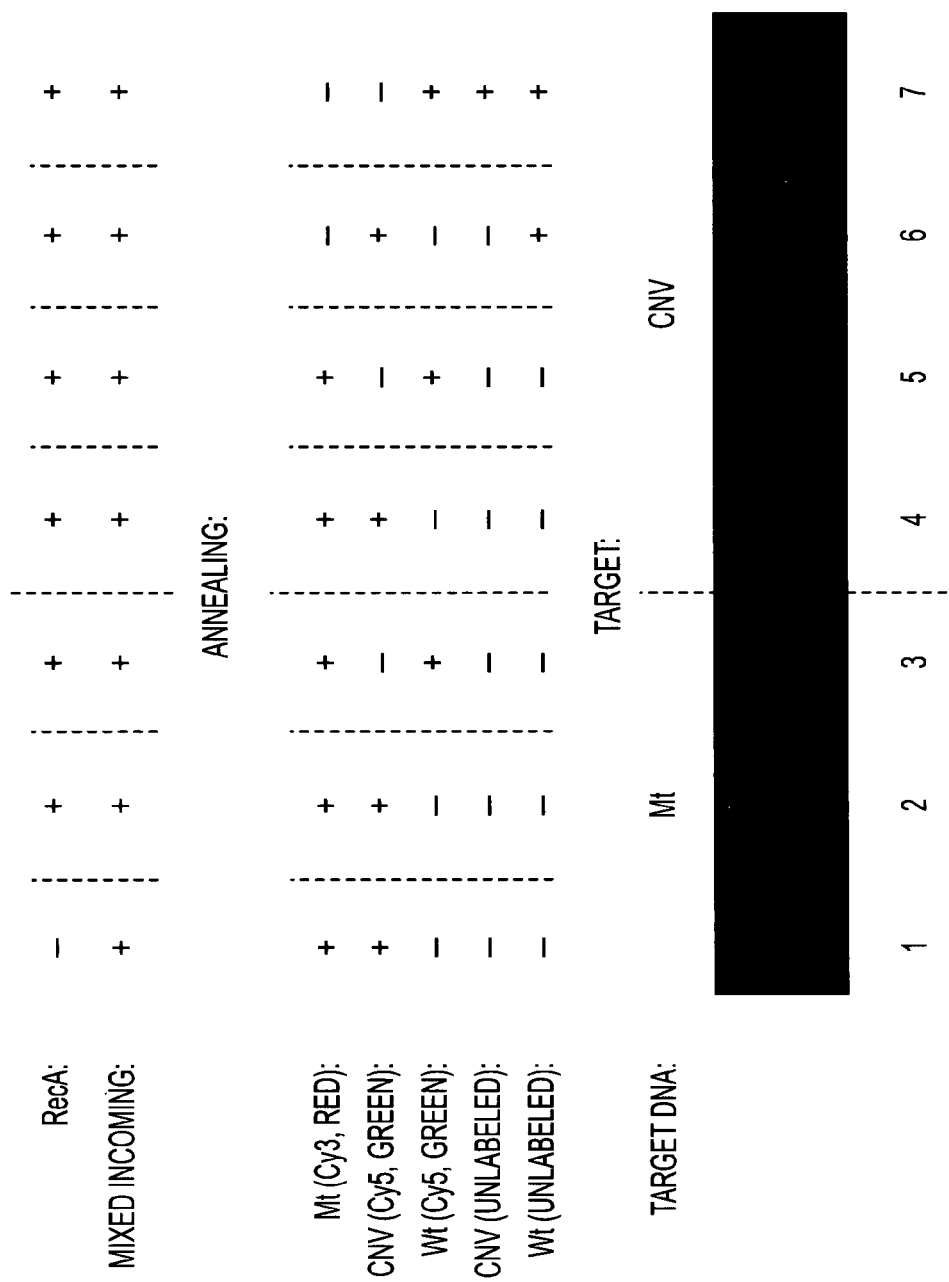
FIG. 24 is a two color fluorescence scan showing mismatch discrimination using competing and distinguishably labeled annealing oligonucleotides, according to embodiments of the present invention.

Results are shown in FIG. 24.

Comparing lanes 2 and 3, addition of a Cy5-labeled mismatched annealing oligonucleotide does not adversely affect the selective formation of a double D-loop at the Mt target. Analogously comparing lanes 6 and 4, addition of the Mt annealing oligonucleotide does not reduce selective formation of a double D-loop at the CNV target.

In fact, we observe that mismatch discrimination directed by mixed labeled annealing oligos is superior to mismatch discrimination using labeled incoming oligos: we get enhanced sensitivity of the assay with reduced background; clean mismatch discrimination is observed regardless of the topology of the DNA target, with linear and supercoiled DNA targets showing clean mismatched discrimination with no mixed signals.

EXAMPLE 27

Length Dependence of Mismatch Discrimination

In this example, experiments are performed to assess the dependence of mismatch discrimination on the length of incoming and annealing oligonucleotides.

In each experiment, 1.1 µl of 18 µM mixed incoming oligonucleotides (exactly matching mutant ("mt") and "converted" ("cnv") targets, which differ by a single nucleotide) and 1 µl of 36.5 µM mixed annealing oligonucleotides (exactly matching mutant and "converted" targets, which differ by a single nucleotide) are used. Incoming oligonucleotides are labeled with Cy3 (mt) and Cy5 (cnv). Annealing oligonucleotides are unlabeled and are composed of 2'0Me residues (indicated by "r" prefix). Sequences are listed below.

About 500 ng of linear 8 kb pAURHygeGFP plasmid and 250 ng of "converted" plasmid is used separately as target DNA.

Reaction conditions for forming double D-loops are essentially as set forth in Example 21, above, with incubations at 37° C.

Sequences

2'-OMe residues are prefixed with "m".

```
Incoming:
23-mers:

HYG(NT)D5Cy5/23C (rep)
5'-Cy5-acccgcaggacctatccacgccc-3'                        [SEQ ID NO: 67]
100 nM
HPLC purification HYG/(NT)D5Cy3/23G(cnv)
5'-Cy3-acccgcaggacgtatccacgccc-3'                        [SEQ ID NO: 68]
100 nM
HPLC purification 27-mers:

HYG(NT)D5Cy5/27C(rep)
5'-Cy5-ttacccgcaggacctatccacgccctc-3'                    [SEQ ID NO: 69]
100 nM
HPLC purification HYG/(NT)D5Cy3/27G(cnv)
5'-Cy3-ttacccgcaggacgtatccacgccctc-3'                    [SEQ ID NO: 70]
100 nM
HPLC purification 35-mers:

HYG(NT)D5Cy5/35C(rep)
5'-Cy5-ctatttacccgcaggacctatccacgccctcctac-3'            [SEQ ID NO: 71]
```

-continued 100 nM
HPLC purification

HYG/(NT)D5Cy3/35G(cnv)
5'-Cy3-ctatttacccgcaggacgtatccacgccctcctac-3'       [SEQ ID NO: 72]
100 nM
HPLC purification 39-mers:

HYG(NT)D5Cy5/39C(rep)
5'-Cy5-agctatttacccgcaggacctatccacgccctcctacat-3'   [SEQ ID NO: 73]
100 nM
HPLC purification HYG/(NT)D5Cy3/39G(cnv)
5'-Cy3-agctatttacccgcaggacgtatccacgccctcctacat-3'   [SEQ ID NO: 74]
100 nM
HPLC purification 43-mers:

HYG(NT)D5Cy5/43C(rep)
5'-Cy5-gcagctatttacccgcaggacctatccacgccctcctacatcg-3'   [SEQ ID NO: 75]
100 nM
HPLC purification HYG/(NT)D5Cy3/43G(cnv)
5'-Cy3-gcagctatttacccgcaggacgtatccacgccctcctacatcg-3'   [SEQ ID NO: 76]
100 nM
HPLC purification Annealing:
9-mers:

HYG(T)R2OMe/9G(rep)
5'-mGmAmUmAmGmGmUmCmC-3'                             [SEQ ID NO: 77]
100 nM
HPLC purification HYG(T)R2OMe/9C(cnv)
5'-mGmAmUmAmCmGmUmCmC                                [SEQ ID NO: 78]
100 nM
HPLC purification 13-mers HYG(T)R2OMe/13G(rep)
5'-mUmGmGmAmUmAmGmGmUmCmCmUmG-3'                     [SEQ ID NO: 79]
100 nM
HPLC purification HYG(T)R2OMe/13C(cnv)
5'-mUmGmGmAmUmAmCmGmUmCmCmUmG-3'                     [SEQ ID NO: 80]
100 nM
HPLC purification 17-mers HYG(T)R2OMe/17G(rep)
5'-mCmGmUmGmGmAmUmAmGmGmUmCmCmUmGmCmG-3'              [SEQ ID NO: 81]
100 nM
HPLC purification HYG(T)R2OMe/17C(cnv)
5'-mCmGmUmGmGmAmUmAmCmGmUmCmCmUmGmCmG-3'              [SEQ ID NO: 82]
100 nM
HPLC purification 21-mers HYG(T)R2OMe/21G(rep)
5'-mGmGmCmGmUmGmGmAmUmAmGmGmUmCmCmUmGmCmGmGmG-3'      [SEQ ID NO: 83]
100 nM
HPLC purification HYG(T)R2OMe/21C(cnv)
5'-mGmGmCmGmUmGmGmAmUmAmCmGmUmCmCmUmGmCmGmGmG-3'      [SEQ ID NO: 84]
100 nM
HPLC purification

```
25-mers

HYG(T)R2OMe/25G(rep)
5'-mAmGmGmGmCmGmUmGmGmAmUmAmGmGmUmCmCmUmGmCmGmGmGmUmA-3'     [SEQ ID NO: 85]
100 nM
HPLC purification HYG(T)R2OMe/25C(cnv)
5'-mAmGmGmGmCmGmUmGmGmAmUmAmCmGmUmCmCmUmGmCmGmGmGmUmA-3'     [SEQ ID NO: 86]
100 nM
HPLC purification
```

Results

Figure 25:
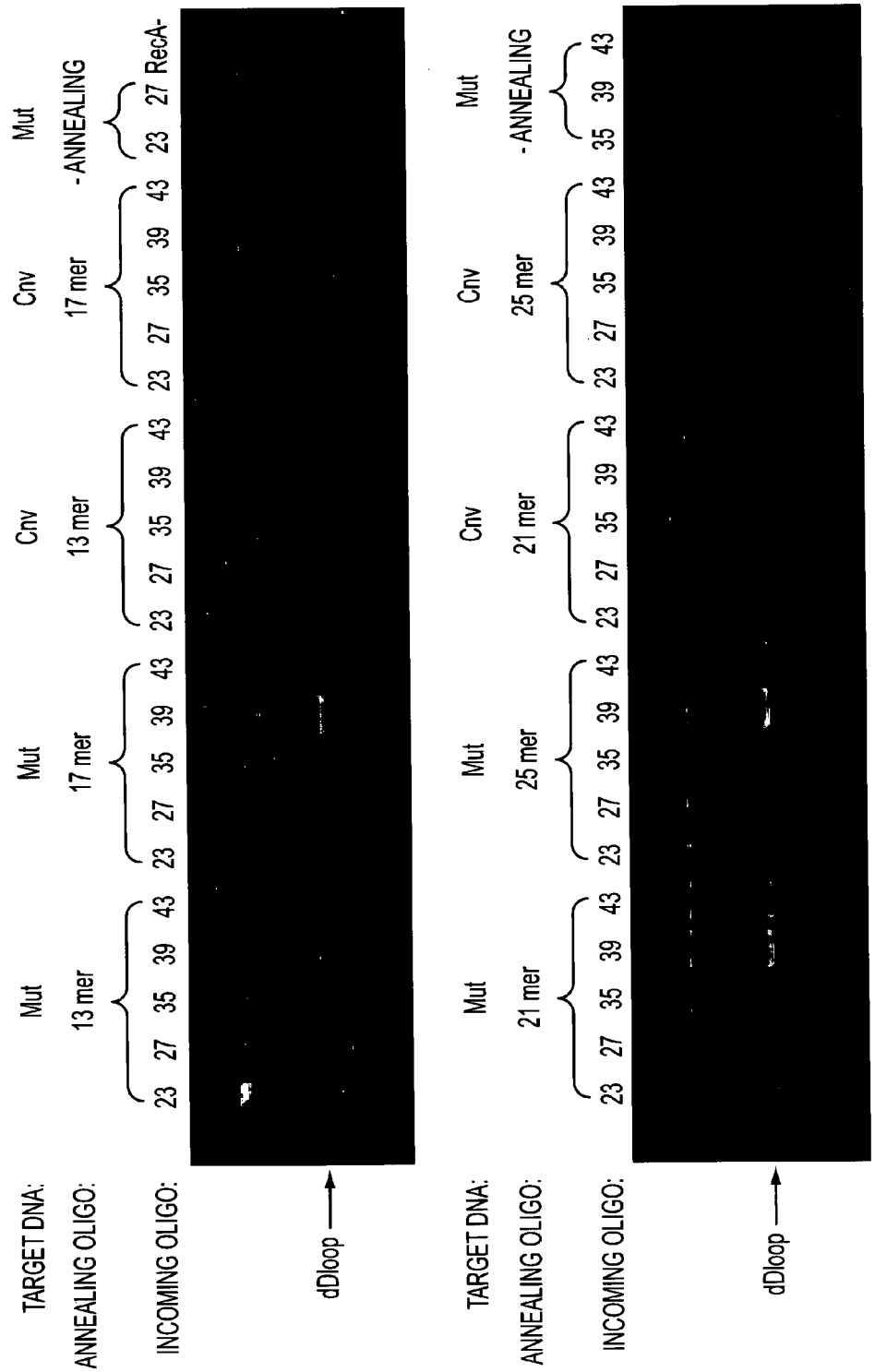
FIG. 25 is a two color fluorescence scan showing the size-dependence of mismatch discrimination according to embodiments of the present invention.

Results are shown in FIG. 25, and demonstrate that the ability to discriminate mismatches is strongly dependent upon the size of both the incoming and annealing oligonucleotides, providing a narrow range for mismatch discrimination.

Under the conditions tested, the annealing oligonucleotide must be more than 13 nt in length to achieve dDloop formation, and can be as large as 25 nt. The incoming oligonucleotide must be at least 23 nt in length and can be as large as 35 nt for precise genotyping, with incoming oligonucleotides of 39 nt or larger giving a mixed signal, losing mismatch fidelity.

Under the conditions tested, a 27-mer incoming oligonucleotide and 17-mer annealing oligonucleotide are optimal, both for yield of double D-loops as well as fidelity of mismatch discrimination.

EXAMPLE 28

Sensitivity

Experiments are performed to determine the target detection sensitivity of the methods.

In a first series of experiments, dDloops are formed on an 8 kb linearized plasmid using $^{32}$P-radiolabeled oligonucleotides. In a second series of experiments, dDloops are formed on the identical target using fluorescently labeled oligonucleotides.

Figure 26:
FIG. 26 is a single color fluorescence scan demonstrating detection of double D-loops down to 1.0 ng of an 8 kb linear target DNA without signal amplification.

FIG. 26 demonstrates that, using a fluorescent label, an 8 kb linear plasmid target can be detected down to 1.0 ng.

Materials and Methods
  Radioactive dDLoop Synthesis
  A 15-minute presynapsis step is performed at 37° C. using 40 nM $^{32}$P-HygUD45G (NT) incoming oligonucleotide and 1.5 μM RecA in a solution containing 1 mM ATPγS, 25 mM Tris-OAc (pH 7.5), 1 mM Mg(OAc)$_2$, and 1 mM DTT. The synapsis phase is begun with the addition of double stranded target and an additional 9 mM Mg(OAc)$_2$ for 5 minutes.

The amount of double stranded target is varied. When using pAURHyg(rep) supercoiled plasmid, the final concentration of the target in solution is 10 nM. Linear pAURHyg (rep) target concentration is 0.73 μg. *Saccharomyces cerevisiae* replacement genomic DNA is 3.65 nM. *Sacharomyces cerevisae* replacement genomic DNA is 7.3 μg/μl. HT1080 human genomic DNA is 7.3 μg/μl.

Double displacement loops (dD-loops) are formed with the addition of required 320 nM $^{32}$P-15mer O-methyl RNA annealing oligonucleotide (to T strand), followed by an additional incubation at 37° C. occurred for 10 minutes. After stopping the reaction in dry ice, the joint molecules are deproteinated by the addition of 1% SDS and associated protein removed by adding KCl (4° C.) to a 100 mM concentration and spinning the solution at 8,000 rpm for 5 min at 4° C.

The presence of joint molecules is confirmed by 1% agarose gel electrophoresis (1× Tris-borate-EDTA, 97 V, 1.5 h). Gels are stained in EtBr for detection of double stranded target before being dried on Whatman DE81 filter paper using a Gel Dryer Vacuum System (FisherBioTech) for 2.5 h at 80° C. and visualized by using a Typhoon 8600 PhosphorImager (Molecular Dynamics Inc., California).

Quantification of joint complexes is done using ImageQuant 5.2 software.

EXAMPLE 29

Detection of PCR Product

This Example demonstrates sequence-specific detection of a clinically relevant gene target present within a PCR amplification product. The PCR product is purified from the amplification template.

The Example further demonstrates the ability to detect double D loops formed using oligonucleotides that have biotin as capture moiety.

Target and Oligonucleotides

```
Wildtype β-tubulin sequence:
CCCGCCCCGCGGCCTGAAGATGTCGGCCACCTTCATCGGCAACAGCACGGC           [SEQ ID NO: 87]

βTUBwt/31D/5'Bio (incoming oligonucleotide) (has 5'
biotin
5'-GGCCTGAAGATGTCGGCCACCTTCATCGGCA-3'                         [SEQ ID NO: 88]

βTUBwt/15L/5Cy5 (annealing oligonucleotide) (LNA)
5'-AAGGTGGCCGACATC-3'                                          [SEQ ID NO: 89]
```

Results

Figure 27A:
FIGS. 27A and 27B show detection of human beta tubulin PCR product using double D-loop formation.
Figure 27B:
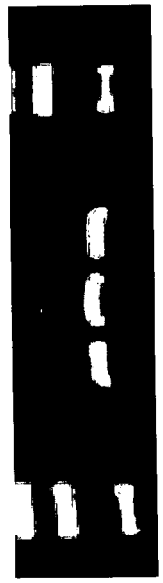

Results are shown in FIGS. 27A and 27B.

FIG. 27A shows that double D loops are detectable in the PCR product only when RecA and both incoming and annealing oligonucleotides are present. FIG. 27B is the same gel, post-stained with ethidium bromide, showing approximately equal amounts of target in each reaction.

EXAMPLE 30

Context Independence of Detection

Specific alleles of genes relevant to human disease are discriminably detected in PCR amplification products using identical conditions, indicating that allelic discrimination is possible independently of the genomic context of the polymorphism. The genes are k-RAS, p53, and beta globin. Annealing oligonucleotides with PNA (designated by/P in the oligonucleotide name) and LNA (designated by/L in the oligonucleotide name) are each used effectively.

The oligonucleotides used are the following:

```
P53cd241wt/D/Cy5
5'-/5Cy5/atgccgcccatgcaggaactgttacacatgt/3BioTEG/-3'      [SEQ ID NO: 90]

P53cd241mt/D/Cy3
5'-/5Cy3/atgccgcccatgcagaaactgttacacatgt/3BioTEG/-3'      [SEQ ID NO: 91]

P53cd241wt/P
5'-aacagttcctgcatg-3'                                      [SEQ ID NO: 92]

P53cd241mt/P
5'-aacagtttctgcatg-3'                                      [SEQ ID NO: 93]

P53cd241wt/L
5'-aacagttcctgcatg-3'                                      [SEQ ID NO: 94]

P53cd241mt/L
5'-aacagtttctgcatg-3'                                      [SEQ ID NO: 95]

K-ras separation/diagnostic oligos

Krascd13wt/D/Cy5
5'-/5Cy5/ggcactcttgcctacgccaccagctccaact/3BioTEG/-3'       [SEQ ID NO: 96]

Krascd13mt/D/Cy3
5'-/5Cy3/ggcactcttgcctacgtcaccagctccaact/3BioTEG/-3'       [SEQ ID NO: 97]

Krascd13wt/P
5'-gctggtggcgtaggc-3'                                      [SEQ ID NO: 98]

Krascd13mt/P
5'-gctggtgacgtaggc-3'                                      [SEQ ID NO: 99]

Krascd13wt/L
5'-gctggtggcgtaggc-3'                                      [SEQ ID NO: 100]

Krascd13mt/L
5'-gctggtgacgtaggc-3'                                      [SEQ ID NO: 101]

β Globin separation/diagnostic oligos

BGloA/D/Cy5
5'-/5cy5/acggcagacttctcctcaggagtcaggtgca/3BioTEG/-3'       [SEQ ID NO: 102]

BGloS/D/Cy3
5'-/5Cy/acggcagacttctccacaggagtcaggtgca/3BioTEG/-3'        [SEQ ID NO: 103]

BGloAwt/P
5'-actcctgaggagaag-3'                                      [SEQ ID NO: 104]

BGloSmt/P
5'-actcctgtggagaag-3'                                      [SEQ ID NO: 105]

BGloAwt/L
5'-actcctgaggagaag-3'                                      [SEQ ID NO: 106]

BGloSmt/L
5'-actcctgtggagaag-3'                                      [SEQ ID NO: 107]
```

EXAMPLE 31

Gene-Specific Separation and Purification

Experiments are performed to assess the ability to separate and purify plasmid targets from inhomogeneous mixture. Results are tabulated in FIG. 28.

Two unrelated plasmids—one resistant to kanamycin ("Kan"), one resistant to tetracycline ("tet")—are mixed in the ratios shown in the first column of FIG. 28.

Aliquots of each plasmid mixture are separately transformed into competent *E. coli* and aliquots of each pool of transformed bacteria plated on media containing either kanamycin or tetracyline, and resulting colonies counted. Results are enumerated in columns 2 and 3 ("Colonies (PreSep)").

Another aliquot of each plasmid mixture is relaxed using topoisomerase I. (In other experiments, not shown, T4 Gene 2 is used to relax the plasmid targets with similar results.) The mixture of relaxed closed circular plasmids are then subjected to double D-loop based separation and purification using a 31-mer incoming oligonucleotide biotinylated at its 3' terminus and a 20-mer PNA annealing oligonucleotide, both specific for a portion of the kanamycin resistance gene. The post-separation mixture is transformed into *E. coli*, and aliquots plated on media containing either kanamycin or tetracycline. Results are enumerated in columns 4 and 5 ("Colonies (PostSep)").

Oligonucleotide sequences are set forth below. The separation protocols are similar to those used in Example 15, with differences highlighted below.

```
Incoming DNA Oligo:

KAN/LDB/31t                            [SEQ ID NO: 108]
5'-gaggctattcggctatgactgggcacaacag/3BioTEG/-3'
100 nM
HPLC purification Annealing PNA Oligo:

KAN/LP/20A                             [SEQ ID NO: 109]
Ac-gtgcccagtcatagccgaat
```

Separation Protocol:
1. Preform DNA oligonucleotide RecA filament.
Mix:

| Incoming oligo (18 uM) | 2.2 ul |
| 10X Syn Complete Buffer | 4.0 ul |
| RecA (125.5 uM) | 4.0 ul |
| H$_2$O | 23.8 ul |

Incubate 37° C., 10 min
Add:
   2 µl topoisomerase I relaxed plasmid mixture (250 ng/µl)
Incubate 37° C., 20 min
2. Add: PNA Annealing oligo kan/LP/20A (36.2 µM)
Incubate 37° C., 2 min
3. Stop with 2 µl SDS (10%)
Incubate RT, 1 min
4. Add: 4 µl 1M KCl, spin 5 min 4C @ 8 k rpm.
5. Add: 10 µl prepared Dynabeads 280.
To prepare beads:
   a) Gently resuspend beads, add to 1.5 ml microfuge tube (10 ul/rxn).
   b) Place tubes on magnet 1 min, remove supernatant.
   c) Remove tube from magnet, resuspend in 1× Syn buffer.
   d) Place tubes on magnet 1 min, remove supernatant.
   e) Repeat steps "c" and "d" 2-3 times.
6. Incubate reaction in microfuge tube @ 4° C. for 1 hr with rotation.
7. Separate on magnet @ 4° C., 1 min, remove supernatant.
8. Wash 2-3 times with 50 µl 1× Syn Buffer.
   (Resuspend, place on magnet 1 min, take off supernatant, repeat)
9. Elute bound plasmid from bead by adding 20 ul H$_2$O and heating to 65° C. 15 min
10. Electroporate 5 µl into DH10B cells and plate aliquots separately on kanamycin-containing and tetracycline-containing media Results As can be seen from columns 4 and 5 of the table set forth in FIG. 28, biotinylated double D-loops formed using a 31-mer incoming oligonucleotide biotinylated at its 3' terminus and a 20-mer PNA annealing oligonucleotide, both specific for a portion of the kanamycin resistance gene, allow separation and purification of kan-resistant plasmids from an inhomogeneous mixture. Kan$^+$ plasmids can be isolated, free from tet$^+$ contamination, even when present at an initial molar ratio of 1:10$^5$ (kan$^+$/tet$^+$). Additional experiments (not shown) demonstrate isolation without contamination even when the initial molar ratio is 1:10$^6$. The data further demonstrate that purification is effected without destroying the ability of the plasmids to replicate.

EXAMPLE 32

Allele-Specific Separation and Purification

In this experiment, five different related plasmid targets are used, as shown in column 1 of the table set forth in FIG. 29.

pKAN$^+$ is a kanamycin-resistant plasmid having the wild-type kanamycin resistance gene.

pKAN$^-$ is identical to pKAN$^+$ except for a point mutation that converts the wild-type codon "tat" to "tag", inactivating the kanamycin resistance gene.

Each of CNV B1, CNV D3, and CNV D5 is a pool of plasmids in which the mutant "tag" has been targeted, in three separate experiments, for alteration to "tac". "TAC" at the relevant codon restores the wild-type phenotype (kanamycin resistance), but with a detectably altered genotype ("tac" rather than "tat"). Targeted alteration is performed using modified oligonucleotides according to procedures set forth in U.S. patent application Ser. No. 09/818,875, filed Mar. 27, 2001, and in WO 01/73002, the disclosures of which are incorporated herein by reference in their entireties.

All plasmids are ampicillin resistant.

Column 2 shows the percentage of "tac"-containing ("Kan CNV") plasmids within each sample, as determined using the Applied Biosystems SnaPshot™ primer extension genotyping system.

As expected, neither the pure wild type pKAN$^+$ nor the pure pKAN$^-$ samples contains any plasmids with the "converted" tac codon. In contrast, each of the pools targeted for gene alteration contains converted plasmids, with pool B1 having 5%, pool D3 having 69%, and pool D5 having 10% "tac" (Kan CNV) plasmids, as reported by the SnaPshot system.

As an independent measure of the percentage of Kan$^+$ plasmids, an aliquot of each sample is transformed into *E. coli* and aliquots of the transformed bacteria plated separately on kanamycin-containing and ampicillin-containing media, with results as shown in columns 3, 4 and 5 ("Colonies (presep)").

As expected, nearly all plasmids in the pKAN⁺ sample are kan$^R$; conversely, no kan$^R$ plasmids are seen among pKAN⁻ transformants. Among the gene-altered pools of plasmids, the percentage kan$^R$ plasmids is similar but nonidentical to the percentages suggested by SnaPshot™ genotyping.

An aliquot of each of the five samples is then subjected to double D-loop based separation and purification of "tac"-containing plasmids, using incoming and annealing oligonucleotides that are perfectly complementary to the "tac"-containing target region.

Results shown in columns 6, 7 and 8 show that purification of tetR plasmids is effected in the PKAN⁺ and all three pools of converted plasmids, but not from the pKAN⁻ sample. The presence of kanR plasmids in the aliquot purified from the pKAN⁺ sample demonstrate that the double D-loops form in this supercoiled plasmid without perfect discrimination between the wild-type "tat" sequence and converted "tac" sequence.

Column 9 gives summary percentages from an experiment in which the plasmids are relaxed prior to separation. In contrast to the results with supercoiled plasmids, no kan$^R$ plasmids are isolated from the pKAN⁺ wild type ("tat") sample. And >90% of plasmids obtained from the gene-altered pools of plasmids (B1, D3, and D5) are kan$^R$.

EXAMPLE 33

Single Nucleotide Discrimination in a YAC Target

In this Example, we test the ability to discriminate single nucleotide polymorphisms in human genomic DNA inserts within yeast artificial chromosomes (YACs).

We use two yeast strains (AB1380), each containing a 248 kb YAC. The YACs contain human beta-globin genomic DNA, differing in the β globin allele: one has the wild-type β globin allele ($β^A$), the other the sickle cell mutation ($β^S$) (Peterson et. al., Proc. Natl. Acad. Sci. USA (1993)).

We extract genomic DNA, including the YAC DNA, separately from each strain. We then form double D-loops in parallel reactions using essentially the same conditions as described in Example 17. We use either BGloAWT/5'BioTEG/31 or BGloAWT/5'Cy3/2OMe as the incoming oligonucleotide, and either BGloAWT/5'Cy3/2OMe, BGloAWT/2OMe, BGloAWT/L, or BGloAWT/P, as the annealing oligo. Following double D-loop formation and deproteinization, we run the products on a 1% agarose gel and quantify the amount of double D-loop formed using Molecular Dynamics ImageQuant™ and a Typhoon™ imager.

Incoming Oligonucleotides:

BGloAWT/5' BioTEG/31
(5'-/5BioTEG/ACGGCAGACTTCTCCTCAGGAGTCAGGTGCA-3')
[SEQ ID NO: 110]

BGloAWT/5' Cy5/31
(5'-/5Cy5/ACGGCAGACTTCTCCTCAGGAGTCAGGTGCA-3')
[SEQ ID NO: 111]
Annealing Oligonucleotides:

BGloAWT/5' Cy3/2OMe
(5'-/5Cy3/mAmCmUmCmCmUmGmAmGmGmAmGmAmAmG-3')
[SEQ ID NO: 112]

BGloAWT/2OMe
(5'-/5Cy3/mAmCmUmCmCmUmGmAmGmGmAmGmAmAmG-3')
[SEQ ID NO: 113]

The above two annealing oligonucleotides include 2'-OMe residues, indicated by the prefix "m".

BGloAWT/L
(5'-+A+C+T+C+C+T+G+A+G+G+A+G+A+A+G-3')
[SEQ ID NO: 106]

This annealing oligonucleotide includes LNA residues, indicated by the prefix "+".

BGloAWT/P
(Ac-ACTCCTGAGGAGAAG)
[SEQ ID NO: 104]

This annealing oligonucleotide is entirely composed of PNA residues; an acetylated terminus is indicated.

Results

We find that we can discriminably detect a single nucleotide polymorphism in a clinically relevant human gene within the context of a complex eukaryotic genome ($2.8 \times 10^7$ bp per diploid genome).

EXAMPLE 34

Concurrent Fluorescence Detection

Figure 30:
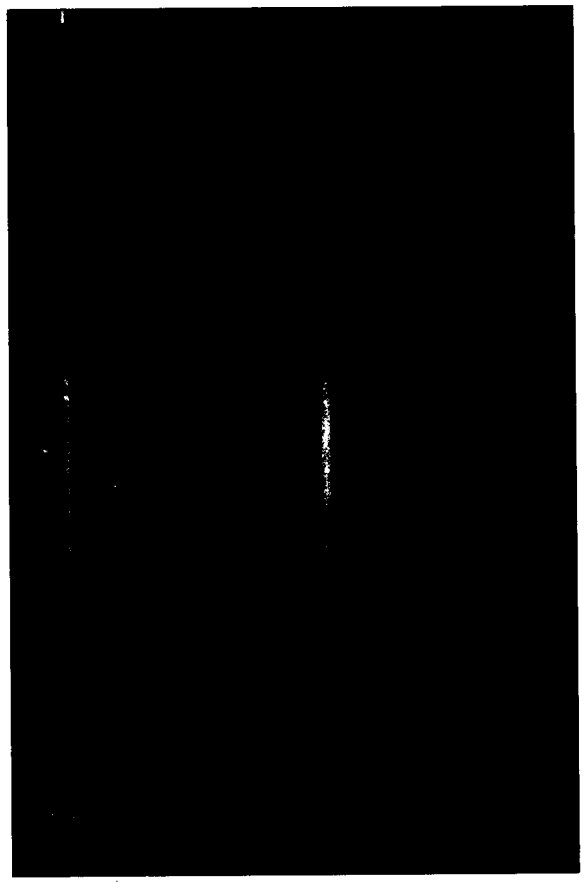
FIG. 30 is a two color fluorescence scan of double D-loops formed with oligonucleotides labeled as shown.

Labeling incoming oligonucleotide with one fluorophore and annealing oligonucleotide with another, we demonstrate that we can separately detect the presence of each discriminably labeled oligonucleotide present within a double D-loop (red and green) and that we can concurrently detect the presence of both oligonucleotides within a double D-loop (yellow). Results are shown in FIG. 30. Not shown, fluorophores separately present on the incoming and annealing oligonucleotide are capable of participating in fluorescence resonance energy transfer.

Target
Linear pAUR 123 hyg (REP)
Incoming Oligonucleotide
  31-mer with cy5 label "hyg" (sequence provided in other examples)
  31-mer hyg with no label (sequence as above)
Annealing Oligonucleotide
  15mer hyg all 2'-OMe methyl with Cy 3 label 5'-/5Cy3/mGmUmGmGmAmUmAmGmGmUmCmC-mUmGmC-3'] [SEQ ID NO: 114]
  15mer hyg all 2'-OMe methyl with Cy 3 label
Conditions:
1. 2 µl 10× buffer
2. 1.11 µl incoming
3. 2 µl recA
   (approximately 70 uM, as previously described in other examples)
4. 12.89 µl dH20
5. Incubate 10 min @ 50° C.
6. 1 µl linearized pAur 123 hyg (REP)
   (where 1.88 µl is 500 ng)
7. Incubate 10 min @ 50° C.
8. 1 µl annealing
9. Incubate 10 min @ 50° C.
10. Freeze, add 2 µl 10% SDS, 8 µl 25% Ficoll
11. Run 1% agarose gel 3.5 hr
FIG. 30 Lanes
  Lane 1: no annealing, labeled cy5 31mer incoming
  Lane 2: labeled cy5 31mer incoming, unlabeled 2'omethyl 15mer annealing
  Lane 3: labeled cy5 31mer incoming, labeled cy3 2'omethyl 15mer annealing Lane 4: unlabeled cy5 31mer incoming, labeled cy3 2' omethyl 15mer annealing
Lane 5: no incoming, labeled cy 3 2'omethyl 15 mer

EXAMPLE 35

Single Nucleotide Polymorphism Detection in Human Genomic DNA

Using genomic DNA prepared from cultured cells as target, we demonstrate that we can discriminate a single base pair change in a Hyg target integrated into human genomic DNA.

All patents, patent publications, and other published references mentioned herein are hereby incorporated by reference in their entireties as if each had been individually and specifically incorporated by reference herein.

Although illustrative embodiments of the present invention are described above, it will be evident to one skilled in the art that various changes and modifications may be made without departing from the spirit and scope of the invention. Many examples of such modifications have been given through the foregoing specification. It is intended that the appended claims cover all such changes and modifications that fall within the true spirit and scope of the invention.

What is claimed is:

1. A method of distinguishing the presence of a nonsupercoiled target nucleic acid from the presence of nonsupercoiled target variants within a sample of nucleic acids having a common target query region, the method comprising:
providing a first oligonucleotide and a second oligonucleotide, wherein said first oligonucleotides is bound by a recombinase and said second oligonucleotide is free of a recombinase;
adding said first oligonucleotide to the sample to form a mixture;
adding said second oligonucleotide to the mixture to form a double D loop;
deproteinizing the double D loop; and
distinguishing the double D loops that are stable to deproteinization, wherein the presence of a stable double D loop distinguishes the presence of target from that of variants;
wherein the first oligonucleotide comprises a complementarity region that is perfectly complementary to a first strand of the target across the entirety of the target query region and wherein the second oligonucleotide includes a complementarity region that is perfectly complementary in sequence to a second strand of the target across at least a portion of the target query region, and at least one of said first or second oligonucleotide complementarity regions is imperfectly complementary to at least one of a first strand or a second strand of the query region of the target variants.

2. The method of claim 1, wherein said second oligonucleotide comprises base modifications.

3. The method of claim 1, further comprising the antecedent step of binding a recombinase to said first oligonucleotide.

4. The method of claim 3, wherein said recombinase is *E. coli* RecA or a mutant thereof.

5. The method of claim 1, wherein said first oligonucleotide complementarity region is no more than 100 nucleotides in length.

6. The method of claim 5, wherein said first oligonucleotide complementarity region is no more than 50 nucleotides in length.

7. The method of claim 1, wherein said first oligonucleotide is no more than 100 nucleotides in length.

8. The method of claim 7, wherein said first oligonucleotide is no more than 50 nucleotides in length.

9. The method of claim 2, wherein said second oligonucleotide comprises base modifications selected from the group consisting of: LNA bases, PNA bases, RNA bases, and 2'-OMe bases.

10. The method of claim 9, wherein said second oligonucleotide includes at least 30% modified bases.

11. The method of claim 10, wherein said second oligonucleotide includes at least 50% modified bases.

12. The method of claim 11, wherein said second oligonucleotide includes at least 75% modified bases.

13. The method of claim 1, wherein said second oligonucleotide complementarity region is no more than 50 nucleotides in length.

14. The method of claim 13, wherein said second oligonucleotide complementarity region is no more than 25 nucleotides in length.

15. The method of claim 14, wherein said second oligonucleotide complementarity region is no more than 16 nucleotides in length.

16. The method of claim 1, wherein said second oligonucleotide is no more than 50 nucleotides in length.

17. The method of claim 16, wherein said second oligonucleotide is no more than 25 nucleotides in length.

18. The method of claim 17, wherein said second oligonucleotide is no more than 20 nucleotides in length.

19. The method of claim 1, wherein said first and second oligonucleotide complementarity regions overlap by no more than 25 nucleotides.

20. The method of claim 19, wherein said first and second oligonucleotide complementarity regions overlap by no more than 15 nucleotides.

21. The method of claim 1, wherein at least one of the first and second oligonucleotides includes at least one detectable label.

22. The method of claim 21, wherein said at least one label is selected from the group consisting of: a radionuclide, a fluorophore, a fluorescence resonance energy transfer tandem fluorophore, a fluorescence resonance energy transfer donor, a fluorescence resonance energy transfer acceptor, a mass tag, an enzyme, a genotypic label, or a hapten.

23. The method of claim 22, wherein said at least one label is a fluorophore.

24. The method of claim 22, wherein said at least one label is a genotypic label.

25. The method of claim 1, wherein said formation of a double D loop is performed at a temperature of at least 37° C.

26. The method of claim 25, wherein said formation of a double D loop is performed at a temperature of at least 45° C.

27. The method of claim 26, wherein said formation of a double D loop is performed at a temperature of at least 50° C.

28. The method of claim 27, wherein said formation of a double D loop at a temperature of at least 55° C.

29. The method of claim 1, wherein the deproteinizing step is performed at a temperature of at least 37° C.

30. The method of claim 29, wherein said deproteinizing step is performed for no more than about 10 minutes.

31. The method of claim 1, wherein said double D loops are stable for a time following deproteinization sufficient to permit detectable separation of said target from said variants.

32. The method of claim 31, wherein said separation is electrophoretic separation.

33. The method of claim 1, wherein said double D loops are stable for at least 2 hours at 4° C. following deproteinization.

34. The method of claim 33, wherein said double D loops are stable for at least 4 hours at 4° C. following deproteinization.

35. The method of claim 1, wherein said double D loops are stable for at least 30 minutes at 37° C. following deproteinization.

36. The method of claim 1, wherein said nonsupercoiled double-stranded target is linear duplex DNA.

37. The method of claim 1, wherein said nonsupercoiled double-stranded target is a covalently closed circle.

38. The method of claim 1, wherein said nonsupercoiled double-stranded target is an artificial chromosome.

39. The method of claim 38, wherein the target query region within said artificial chromosome is flanked by recognition sites for a site-specific recombinase.

40. The method of claim 1, wherein the nucleic acids of said sample are pooled from a plurality of individuals.

41. The method of claim 1, wherein the nucleic acids of said sample are from a single individual.

42. The method of claim 1, wherein said nucleic acid sample includes at least one variant that differs from said target by no more than one nucleotide in said query region.

43. The method of claim 40, wherein said nucleic acid sample includes at least one variant that differs from said target by no more than one nucleotide in the target query region.

44. The method of claim 43, wherein said at least one variant is a naturally-occurring variant of said target.

45. The method of claim 42, wherein said at least one variant is a recombinantly-engineered variant of said target.

46. The method of claim 25, further comprising the step, after deproteinizing and before distinguishing said double D loops, of separating the nucleic acids that have double D loops from nucleic acids lacking double D loops.

47. The method of claim 46, wherein at least one of said first and second oligonucleotides includes a capture moiety.

48. The method of claim 47, wherein said capture moiety is biotin.

49. The method of claim 1, further comprising the step, after double D loop formation, of extending by polymerase either or both of the first or second oligonucleotides.

50. The method of claim 49, wherein said extension is a single base extension.

51. The method of claim 49, wherein said extension amplifies at least a portion of the target region.

52. The method of claim 51, wherein said amplification is isothermal.

53. The method of claim 1, further comprising the step of quantifying the absolute or relative abundance of target.

54. A method of distinguishably detecting the presence of a plurality of nonsupercoiled targets within a sample of nucleic acids, the method comprising:
for each of the plurality of targets desired to be detected, providing a first oligonucleotide and a second oligonucleotide, wherein said first oligonucleotide is bound by a recombinase and said second oligonucleotide is free of a recombinase;
wherein said first oligonucleotide includes a complementarity region that is perfectly complementary in sequence to a first strand of its respective target across the entirety of the target query region, and said second oligonucleotide includes a complementarity region that is perfectly complementary in sequence to a second strand of the same target across at least a portion of the target query region and at least one of said oligonucleotide regions is imperfectly complementary in sequence to respective first and second strands of the query region of each of the other targets desired discriminably to be detected;
adding said first oligonucleotide to the sample to form a mixture;
adding said second oligonucleotide to the mixture to form a double D loop;
deproteinizing the double D loop to form at least one deproteinization-stable double D loop; and
distinguishably detecting at least one deproteinization-stable double D loop formed in the target query region, each target double D loop being distinguishably detectable from all others of the double D loops formed in said sample.

55. The method of claim 54, wherein said second oligonucleotide comprises base modifications, and wherein at least one of said oligonucleotides is distinguishable from the first and second oligonucleotides used to detect each of the others of the plurality of targets desired to be detected.

56. The method of claim 54, further comprising quantifying the relative abundance of each of said targets.

57. The method of claim 54, wherein at least 10 targets are discriminably detected.

58. The method of claim 57, wherein at least 50 targets are discriminably detected.

59. The method of claim 58, wherein at least 100 targets are discriminably detected.

60. The method of claim 54, wherein said plurality of targets are discriminably detected concurrently.

61. The method of claim 60, wherein said targets are detected by microarray hybridization.

62. A method of separating a nonsupercoiled double stranded nucleic acid target from other nonsupercoiled nucleic acids present within a sample of nucleic acids, the method comprising:

providing a first oligonucleotide and a second oligonucleotide, wherein said first oligonucleotide is bound by a recombinase and said second oligonucleotides is free of a recombinase;

wherein said first oligonucleotide includes a complementarity region that is perfectly complementary in sequence to a first strand of the target across the entirety of the target query region, and said second oligonucleotide includes a complementarity region that is perfectly complementary in sequence to a second strand of the target across at least a portion of the target query region, and at least one of said first or second oligonucleotide complementarity regions is imperfectly complementary to the respective first and second strands of the query region of each of said other nonsupercoiled nucleic acids;

adding said first oligonucleotide to the sample to form a mixture;

adding said second oligonucleotide to the mixture to form a double D loop;

deproteinizing the double D loop to form at least one deproteinization-stable double D loop; and separating nucleic acids having at least one deproteinization-stable double D loop in the query region of the target, from other nucleic acids present within said sample.

63. The method of claim 62, wherein said second oligonucleotide comprises base modifications.

64. The method of claim 62, wherein at least one of the first and second oligonucleotides includes a capture moiety, and said nucleic acids having deproteinization-stable double D loops are separated from other nucleic acids present within said sample by capture of said moiety.

65. The method of claim 64, wherein said moiety is captured to a solid substrate.

66. The method of claim 65, wherein said solid substrate is a surface of a bead.

67. A method of distinguishing the presence of a supercoiled target nucleic acid from the presence of supercoiled target variants within a sample of nucleic acids, the variants differing from the target by as few as one nucleotide within a common target query region, the method comprising:

providing a first oligonucleotide and a second oligonucleotide, wherein said first oligonucleotide is bound by a recombinase and wherein said second oligonucleotide is free of a recombinase;

wherein the first oligonucleotide includes a complementarity region that is perfectly complementary in sequence to a first strand of the target across the entirety of the target query region, said region being imperfectly complementary to a first strand of the query region of each of said target variants, wherein the first oligonucleotide mediates formation of at least one deproteinization-stable double D loop in the query region of the target;

wherein said second oligonucleotide includes a complementarity region that is perfectly complementary in sequence to a second strand of the target across at least a portion of the target query region;

adding said first oligonucleotide to the sample to form a mixture;

adding said second oligonucleotide to the mixture to form a double D loop;

deproteinizing the double D loop; and distinguishing the double D loops that are stable to deproteinization, wherein the presence of a stable double D loop distinguishes the presence of target from that of variants.

68. The method of 67, wherein at least one of said first and second oligonucleotide complementarity regions is imperfectly complementary to respective strand of the query region of each of said target variants, and wherein said second oligonucleotide comprises base modifications and wherein said second oligonucleotide is distinguishably detectable.

69. The method of claim 68, further comprising:

providing a third oligonucleotide, wherein said third oligonucleotide is free of a recombinase and comprises base modifications;

adding said third oligonucleotide to the double D loop;

wherein said third oligonucleotide includes a complementarity region that is perfectly complementary in sequence to at least a portion of the second strand of the query region of a target variant as to which the target is desired to be discriminated, and wherein said third oligonucleotide complementary region is imperfectly complementary in sequence to the complementarity region of said first oligonucleotide.

* * * * *

SEQUENCE LISTING

```
<160> NUMBER OF SEQ ID NOS: 115

<210> SEQ ID NO 1
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctccggccgc ttgggtggag aggctattcg gctacgactg ggcacaacag acaatcggct      60
gctctgatgc                                                             70

<210> SEQ ID NO 2
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gaggccggcg aacccacctc tccgataagc cgatgctgac ccgtgttgtc tgttagccga      60
cgagactacg                                                             70

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aggctattcg gctacgactg ggcacaacag                                       30

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ttgtgcccag tcgtagccga atagc                                            25

<210> SEQ ID NO 5
```

```
<211> LENGTH: 15
<212> TYPE: DNA
<213> ORGANISM: Artificial Sequence
<220> FEATURE:
<223> OTHER INFORMATION: Description of Artificial Sequence:
      LNA modified oligonucleotide
<220> FEATURE:
<221> NAME/KEY: modified_base
<222> LOCATION: (1)..(15)
<223> OTHER INFORMATION: LNA monomer

<400> SEQUENCE: 5
gcccagtcgt agccg                                                        15

<210> SEQ ID NO 6
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
acaactgtgt tcactagcaa cctcaaacag acaccatggt gcacctgact cctgaggaga      60
agtctgc                                                                67

<210> SEQ ID NO 7
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgttgacaca agtgatcgtt ggagtttgtc tgtggtacca cgtggactga ggactcctct      60
tcagacg                                                                67

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gcagacttct cctcaggagt caggtgcacc                                        30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gttgcacctg actcctgagg agaagtctgc                                        30

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 10
gcagacttct cctcaggagt                                              20

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcagacttct cctcaggagt caggt                                        25

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcagacttct cctcaggagt caggtgcacc atggt                             35

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gcagacttct cctcaggagt caggtgcacc atggtgtctg                        40

<210> SEQ ID NO 14
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gcagacttct cctcaggagt caggtgcacc atggtgtctg tttgag                 46

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
actcctgagg agaagtctgc                                              20

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 16
acctgactcc tgaggagaag tctgc         25

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
accatggtgc acctgactcc tgaggagaag tctgc         35

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cagacaccat ggtgcacctg actcctgagg agaagtctgc         40

<210> SEQ ID NO 19
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
acctgactcc tgaggagaag tctgccgtta ctgccctgtg gggcaa         46

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ctgttgtgcc cagtcctagc cgaatagcct         30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aggctattcg gctacgactg ggcacaacag         30

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

```
gctattcggc tacgactggg cacaa                                           25

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
attcggctac gactgggcac                                                 20

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctgttgtgcc cagtcctagc cgaatagcct                                      30

<210> SEQ ID NO 25
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 25
gcuauucggc uacgacuggg cacaa                                           25

<210> SEQ ID NO 26
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 26
cuguugugcc caguccuagc cgaauagccu                                      30

<210> SEQ ID NO 27
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 27
uugugcccag ucguagccga auagc                                           25

<210> SEQ ID NO 28
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: phosphorothioate backbone

<400> SEQUENCE: 28
ttgtgcccag tcgtagccga atagc                                               25

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(4)
<223> OTHER INFORMATION: LNA monomer
<220> FEATURE:
<221> NAME/KEY: modified_base
<222> LOCATION: (12)..(15)
<223> OTHER INFORMATION: LNA monomer

<400> SEQUENCE: 29
gcccagtcgt agccg                                                          15

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(3)
<223> OTHER INFORMATION: LNA monomer
<220> FEATURE:
<221> NAME/KEY: modified_base
<222> LOCATION: (23)..(25)
<223> OTHER INFORMATION: LNA monomer

<400> SEQUENCE: 30
ttgtgcccag tcgtagccga atagc                                               25

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: PNA
      molecule
<220> FEATURE:
<221> NAME/KEY: misc_feature
<222> LOCATION: (1)
<223> OTHER INFORMATION: Lys-a
<220> FEATURE:
<221> NAME/KEY: misc_feature
<222> LOCATION: (18)
<223> OTHER INFORMATION: Gly-t

<400> SEQUENCE: 31
acgggtcagg atcggctt                                                       18

<210> SEQ ID NO 32
<211> LENGTH: 18
<212> TYPE: DNA
<213> ORGANISM: Artificial Sequence
<220> FEATURE:
```

```
<223> OTHER INFORMATION: Description of Artificial Sequence: PNA
      molecule
<220> FEATURE:
<221> NAME/KEY: misc_feature
<222> LOCATION: (1)
<223> OTHER INFORMATION: Lys-a
<220> FEATURE:
<221> NAME/KEY: misc_feature
<222> LOCATION: (18)
<223> OTHER INFORMATION: Gly-t

<400> SEQUENCE: 32
acgggtcagc atcggctt                                                   18

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: PNA
      molecule
<220> FEATURE:
<221> NAME/KEY: misc_feature
<222> LOCATION: (1)
<223> OTHER INFORMATION: AcGlu-g
<220> FEATURE:
<221> NAME/KEY: misc_feature
<222> LOCATION: (20)
<223> OTHER INFORMATION: Glu-t
<220> FEATURE:
<223> OTHER INFORMATION: c-term amidation

<400> SEQUENCE: 33
gtgcccagtc ctagccgaat                                                 20

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggtggagagg ctattcggct aggactgggc acaacagaca atcgg                     45

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 35 cagggatca agatctgat                                                   19

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 36
gcttcagtga caacgtcgag                                                 20

<210> SEQ ID NO 37
<211> LENGTH: 306
<212> TYPE: DNA
```

<213> ORGANISM: Artificial Sequence
<220> FEATURE:
<223> OTHER INFORMATION: Description of Artificial Sequence: Hyg target
      sequence

<400> SEQUENCE: 37
caggggatca agatctgatc aagagacagg atgaggatcg tttcgcatga ttgaacaaga    60
tggattgcac gcaggttctc cggccgcttg ggtggagagg ctattcggct atgactgggc   120
acaacagaca atcggctgct ctgatgccgc cgtgttccgg ctgtcagcgc aggggcgccc   180
ggttcttttt gtcaagaccg acctgtccgg tgccctgaat gaactgcagg acgaggcagc   240
gcggctatcg tggctggcca cgacgggcgt tccttgcgca gctgtgctcg acgttgtcac   300
tgaagc                                                              306

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(15)
<223> OTHER INFORMATION: LNA monomer

<400> SEQUENCE: 38
gcccagtcgt agccg                                                     15

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: PNA
      molecule
<220> FEATURE:
<221> NAME/KEY: misc_feature
<222> LOCATION: (1)
<223> OTHER INFORMATION: AcGlu-g
<220> FEATURE:
<221> NAME/KEY: misc_feature
<222> LOCATION: (20)
<223> OTHER INFORMATION: Glu-t
<220> FEATURE:
<223> OTHER INFORMATION: c-term amidation

<400> SEQUENCE: 39
gtgcccagtc ctagccgaat                                                20

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: phosphorothioate backbone

<400> SEQUENCE: 40
gcccagtcgt agccg                                                     15

<210> SEQ ID NO 41
<211> LENGTH: 15
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 41
gcccagucgu agccg                                                        15

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(15)
<223> OTHER INFORMATION: LNA monomer

<400> SEQUENCE: 42
gcccagtcgt agccg                                                        15

<210> SEQ ID NO 43
<211> LENGTH: 13
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(15)
<223> OTHER INFORMATION: LNA monomer

<400> SEQUENCE: 43
cccagtcgta gcc                                                          13

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(3)
<223> OTHER INFORMATION: LNA monomer
<220> FEATURE:
<221> NAME/KEY: modified_base
<222> LOCATION: (5)..(6)
<223> OTHER INFORMATION: LNA monomer
<220> FEATURE:
<221> NAME/KEY: modified_base
<222> LOCATION: (8)
<223> OTHER INFORMATION: LNA monomer
<220> FEATURE:
<221> NAME/KEY: modified_base
<222> LOCATION: (10)..(15)
<223> OTHER INFORMATION: LNA monomer
<220> FEATURE:
<221> NAME/KEY: modified_base
<222> LOCATION: (18)..(20)
<223> OTHER INFORMATION: LNA monomer

<400> SEQUENCE: 44
gtgcccagtc gtagccgaat                                                   20

<210> SEQ ID NO 45
```

```
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 45
tctgcacaat atttcaagc                                             19

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 46
aaatcagcca tgtagtg                                               17

<210> SEQ ID NO 47
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cgcagctatt tacccgcagg acctatccac gccctcctac atcga                45

<210> SEQ ID NO 48
<211> LENGTH: 10
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)
<223> OTHER INFORMATION: LNA monomer
<220> FEATURE:
<221> NAME/KEY: modified_base
<222> LOCATION: (3)..(7)
<223> OTHER INFORMATION: LNA monomer
<220> FEATURE:
<221> NAME/KEY: modified_base
<222> LOCATION: (10)
<223> OTHER INFORMATION: LNA monomer

<400> SEQUENCE: 48
ggataggtcc                                                       10

<210> SEQ ID NO 49
<211> LENGTH: 12
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)
<223> OTHER INFORMATION: LNA monomer
<220> FEATURE:
<221> NAME/KEY: modified_base
<222> LOCATION: (3)..(5)
<223> OTHER INFORMATION: LNA monomer
<220> FEATURE:
<221> NAME/KEY: modified_base
<222> LOCATION: (7)..(9)
```

```
<223> OTHER INFORMATION: LNA monomer
<220> FEATURE:
<221> NAME/KEY: modified_base
<222> LOCATION: (11)..(12)
<223> OTHER INFORMATION: LNA monomer

<400> SEQUENCE: 49
tggataggtc ct                                                              12

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(3)
<223> OTHER INFORMATION: LNA monomer
<220> FEATURE:
<221> NAME/KEY: modified_base
<222> LOCATION: (6)..(7)
<223> OTHER INFORMATION: LNA monomer
<220> FEATURE:
<221> NAME/KEY: modified_base
<222> LOCATION: (9)..(12)
<223> OTHER INFORMATION: LNA monomer
<220> FEATURE:
<221> NAME/KEY: modified_base
<222> LOCATION: (14)..(15)
<223> OTHER INFORMATION: LNA monomer

<400> SEQUENCE: 50
gtggataggt cctgc                                                           15

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(2)
<223> OTHER INFORMATION: LNA monomer
<220> FEATURE:
<221> NAME/KEY: modified_base
<222> LOCATION: (4)..(6)
<223> OTHER INFORMATION: LNA monomer
<220> FEATURE:
<221> NAME/KEY: modified_base
<222> LOCATION: (9)..(11)
<223> OTHER INFORMATION: LNA monomer
<220> FEATURE:
<221> NAME/KEY: modified_base
<222> LOCATION: (13)..(15)
<223> OTHER INFORMATION: LNA monomer

<400> SEQUENCE: 51
gtggataggt cctgc                                                           15

<210> SEQ ID NO 52
<211> LENGTH: 45
<212> TYPE: DNA
<213> ORGANISM: Artificial Sequence
<220> FEATURE:
<223> OTHER INFORMATION: Description of Artificial Sequence: Linker
      oligonucleotide

<400> SEQUENCE: 52
```
ggtggagagg ctattcggct aggactgggc acaacagaca atcgg       45

<210> SEQ ID NO 53
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gaggctattc ggctaggact gggcacaaca g       31

<210> SEQ ID NO 54
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gaggctattc ggctacgact gggcacaaca g       31

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
atttacccgc aggacctatc cacgccctcc t       31

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
atttacccgc aggacgtatc cacgccctcc t       31

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: LNA/PNA
      modified oligonucleotide
<220> FEATURE:
<221> NAME/KEY: modified_base
<222> LOCATION: (1)..(2)
<223> OTHER INFORMATION: LNA monomer
<220> FEATURE:
<221> NAME/KEY: modified_base
<222> LOCATION: (4)..(6)
<223> OTHER INFORMATION: LNA monomer
<220> FEATURE:
<221> NAME/KEY: modified_base
<222> LOCATION: (8)..(10)
<223> OTHER INFORMATION: LNA monomer
<220> FEATURE:
<221> NAME/KEY: modified_base
<222> LOCATION: (12)..(15)
<223> OTHER INFORMATION: LNA monomer
<220> FEATURE:

```
<223> OTHER INFORMATION: may be acetylated

<400> SEQUENCE: 57
gtggataggt cctgc                                                    15

<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(2)
<223> OTHER INFORMATION: LNA monomer
<220> FEATURE:
<221> NAME/KEY: modified_base
<222> LOCATION: (4)..(6)
<223> OTHER INFORMATION: LNA monomer
<220> FEATURE:
<221> NAME/KEY: modified_base
<222> LOCATION: (8)..(10)
<223> OTHER INFORMATION: LNA monomer
<220> FEATURE:
<221> NAME/KEY: modified_base
<222> LOCATION: (12)..(15)
<223> OTHER INFORMATION: LNA monomer

<400> SEQUENCE: 58
gtggatacgt cctgc                                                    15

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(2)
<223> OTHER INFORMATION: LNA monomer
<220> FEATURE:
<221> NAME/KEY: modified_base
<222> LOCATION: (4)..(6)
<223> OTHER INFORMATION: LNA monomer
<220> FEATURE:
<221> NAME/KEY: modified_base
<222> LOCATION: (8)..(10)
<223> OTHER INFORMATION: LNA monomer
<220> FEATURE:
<221> NAME/KEY: modified_base
<222> LOCATION: (12)..(15)
<223> OTHER INFORMATION: LNA monomer

<400> SEQUENCE: 59
gtggatatgt cctgc                                                    15

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gctattcggc taggactggg cacaa                                         25

<210> SEQ ID NO 61
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ttgtgcccag tcctagccga atagc                                            25

<210> SEQ ID NO 62
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
atttacccgc aggacatatc cacgccctcc t                                     31

<210> SEQ ID NO 63
<211> LENGTH: 15
<212> TYPE: DNA
<213> ORGANISM: Artificial Sequence
<220> FEATURE:
<223> OTHER INFORMATION: Description of Artificial Sequence: LNA/PNA
      modified oligonucleotide
<220> FEATURE:
<221> NAME/KEY: modified_base
<222> LOCATION: (1)..(2)
<223> OTHER INFORMATION: LNA monomer
<220> FEATURE:
<221> NAME/KEY: modified_base
<222> LOCATION: (4)..(6)
<223> OTHER INFORMATION: LNA monomer
<220> FEATURE:
<221> NAME/KEY: modified_base
<222> LOCATION: (8)..(10)
<223> OTHER INFORMATION: LNA monomer
<220> FEATURE:
<221> NAME/KEY: modified_base
<222> LOCATION: (12)..(15)
<223> OTHER INFORMATION: LNA monomer
<220> FEATURE:
<223> OTHER INFORMATION: may be acetylated

<400> SEQUENCE: 63
gtggatatgt cctgc                                                       15

<210> SEQ ID NO 64
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cgcagctatt tacccgcagg acctatccac gccctcctac atcga                      45

<210> SEQ ID NO 65
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
```
cgcagctatt tacccgcagg acctatccac gccctcctac atcga 45

<210> SEQ ID NO 66
<211> LENGTH: 15
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(2)
<223> OTHER INFORMATION: LNA monomer
<220> FEATURE:
<221> NAME/KEY: modified_base
<222> LOCATION: (4)..(6)
<223> OTHER INFORMATION: LNA monomer
<220> FEATURE:
<221> NAME/KEY: modified_base
<222> LOCATION: (8)..(10)
<223> OTHER INFORMATION: LNA monomer
<220> FEATURE:
<221> NAME/KEY: modified_base
<222> LOCATION: (12)..(15)
<223> OTHER INFORMATION: LNA monomer

<400> SEQUENCE: 66
gtggataggt cctgc 15

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
acccgcagga cctatccacg ccc 23

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
acccgcagga cgtatccacg ccc 23

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ttacccgcag gacctatcca cgccctc 27

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 70
ttacccgcag gacgtatcca cgccctc                                         27

<210> SEQ ID NO 71
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ctatttaccc gcaggaccta tccacgccct cctac                                35

<210> SEQ ID NO 72
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ctatttaccc gcaggacgta tccacgccct cctac                                35

<210> SEQ ID NO 73
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
agctatttac ccgcaggacc tatccacgcc ctcctacat                            39

<210> SEQ ID NO 74
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
agctatttac ccgcaggacg tatccacgcc ctcctacat                            39

<210> SEQ ID NO 75
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gcagctattt acccgcagga cctatccacg ccctcctaca tcg                       43

<210> SEQ ID NO 76
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
```

```
gcagctattt acccgcagga cgtatccacg ccctcctaca tcg                    43

<210> SEQ ID NO 77
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 77 gauaggucc                                                          9

<210> SEQ ID NO 78
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 78 gauacgucc                                                          9

<210> SEQ ID NO 79
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 79
uggauagguc cug                                                    13

<210> SEQ ID NO 80
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 80
uggauacguc cug                                                    13

<210> SEQ ID NO 81
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 81
cguggauagg uccugcg                                                17
```

```
<210> SEQ ID NO 82
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 82
cguggauacg uccugcg                                                    17

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 83
ggcguggaua gguccugcgg g                                               21

<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 84
ggcguggaua cguccugcgg g                                               21

<210> SEQ ID NO 85
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 85
agggcgugga uagguccugc gggua                                           25

<210> SEQ ID NO 86
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 86
agggcgugga uacguccugc gggua                                           25

<210> SEQ ID NO 87
<211> LENGTH: 51
<212> TYPE: DNA
<213> ORGANISM: Artificial Sequence
```

```
-continued

<220> FEATURE:
<223> OTHER INFORMATION: Description of Artificial Sequence: Synthetic
      oligonucleotide

<400> SEQUENCE: 87
cccgccccgc ggcctgaaga tgtcggccac cttcatcggc aacagcacgg c          51

<210> SEQ ID NO 88
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ggcctgaaga tgtcggccac cttcatcggc a                                31

<210> SEQ ID NO 89
<211> LENGTH: 15
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(15)
<223> OTHER INFORMATION: LNA monomer

<400> SEQUENCE: 89
aaggtggccg acatc                                                  15

<210> SEQ ID NO 90
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
atgccgccca tgcaggaact gttacacatg t                                31

<210> SEQ ID NO 91
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
atgccgccca tgcagaaact gttacacatg t                                31

<210> SEQ ID NO 92
<211> LENGTH: 15
<212> TYPE: DNA
<213> ORGANISM: Artificial Sequence
<220> FEATURE:
<223> OTHER INFORMATION: Description of Artificial Sequence: PNA
      molecule

<400> SEQUENCE: 92
aacagttcct gcatg                                                  15

<210> SEQ ID NO 93
```

```
<211> LENGTH: 15
<212> TYPE: DNA
<213> ORGANISM: Artificial Sequence
<220> FEATURE:
<223> OTHER INFORMATION: Description of Artificial Sequence: PNA
      molecule

<400> SEQUENCE: 93
aacagtttct gcatg                                                          15

<210> SEQ ID NO 94
<211> LENGTH: 15
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(15)
<223> OTHER INFORMATION: LNA monomer

<400> SEQUENCE: 94
aacagttcct gcatg                                                          15

<210> SEQ ID NO 95
<211> LENGTH: 15
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(15)
<223> OTHER INFORMATION: LNA monomer

<400> SEQUENCE: 95
aacagtttct gcatg                                                          15

<210> SEQ ID NO 96
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ggcactcttg cctacgccac cagctccaac t                                        31

<210> SEQ ID NO 97
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ggcactcttg cctacgtcac cagctccaac t                                        31

<210> SEQ ID NO 98
<211> LENGTH: 15
<212> TYPE: DNA
<213> ORGANISM: Artificial Sequence
<220> FEATURE:
<223> OTHER INFORMATION: Description of Artificial Sequence: PNA
      molecule
```

```
<400> SEQUENCE: 98
gctggtggcg taggc                                              15

<210> SEQ ID NO 99
<211> LENGTH: 15
<212> TYPE: DNA
<213> ORGANISM: Artificial Sequence
<220> FEATURE:
<223> OTHER INFORMATION: Description of Artificial Sequence: PNA
      molecule

<400> SEQUENCE: 99
gctggtgacg taggc                                              15

<210> SEQ ID NO 100
<211> LENGTH: 15
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(15)
<223> OTHER INFORMATION: LNA monomer

<400> SEQUENCE: 100
gctggtggcg taggc                                              15

<210> SEQ ID NO 101
<211> LENGTH: 15
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(15)
<223> OTHER INFORMATION: LNA monomer

<400> SEQUENCE: 101
gctggtgacg taggc                                              15

<210> SEQ ID NO 102
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
acggcagact tctcctcagg agtcaggtgc a                            31

<210> SEQ ID NO 103
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
acggcagact tctccacagg agtcaggtgc a                            31
```

```
<210> SEQ ID NO 104
<211> LENGTH: 15
<212> TYPE: DNA
<213> ORGANISM: Artificial Sequence
<220> FEATURE:
<223> OTHER INFORMATION: Description of Artificial Sequence: PNA
      molecule
<220> FEATURE:
<223> OTHER INFORMATION: may be acetylated

<400> SEQUENCE: 104
actcctgagg agaag                                                     15

<210> SEQ ID NO 105
<211> LENGTH: 15
<212> TYPE: DNA
<213> ORGANISM: Artificial Sequence
<220> FEATURE:
<223> OTHER INFORMATION: Description of Artificial Sequence: PNA
      molecule

<400> SEQUENCE: 105
actcctgtgg agaag                                                     15

<210> SEQ ID NO 106
<211> LENGTH: 15
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(15)
<223> OTHER INFORMATION: LNA monomer

<400> SEQUENCE: 106
actcctgagg agaag                                                     15

<210> SEQ ID NO 107
<211> LENGTH: 15
<212> TYPE: DNA
<213> ORGANISM: Artificial Sequence
<220> FEATURE:
<223> OTHER INFORMATION: Description of Artificial Sequence: LNA
      modified oligonucleotide
<220> FEATURE:
<221> NAME/KEY: modified_base
<222> LOCATION: (1)..(15)
<223> OTHER INFORMATION: LNA monomer

<400> SEQUENCE: 107
actcctgtgg agaag                                                     15

<210> SEQ ID NO 108
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gaggctattc ggctatgact gggcacaaca g                                   31

<210> SEQ ID NO 109
<211> LENGTH: 20
<212> TYPE: DNA
<213> ORGANISM: Artificial Sequence
```

```
<220> FEATURE:
<223> OTHER INFORMATION: Description of Artificial Sequence: PNA
      molecule
<220> FEATURE:
<223> OTHER INFORMATION: may be acetylated

<400> SEQUENCE: 109
gtgcccagtc atagccgaat                                                  20

<210> SEQ ID NO 110
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
acggcagact tctcctcagg agtcaggtgc a                                     31

<210> SEQ ID NO 111
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
acggcagact tctcctcagg agtcaggtgc a                                     31

<210> SEQ ID NO 112
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 112
acuccugagg agaag                                                       15

<210> SEQ ID NO 113
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 113
acuccugagg agaag                                                       15

<210> SEQ ID NO 114
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: all bases 2'-OMe modified

<400> SEQUENCE: 114
```

-continued

```
guggauaggu ccugc                                                        15

<210> SEQ ID NO 115
<211> LENGTH: 478
<212> TYPE: DNA
<213> ORGANISM: Artificial Sequence
<220> FEATURE:
<223> OTHER INFORMATION: Description of Artificial Sequence: Kan target
      sequence

<400> SEQUENCE: 115
cgctgagata ggtgcctcac tgattaagca ttggtaactg tcagaccaag tttactcata      60
tatactttag attgatttaa aacttcattt ttaatttaaa aggatctagg tgaagatcct     120
ttttgataat ctcatgacca aaatcccttaa cgtgagttt tcgttccact gagcgtcaga     180
ccccgtagaa aagatcaaag gatcttcttg agatcctttt tttctgcgcg taatctgctg     240
cttgcaaaca aaaaaccac cgctaccagc ggtggtttgt ttgccggatc aagagctacc     300 aactctttt ccgaaggtaa ctggcttcag cagagcgcag ataccaaata ctgtccttct     360
agtgtagccg tagttaggcc accacttcaa gaactctgta gcaccgccta catcctcgc     420 tctgctaatc ctgttaccag tggctgctgc cagtggcgat aagtcgtgtc ttaccggg      478
```